United States Patent
Hagiya et al.

(10) Patent No.: US 9,938,505 B2
(45) Date of Patent: Apr. 10, 2018

(54) POLYPEPTIDE COMPOSITION AND CULTURE METHOD FOR PLURIPOTENT STEM CELL USING SAME

(71) Applicant: FUJIFILM Corporation, Tokyo (JP)

(72) Inventors: Keita Hagiya, Kanagawa (JP); Sanae Morioka, Kanagawa (JP); Yuta Murakami, Kanagawa (JP); Rie Hando, Kanagawa (JP); Kouo Suzuki, Kanagawa (JP); Yoshihide Iwaki, Kanagawa (JP); Tasuku Sasaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/139,497

(22) Filed: Apr. 27, 2016

(65) Prior Publication Data

US 2016/0272945 A1    Sep. 22, 2016

Related U.S. Application Data

(63) Continuation of application No. PCT/JP2014/078813, filed on Oct. 29, 2014.

(30) Foreign Application Priority Data

Oct. 31, 2013   (JP) .................................. 2013-227583

(51) Int. Cl.
| | | |
|---|---|---|
| *C07K 14/78* | (2006.01) | |
| *C12N 5/00* | (2006.01) | |
| *C12N 5/074* | (2010.01) | |

(52) U.S. Cl.
CPC ............ *C12N 5/0696* (2013.01); *C07K 14/78* (2013.01); *C12N 5/0018* (2013.01); *C12N 2500/32* (2013.01); *C12N 2500/38* (2013.01); *C12N 2501/115* (2013.01); *C12N 2501/15* (2013.01); *C12N 2501/33* (2013.01); *C12N 2501/998* (2013.01)

(58) Field of Classification Search
CPC .............................. C07K 14/78; C12N 5/0018
See application file for complete search history.

(56) References Cited

U.S. PATENT DOCUMENTS

2012/0301962 A1   11/2012   Thomson et al.

FOREIGN PATENT DOCUMENTS

| JP | 2001-017183 A | 1/2001 |
|---|---|---|
| JP | 2010-029186 A | 2/2010 |

OTHER PUBLICATIONS

Prowse et al., Biomaterials 31:8281-8288 (2010).*
Yoneda et al, "Characterization of the Ligand Binding Activities of Vitronectin: Interaction of Vitronectin with Lipids and Identification of the Binding Domains for Various Ligands Using Recombinant Domains", Biochemistry, vol. 37, No. 18, May 1, 1998, pp. 6351-6360, XP055304548.
Zhao et al, "The Cell Attachment and Spreading Activity of Vitronectin is Dependent on the Arg-Gly-Asp Sequence—Analysis by Construction of RGD and Domain Deletion Mutants," Biochemical and Biophysical Research Communications, vol. 192, No. 2, Apr. 30, 1993, pp. 575-582, XP024768010.
Communication, dated Sep. 29, 2016, issued in corresponding EP Application No. 14857014.6, 6 pages in English.
Chunhui Xu et al., "Feeder-free growth of undifferentiated human embryonic stem cells," Nature Biotechnology, Oct. 2001, pp. 971-974, vol. 19.
Andrew B.J. Prowse et al., "Long term culture of human embryonic stem cells on recombinant vitronectin in ascorbate free media," Biomaterials, 2010, pp. 8281-8288, vol. 31.
Zara Melkoumian et al., "Synthetic peptide-acrylate surfaces for long-term self-renewal and cardiomyocyte differentiation of human embryonic stem cells," Nature Biotechnology, Jun. 2010, (available online May 30, 2010) pp. 606-610, vol. 28, No. 6.
Perpotech Fact Sheets, Funakshi Co., Ltd., Dec. 2010, p. 4.
Funakoshi News, issue of Aug. 15, 2012, p. 19.
Stefan R. Braam et al., "Recombinant Vitronectin is a Functionally Defined Substrate That Supports Human Embryonic Stem Cell Self-Renewal via αVβ5 Integrin," Stem Cells, 2008, pp. 2257-2265, vol. 26, No. 9.
Shintaro Suzuki et al., Complete amino acid sequence of human vitronectin deduced from cDNA. Similarity of cell attachment sites in vitronectin and fibronectin, The EMBRO Journal, 1985, pp. 2519-2524, vol. 4, No. 10.
Written Opinion of the International Searching Authority of PCT/JP2014/078813 dated Feb. 3, 2015.
International Search Report of PCT/JP2014/078813 dated Feb. 3, 2015.
Communication dated Feb. 14, 2017, from the Japanese Patent Office in counterpart application No. 2015-545279.

(Continued)

Primary Examiner — Daniel C Gamett
(74) Attorney, Agent, or Firm — Sughrue Mion, PLLC

(57) ABSTRACT

A polypeptide composition induces a pluripotent stem cell culturing property, particularly, an excellent cell growth ability. The polypeptide composition contains a predetermined polypeptide including an amino acid sequence of human vitronectin or an amino acid sequence of a predetermined first region derived from human vitronectin. The polypeptide composition includes a multimeric polypeptide, which is composed of two or more monomers held together by intermolecular cross-linking via cysteine residues included in the first region, in an amount equal to or less than 20% by mass of a total mass of polypeptides contained in the composition. A culture method for pluripotent stem cells includes culturing pluripotent stem cells in the presence of the polypeptide composition. Also provided is a culture vessel including a support which has a cell culture surface and the polypeptide contained in the polypeptide composition disposed on the cell culture surface of the support.

15 Claims, 6 Drawing Sheets

(56) References Cited

OTHER PUBLICATIONS

Office Action dated Aug. 29, 2017 from the Japanese Patent Office in counterpart Japanese Application No. 2015-545279.
Office Action dated Jul. 12, 2017 issued by the Canadian Intellectual Property Office in counterpart Canadian Application No. 2,928,623.

* cited by examiner

_US 9,938,505 B2_

SEQUENCE LISTING

```
<160> NUMBER OF SEQ ID NOS: 42

<210> SEQ ID NO 1
<211> LENGTH: 459
<212> TYPE: PRT
<213> ORGANISM: Homo sapiens

<400> SEQUENCE: 1

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Tyr Thr Val Tyr Asp Asp Gly Glu Glu
        50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95

Leu Lys Pro Glu Glu Glu Ala Pro Ala Pro Glu Val Gly Ala Ser Lys
            100                 105                 110

Pro Glu Gly Ile Asp Ser Arg Pro Glu Thr Leu His Pro Gly Arg Pro
        115                 120                 125

Gln Pro Pro Ala Glu Glu Glu Leu Cys Ser Gly Lys Pro Phe Asp Ala
    130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
                165                 170                 175

Ile Arg Asp Val Trp Gly Ile Glu Gly Pro Ile Asp Ala Ala Phe Thr
            180                 185                 190

Arg Ile Asn Cys Gln Gly Lys Thr Tyr Leu Phe Lys Gly Ser Gln Tyr
        195                 200                 205
```

-continued

```
Trp Arg Phe Glu Asp Gly Val Leu Asp Pro Asp Tyr Pro Arg Asn Ile
    210                 215                 220
Ser Asp Gly Phe Asp Gly Ile Pro Asp Asn Val Asp Ala Ala Leu Ala
225                 230                 235                 240
Leu Pro Ala His Ser Tyr Ser Gly Arg Glu Arg Val Tyr Phe Phe Lys
                    245                 250                 255
Gly Lys Gln Tyr Trp Glu Tyr Gln Phe Gln His Gln Pro Ser Gln Glu
                260                 265                 270
Glu Cys Glu Gly Ser Ser Leu Ser Ala Val Phe Glu His Phe Ala Met
            275                 280                 285
Met Gln Arg Asp Ser Trp Glu Asp Ile Phe Glu Leu Leu Phe Trp Gly
290                 295                 300
Arg Thr Ser Ala Gly Thr Arg Gln Pro Gln Phe Ile Ser Arg Asp Trp
305                 310                 315                 320
His Gly Val Pro Gly Gln Val Asp Ala Ala Met Ala Gly Arg Ile Tyr
                    325                 330                 335
Ile Ser Gly Met Ala Pro Arg Pro Ser Leu Ala Lys Lys Gln Arg Phe
                340                 345                 350
Arg His Arg Asn Arg Lys Gly Tyr Arg Ser Gln Arg Gly His Ser Arg
            355                 360                 365
Gly Arg Asn Gln Asn Ser Arg Arg Pro Ser Arg Ala Thr Trp Leu Ser
370                 375                 380
Leu Phe Ser Ser Glu Glu Ser Asn Leu Gly Ala Asn Asn Tyr Asp Asp
385                 390                 395                 400
Tyr Arg Met Asp Trp Leu Val Pro Ala Thr Cys Glu Pro Ile Gln Ser
                    405                 410                 415
Val Phe Phe Phe Ser Gly Asp Lys Tyr Tyr Arg Val Asn Leu Arg Thr
                420                 425                 430
Arg Arg Val Asp Thr Val Asp Pro Pro Tyr Pro Arg Ser Ile Ala Gln
            435                 440                 445
Tyr Trp Leu Gly Cys Pro Ala Pro Gly His Leu
    450                 455

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

Cys Ser Tyr Tyr Gln Ser Cys
1               5

<210> SEQ ID NO 3
<211> LENGTH: 32
<212> TYPE: PRT
<213> ORGANISM: Artificial Sequence
<220> FEATURE:
<223> OTHER INFORMATION: Syntyhetic heparin Binding Domain peptide

<400> SEQUENCE: 3

Pro Arg Pro Ser Leu Ala Lys Lys Gln Arg Phe Arg His Arg Asn Arg
1               5                   10                  15
Lys Gly Tyr Arg Ser Gln Arg Gly His Ser Arg Gly Arg Asn Gln Asn
            20                  25                  30
```

```
<210> SEQ ID NO 4
<211> LENGTH: 246
<212> TYPE: PRT
<213> ORGANISM: Artificial Sequence
<220> FEATURE:
<223> OTHER INFORMATION: Synthetic peptide

<400> SEQUENCE: 4

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Pro Ser Gln Glu Glu Cys Glu Gly Ser
    50                  55                  60

Ser Leu Ser Ala Val Phe Glu His Phe Ala Met Met Gln Arg Asp Ser
65                  70                  75                  80

Trp Glu Asp Ile Phe Glu Leu Leu Phe Trp Gly Arg Thr Ser Ala Gly
                85                  90                  95

Thr Arg Gln Pro Gln Phe Ile Ser Arg Asp Trp His Gly Val Pro Gly
            100                 105                 110

Gln Val Asp Ala Ala Met Ala Gly Arg Ile Tyr Ile Ser Gly Met Ala
        115                 120                 125

Pro Arg Pro Ser Leu Ala Lys Lys Gln Arg Phe Arg His Arg Asn Arg
130                 135                 140

Lys Gly Tyr Arg Ser Gln Arg Gly His Ser Arg Gly Arg Asn Gln Asn
145                 150                 155                 160

Ser Arg Arg Pro Ser Arg Ala Thr Trp Leu Ser Leu Phe Ser Ser Glu
                165                 170                 175

Glu Ser Asn Leu Gly Ala Asn Asn Tyr Asp Asp Tyr Arg Met Asp Trp
            180                 185                 190

Leu Val Pro Ala Thr Cys Glu Pro Ile Gln Ser Val Phe Phe Phe Ser
        195                 200                 205

Gly Asp Lys Tyr Tyr Arg Val Asn Leu Arg Thr Arg Arg Val Asp Thr
210                 215                 220

Val Asp Pro Pro Tyr Pro Arg Ser Ile Ala Gln Tyr Trp Leu Gly Cys
225                 230                 235                 240

Pro Ala Pro Gly His Leu
                245

<210> SEQ ID NO 5
<211> LENGTH: 87
<212> TYPE: PRT
<213> ORGANISM: Artificial Sequence
<220> FEATURE:
<223> OTHER INFORMATION: Synthetic peptide

<400> SEQUENCE: 5

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Pro Arg Pro Ser Leu Ala Lys Lys Gln
    50                  55                  60
```

Arg Phe Arg His Arg Asn Arg Lys Gly Tyr Arg Ser Gln Arg Gly His
65                  70                  75                  80

Ser Arg Gly Arg Asn Gln Asn
            85

<210> SEQ ID NO 6
<211> LENGTH: 107
<212> TYPE: PRT
<213> ORGANISM: Artificial Sequence
<220> FEATURE:
<223> OTHER INFORMATION: Synthetic peptide

<400> SEQUENCE: 6

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Gly Val Pro Gly Gln Val Asp Ala Ala
    50                  55                  60

Met Ala Gly Arg Ile Tyr Ile Ser Gly Met Ala Pro Arg Pro Ser Leu
65                  70                  75                  80

Ala Lys Lys Gln Arg Phe Arg His Arg Asn Arg Lys Gly Tyr Arg Ser
                85                  90                  95

Gln Arg Gly His Ser Arg Gly Arg Asn Gln Asn
            100                 105

<210> SEQ ID NO 7
<211> LENGTH: 117
<212> TYPE: PRT
<213> ORGANISM: Artificial Sequence
<220> FEATURE:
<223> OTHER INFORMATION: Synthetic peptide

<400> SEQUENCE: 7

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Gln Pro Gln Phe Ile Ser Arg Asp Trp
    50                  55                  60

His Gly Val Pro Gly Gln Val Asp Ala Ala Met Ala Gly Arg Ile Tyr
65                  70                  75                  80

Ile Ser Gly Met Ala Pro Arg Pro Ser Leu Ala Lys Lys Gln Arg Phe
                85                  90                  95

Arg His Arg Asn Arg Lys Gly Tyr Arg Ser Gln Arg Gly His Ser Arg
            100                 105                 110

Gly Arg Asn Gln Asn
        115

<210> SEQ ID NO 8
<211> LENGTH: 127
<212> TYPE: PRT
<213> ORGANISM: Artificial Sequence
<220> FEATURE:
<223> OTHER INFORMATION: Synthetic peptide

<400> SEQUENCE: 8

```
Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Phe Trp Gly Arg Thr Ser Ala Gly Thr
    50                  55                  60

Arg Gln Pro Gln Phe Ile Ser Arg Asp Trp His Gly Val Pro Gly Gln
65                  70                  75                  80

Val Asp Ala Ala Met Ala Gly Arg Ile Tyr Ile Ser Gly Met Ala Pro
                85                  90                  95

Arg Pro Ser Leu Ala Lys Lys Gln Arg Phe Arg His Arg Asn Arg Lys
            100                 105                 110

Gly Tyr Arg Ser Gln Arg Gly His Ser Arg Gly Arg Asn Gln Asn
        115                 120                 125
```

<210> SEQ ID NO 9
<211> LENGTH: 245
<212> TYPE: PRT
<213> ORGANISM: Artificial Sequence
<220> FEATURE:
<223> OTHER INFORMATION: Synthetic peptide

<400> SEQUENCE: 9

```
Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Ser Gln Glu Ser Glu Gly Ser Ser
    50                  55                  60

Leu Ser Ala Val Phe Glu His Phe Ala Met Met Gln Arg Asp Ser Trp
65                  70                  75                  80

Glu Asp Ile Phe Glu Leu Leu Phe Trp Gly Arg Thr Ser Ala Gly Thr
                85                  90                  95

Arg Gln Pro Gln Phe Ile Ser Arg Asp Trp His Gly Val Pro Gly Gln
            100                 105                 110

Val Asp Ala Ala Met Ala Gly Arg Ile Tyr Ile Ser Gly Met Ala Pro
        115                 120                 125

Arg Pro Ser Leu Ala Lys Lys Gln Arg Phe Arg His Arg Asn Arg Lys
    130                 135                 140

Gly Tyr Arg Ser Gln Arg Gly His Ser Arg Gly Arg Asn Gln Asn Ser
145                 150                 155                 160

Arg Arg Pro Ser Arg Ala Thr Trp Leu Ser Leu Phe Ser Ser Glu Glu
                165                 170                 175

Ser Asn Leu Gly Ala Asn Asn Tyr Asp Asp Tyr Arg Met Asp Trp Leu
            180                 185                 190

Val Pro Ala Thr Ser Glu Pro Ile Gln Ser Val Phe Phe Phe Ser Gly
        195                 200                 205

Asp Lys Tyr Tyr Arg Val Asn Leu Arg Thr Arg Val Asp Thr Val
    210                 215                 220

Asp Pro Pro Tyr Pro Arg Ser Ile Ala Gln Tyr Trp Leu Gly Ser Pro
```

```
                225                 230                 235                 240

Ala Pro Gly His Leu
                245

<210> SEQ ID NO 10
<211> LENGTH: 159
<212> TYPE: PRT
<213> ORGANISM: Artificial Sequence
<220> FEATURE:
<223> OTHER INFORMATION: Synthetic peptide

<400> SEQUENCE: 10

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Ser Gln Glu Glu Ser Glu Gly Ser Ser
    50                  55                  60

Leu Ser Ala Val Phe Glu His Phe Ala Met Met Gln Arg Asp Ser Trp
65                  70                  75                  80

Glu Asp Ile Phe Glu Leu Leu Phe Trp Gly Arg Thr Ser Ala Gly Thr
                85                  90                  95

Arg Gln Pro Gln Phe Ile Ser Arg Asp Trp His Gly Val Pro Gly Gln
            100                 105                 110

Val Asp Ala Ala Met Ala Gly Arg Ile Tyr Ile Ser Gly Met Ala Pro
        115                 120                 125

Arg Pro Ser Leu Ala Lys Lys Gln Arg Phe Arg His Arg Asn Arg Lys
    130                 135                 140

Gly Tyr Arg Ser Gln Arg Gly His Ser Arg Gly Arg Asn Gln Asn
145                 150                 155

<210> SEQ ID NO 11
<211> LENGTH: 165
<212> TYPE: PRT
<213> ORGANISM: Artificial Sequence
<220> FEATURE:
<223> OTHER INFORMATION: Synthetic peptide

<400> SEQUENCE: 11

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Ser Gln Glu Glu Ser Glu Gly Ser Ser
    50                  55                  60

Leu Ser Ala Val Phe Glu His Phe Ala Met Met Gln Arg Asp Ser Trp
65                  70                  75                  80

Glu Asp Ile Phe Glu Leu Leu Phe Trp Gly Arg Thr Ser Ala Gly Thr
                85                  90                  95

Arg Gln Pro Gln Phe Ile Ser Arg Asp Trp His Gly Val Pro Gly Gln
            100                 105                 110

Val Asp Ala Ala Met Ala Gly Arg Ile Tyr Ile Ser Gly Met Ala Pro
        115                 120                 125
```

```
Arg Pro Ser Leu Ala Lys Lys Gln Arg Phe Arg His Arg Asn Arg Lys
        130                 135                 140

Gly Tyr Arg Ser Gln Arg Gly His Ser Arg Gly Arg Asn Gln Asn Ser
145                 150                 155                 160

Arg Arg Pro Ser Arg
                165

<210> SEQ ID NO 12
<211> LENGTH: 175
<212> TYPE: PRT
<213> ORGANISM: Artificial Sequence
<220> FEATURE:
<223> OTHER INFORMATION: Synthetic peptide

<400> SEQUENCE: 12

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Ser Gln Glu Ser Glu Gly Ser Ser
    50                  55                  60

Leu Ser Ala Val Phe Glu His Phe Ala Met Met Gln Arg Asp Ser Trp
65                  70                  75                  80

Glu Asp Ile Phe Glu Leu Leu Phe Trp Gly Arg Thr Ser Ala Gly Thr
                85                  90                  95

Arg Gln Pro Gln Phe Ile Ser Arg Asp Trp His Gly Val Pro Gly Gln
            100                 105                 110

Val Asp Ala Ala Met Ala Gly Arg Ile Tyr Ile Ser Gly Met Ala Pro
        115                 120                 125

Arg Pro Ser Leu Ala Lys Lys Gln Arg Phe Arg His Arg Asn Arg Lys
    130                 135                 140

Gly Tyr Arg Ser Gln Arg Gly His Ser Arg Gly Arg Asn Gln Asn Ser
145                 150                 155                 160

Arg Arg Pro Ser Arg Ala Thr Trp Leu Ser Leu Phe Ser Glu
                165                 170                 175

<210> SEQ ID NO 13
<211> LENGTH: 185
<212> TYPE: PRT
<213> ORGANISM: Artificial Sequence
<220> FEATURE:
<223> OTHER INFORMATION: Synthetic peptide

<400> SEQUENCE: 13

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Ser Gln Glu Ser Glu Gly Ser Ser
    50                  55                  60

Leu Ser Ala Val Phe Glu His Phe Ala Met Met Gln Arg Asp Ser Trp
65                  70                  75                  80

Glu Asp Ile Phe Glu Leu Leu Phe Trp Gly Arg Thr Ser Ala Gly Thr
                85                  90                  95
```

```
Arg Gln Pro Gln Phe Ile Ser Arg Asp Trp His Gly Val Pro Gly Gln
            100                 105                 110

Val Asp Ala Ala Met Ala Gly Arg Ile Tyr Ile Ser Gly Met Ala Pro
        115                 120                 125

Arg Pro Ser Leu Ala Lys Lys Gln Arg Phe Arg His Arg Asn Arg Lys
    130                 135                 140

Gly Tyr Arg Ser Gln Arg Gly His Ser Arg Gly Arg Asn Gln Asn Ser
145                 150                 155                 160

Arg Arg Pro Ser Arg Ala Thr Trp Leu Ser Leu Phe Ser Ser Glu Glu
                165                 170                 175

Ser Asn Leu Gly Ala Asn Asn Tyr Asp
            180                 185

<210> SEQ ID NO 14
<211> LENGTH: 247
<212> TYPE: PRT
<213> ORGANISM: Artificial Sequence
<220> FEATURE:
<223> OTHER INFORMATION: Synthetic peptide RCP-1

<400> SEQUENCE: 14

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Pro Ser Gln Glu Glu Cys Glu Gly
    50                  55                  60

Ser Ser Leu Ser Ala Val Phe Glu His Phe Ala Met Met Gln Arg Asp
65                  70                  75                  80

Ser Trp Glu Asp Ile Phe Glu Leu Leu Phe Trp Gly Arg Thr Ser Ala
                85                  90                  95

Gly Thr Arg Gln Pro Gln Phe Ile Ser Arg Asp Trp His Gly Val Pro
            100                 105                 110

Gly Gln Val Asp Ala Ala Met Ala Gly Arg Ile Tyr Ile Ser Gly Met
        115                 120                 125

Ala Pro Arg Pro Ser Leu Ala Lys Lys Gln Arg Phe Arg His Arg Asn
    130                 135                 140

Arg Lys Gly Tyr Arg Ser Gln Arg Gly His Ser Arg Gly Arg Asn Gln
145                 150                 155                 160

Asn Ser Arg Arg Pro Ser Arg Ala Thr Trp Leu Ser Leu Phe Ser Ser
                165                 170                 175

Glu Glu Ser Asn Leu Gly Ala Asn Asn Tyr Asp Asp Tyr Arg Met Asp
            180                 185                 190

Trp Leu Val Pro Ala Thr Cys Glu Pro Ile Gln Ser Val Phe Phe Phe
        195                 200                 205

Ser Gly Asp Lys Tyr Tyr Arg Val Asn Leu Arg Thr Arg Arg Val Asp
    210                 215                 220

Thr Val Asp Pro Pro Tyr Pro Arg Ser Ile Ala Gln Tyr Trp Leu Gly
225                 230                 235                 240

Cys Pro Ala Pro Gly His Leu
            245

<210> SEQ ID NO 15
```

```
<211> LENGTH: 88
<212> TYPE: PRT
<213> ORGANISM: Artificial Sequence
<220> FEATURE:
<223> OTHER INFORMATION: Synthetic peptide RCP-2

<400> SEQUENCE: 15

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Pro Arg Pro Ser Leu Ala Lys Lys
    50                  55                  60

Gln Arg Phe Arg His Arg Asn Arg Lys Gly Tyr Arg Ser Gln Arg Gly
65                  70                  75                  80

His Ser Arg Gly Arg Asn Gln Asn
                85

<210> SEQ ID NO 16
<211> LENGTH: 108
<212> TYPE: PRT
<213> ORGANISM: Artificial Sequence
<220> FEATURE:
<223> OTHER INFORMATION: Synthetic peptide RCP-3

<400> SEQUENCE: 16

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Gly Val Pro Gly Gln Val Asp Ala
    50                  55                  60

Ala Met Ala Gly Arg Ile Tyr Ile Ser Gly Met Ala Pro Arg Pro Ser
65                  70                  75                  80

Leu Ala Lys Lys Gln Arg Phe Arg His Arg Asn Arg Lys Gly Tyr Arg
                85                  90                  95

Ser Gln Arg Gly His Ser Arg Gly Arg Asn Gln Asn
            100                 105

<210> SEQ ID NO 17
<211> LENGTH: 118
<212> TYPE: PRT
<213> ORGANISM: Artificial Sequence
<220> FEATURE:
<223> OTHER INFORMATION: Synthetic peptide RCP-4

<400> SEQUENCE: 17

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Gln Pro Gln Phe Ile Ser Arg Asp
    50                  55                  60
```

Trp His Gly Val Pro Gly Gln Val Asp Ala Ala Met Ala Gly Arg Ile
65                  70                  75                  80

Tyr Ile Ser Gly Met Ala Pro Arg Pro Ser Leu Ala Lys Lys Gln Arg
                85                  90                  95

Phe Arg His Arg Asn Arg Lys Gly Tyr Arg Ser Gln Arg Gly His Ser
            100                 105                 110

Arg Gly Arg Asn Gln Asn
            115

<210> SEQ ID NO 18
<211> LENGTH: 128
<212> TYPE: PRT
<213> ORGANISM: Artificial Sequence
<220> FEATURE:
<223> OTHER INFORMATION: Synthetic peptide RCP-5

<400> SEQUENCE: 18

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Phe Gly Arg Thr Ser Ala Gly
    50                  55                  60

Thr Arg Gln Pro Gln Phe Ile Ser Arg Asp Trp His Gly Val Pro Gly
65                  70                  75                  80

Gln Val Asp Ala Ala Met Ala Gly Arg Ile Tyr Ile Ser Gly Met Ala
                85                  90                  95

Pro Arg Pro Ser Leu Ala Lys Lys Gln Arg Phe Arg His Arg Asn Arg
            100                 105                 110

Lys Gly Tyr Arg Ser Gln Arg Gly His Ser Arg Gly Arg Asn Gln Asn
        115                 120                 125

<210> SEQ ID NO 19
<211> LENGTH: 246
<212> TYPE: PRT
<213> ORGANISM: Artificial Sequence
<220> FEATURE:
<223> OTHER INFORMATION: Synthetic peptide RCP-6

<400> SEQUENCE: 19

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Ser Gln Glu Glu Ser Glu Gly Ser
    50                  55                  60

Ser Leu Ser Ala Val Phe Glu His Phe Ala Met Met Gln Arg Asp Ser
65                  70                  75                  80

Trp Glu Asp Ile Phe Glu Leu Leu Phe Trp Gly Arg Thr Ser Ala Gly
                85                  90                  95

Thr Arg Gln Pro Gln Phe Ile Ser Arg Asp Trp His Gly Val Pro Gly
            100                 105                 110

Gln Val Asp Ala Ala Met Ala Gly Arg Ile Tyr Ile Ser Gly Met Ala
        115                 120                 125

```
Pro Arg Pro Ser Leu Ala Lys Lys Gln Arg Phe Arg His Arg Asn Arg
    130                 135                 140

Lys Gly Tyr Arg Ser Gln Arg Gly His Ser Arg Gly Arg Asn Gln Asn
145                 150                 155                 160

Ser Arg Arg Pro Ser Arg Ala Thr Trp Leu Ser Leu Phe Ser Ser Glu
                165                 170                 175

Glu Ser Asn Leu Gly Ala Asn Asn Tyr Asp Asp Tyr Arg Met Asp Trp
            180                 185                 190

Leu Val Pro Ala Thr Ser Glu Pro Ile Gln Ser Val Phe Phe Ser
        195                 200                 205

Gly Asp Lys Tyr Tyr Arg Val Asn Leu Arg Thr Arg Val Asp Thr
    210                 215                 220

Val Asp Pro Pro Tyr Pro Arg Ser Ile Ala Gln Tyr Trp Leu Gly Ser
225                 230                 235                 240

Pro Ala Pro Gly His Leu
                245

<210> SEQ ID NO 20
<211> LENGTH: 160
<212> TYPE: PRT
<213> ORGANISM: Artificial Sequence
<220> FEATURE:
<223> OTHER INFORMATION: Synthetic peptide RCP-7

<400> SEQUENCE: 20

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
                20                  25                  30

Cys Thr Asp Tyr Thr Ala Glu Cys Lys Pro Gln Val Thr Arg Gly Asp
            35                  40                  45

Val Phe Thr Met Pro Glu Asp Glu Ser Gln Glu Glu Ser Glu Gly Ser
        50                  55                  60

Ser Leu Ser Ala Val Phe Glu His Phe Ala Met Met Gln Arg Asp Ser
65                  70                  75                  80

Trp Glu Asp Ile Phe Glu Leu Leu Phe Trp Gly Arg Thr Ser Ala Gly
                85                  90                  95

Thr Arg Gln Pro Gln Phe Ile Ser Arg Asp Trp His Gly Val Pro Gly
                100                 105                 110

Gln Val Asp Ala Ala Met Ala Gly Arg Ile Tyr Ile Ser Gly Met Ala
            115                 120                 125

Pro Arg Pro Ser Leu Ala Lys Lys Gln Arg Phe Arg His Arg Asn Arg
    130                 135                 140

Lys Gly Tyr Arg Ser Gln Arg Gly His Ser Arg Gly Arg Asn Gln Asn
145                 150                 155                 160

<210> SEQ ID NO 21
<211> LENGTH: 166
<212> TYPE: PRT
<213> ORGANISM: Artificial Sequence
<220> FEATURE:
<223> OTHER INFORMATION: Synthetic peptide RCP-8

<400> SEQUENCE: 21

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
```

```
                20                  25                  30
Cys Thr Asp Tyr Thr Ala Glu Cys Lys Pro Gln Val Thr Arg Gly Asp
            35                  40                  45

Val Phe Thr Met Pro Glu Asp Glu Ser Gln Glu Glu Ser Glu Gly Ser
 50                  55                  60

Ser Leu Ser Ala Val Phe Glu His Phe Ala Met Met Gln Arg Asp Ser
 65                  70                  75                  80

Trp Glu Asp Ile Phe Glu Leu Leu Phe Trp Gly Arg Thr Ser Ala Gly
                 85                  90                  95

Thr Arg Gln Pro Gln Phe Ile Ser Arg Asp Trp His Gly Val Pro Gly
            100                 105                 110

Gln Val Asp Ala Ala Met Ala Gly Arg Ile Tyr Ile Ser Gly Met Ala
            115                 120                 125

Pro Arg Pro Ser Leu Ala Lys Lys Gln Arg Phe Arg His Arg Asn Arg
            130                 135                 140

Lys Gly Tyr Arg Ser Gln Arg Gly His Ser Arg Gly Arg Asn Gln Asn
145                 150                 155                 160

Ser Arg Arg Pro Ser Arg
                165

<210> SEQ ID NO 22
<211> LENGTH: 176
<212> TYPE: PRT
<213> ORGANISM: Artificial Sequence
<220> FEATURE:
<223> OTHER INFORMATION: Synthetic peptide RCP-9

<400> SEQUENCE: 22

Met Asp Gln Glu Ser Cys Lys Gly Arg Cys Thr Glu Gly Phe Asn Val
 1               5                  10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
            35                  40                  45

Val Phe Thr Met Pro Glu Asp Glu Ser Gln Glu Glu Ser Glu Gly Ser
 50                  55                  60

Ser Leu Ser Ala Val Phe Glu His Phe Ala Met Met Gln Arg Asp Ser
 65                  70                  75                  80

Trp Glu Asp Ile Phe Glu Leu Leu Phe Trp Gly Arg Thr Ser Ala Gly
                 85                  90                  95

Thr Arg Gln Pro Gln Phe Ile Ser Arg Asp Trp His Gly Val Pro Gly
            100                 105                 110

Gln Val Asp Ala Ala Met Ala Gly Arg Ile Tyr Ile Ser Gly Met Ala
            115                 120                 125

Pro Arg Pro Ser Leu Ala Lys Lys Gln Arg Phe Arg His Arg Asn Arg
            130                 135                 140

Lys Gly Tyr Arg Ser Gln Arg Gly His Ser Arg Gly Arg Asn Gln Asn
145                 150                 155                 160

Ser Arg Arg Pro Ser Arg Ala Thr Trp Leu Ser Leu Phe Ser Ser Glu
                165                 170                 175

<210> SEQ ID NO 23
<211> LENGTH: 186
<212> TYPE: PRT
<213> ORGANISM: Artificial Sequence
<220> FEATURE:
<223> OTHER INFORMATION: Synthetic peptide RCP-10
```

<400> SEQUENCE: 23

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Ser Gln Glu Ser Glu Gly Ser
    50                  55                  60

Ser Leu Ser Ala Val Phe Glu His Phe Ala Met Met Gln Arg Asp Ser
65              70                  75                  80

Trp Glu Asp Ile Phe Glu Leu Leu Phe Trp Gly Arg Thr Ser Ala Gly
                85                  90                  95

Thr Arg Gln Pro Gln Phe Ile Ser Arg Asp Trp His Gly Val Pro Gly
            100                 105                 110

Gln Val Asp Ala Ala Met Ala Gly Arg Ile Tyr Ile Ser Gly Met Ala
        115                 120                 125

Pro Arg Pro Ser Leu Ala Lys Lys Gln Arg Phe Arg His Arg Asn Arg
    130                 135                 140

Lys Gly Tyr Arg Ser Gln Arg Gly His Ser Arg Gly Arg Asn Gln Asn
145             150                 155                 160

Ser Arg Arg Pro Ser Arg Ala Thr Trp Leu Ser Leu Phe Ser Ser Glu
            165                 170                 175

Glu Ser Asn Leu Gly Ala Asn Asn Tyr Asp
            180                 185

<210> SEQ ID NO 24
<211> LENGTH: 463
<212> TYPE: PRT
<213> ORGANISM: Artificial Sequence
<220> FEATURE:
<223> OTHER INFORMATION: Synthetic peptide RCP-11

<400> SEQUENCE: 24

Gly Pro Leu Gly Asp Gln Glu Ser Cys Lys Gly Arg Cys Thr Glu Gly
1               5                   10                  15

Phe Asn Val Asp Lys Lys Cys Gln Cys Asp Glu Leu Cys Ser Tyr Tyr
            20                  25                  30

Gln Ser Cys Cys Thr Asp Tyr Thr Ala Glu Cys Lys Pro Gln Val Thr
        35                  40                  45

Arg Gly Asp Val Phe Thr Met Pro Glu Asp Glu Tyr Thr Val Tyr Asp
    50                  55                  60

Asp Gly Glu Glu Lys Asn Asn Ala Thr Val His Glu Gln Val Gly Gly
65              70                  75                  80

Pro Ser Leu Thr Ser Asp Leu Gln Ala Gln Ser Lys Gly Asn Pro Glu
            85                  90                  95

Gln Thr Pro Val Leu Lys Pro Glu Glu Ala Pro Ala Pro Glu Val
            100                 105                 110

Gly Ala Ser Lys Pro Glu Gly Ile Asp Ser Arg Pro Glu Thr Leu His
        115                 120                 125

Pro Gly Arg Pro Gln Pro Pro Ala Glu Glu Leu Cys Ser Gly Lys
    130                 135                 140

Pro Phe Asp Ala Phe Thr Asp Leu Lys Asn Gly Ser Leu Phe Ala Phe
145             150                 155                 160

Arg Gly Gln Tyr Cys Tyr Glu Leu Asp Glu Lys Ala Val Arg Pro Gly
                165                 170                 175

Tyr Pro Lys Leu Ile Arg Asp Val Trp Gly Ile Glu Gly Pro Ile Asp
            180                 185                 190

Ala Ala Phe Thr Arg Ile Asn Cys Gln Gly Lys Thr Tyr Leu Phe Lys
            195                 200                 205

Gly Ser Gln Tyr Trp Arg Phe Glu Asp Gly Val Leu Asp Pro Asp Tyr
        210                 215                 220

Pro Arg Asn Ile Ser Asp Gly Phe Asp Gly Ile Pro Asp Asn Val Asp
225                 230                 235                 240

Ala Ala Leu Ala Leu Pro Ala His Ser Tyr Ser Gly Arg Glu Arg Val
                245                 250                 255

Tyr Phe Phe Lys Gly Lys Gln Tyr Trp Glu Tyr Gln Phe Gln His Gln
            260                 265                 270

Pro Ser Gln Glu Glu Cys Glu Gly Ser Ser Leu Ser Ala Val Phe Glu
        275                 280                 285

His Phe Ala Met Met Gln Arg Asp Ser Trp Glu Asp Ile Phe Glu Leu
        290                 295                 300

Leu Phe Trp Gly Arg Thr Ser Ala Gly Thr Arg Gln Pro Gln Phe Ile
305                 310                 315                 320

Ser Arg Asp Trp His Gly Val Pro Gly Gln Val Asp Ala Ala Met Ala
                325                 330                 335

Gly Arg Ile Tyr Ile Ser Gly Met Ala Pro Arg Pro Ser Leu Ala Lys
            340                 345                 350

Lys Gln Arg Phe Arg His Arg Asn Arg Lys Gly Tyr Arg Ser Gln Arg
            355                 360                 365

Gly His Ser Arg Gly Arg Asn Gln Asn Ser Arg Arg Pro Ser Arg Ala
        370                 375                 380

Thr Trp Leu Ser Leu Phe Ser Ser Glu Glu Ser Asn Leu Gly Ala Asn
385                 390                 395                 400

Asn Tyr Asp Asp Tyr Arg Met Asp Trp Leu Val Pro Ala Thr Cys Glu
                405                 410                 415

Pro Ile Gln Ser Val Phe Phe Phe Ser Gly Asp Lys Tyr Tyr Arg Val
            420                 425                 430

Asn Leu Arg Thr Arg Arg Val Asp Thr Val Asp Pro Pro Tyr Pro Arg
            435                 440                 445

Ser Ile Ala Gln Tyr Trp Leu Gly Cys Pro Ala Pro Gly His Leu
        450                 455                 460

<210> SEQ ID NO 25
<211> LENGTH: 272
<212> TYPE: PRT
<213> ORGANISM: Artificial Sequence
<220> FEATURE:
<223> OTHER INFORMATION: Synthetic peptide RCP-12

<400> SEQUENCE: 25

Gly Pro Leu Gly Asp Gln Glu Ser Cys Lys Gly Arg Cys Thr Glu Gly
1               5                   10                  15

Phe Asn Val Asp Lys Lys Cys Gln Cys Asp Glu Leu Cys Ser Tyr Tyr
            20                  25                  30

Gln Ser Cys Cys Thr Asp Tyr Thr Ala Glu Cys Lys Pro Gln Val Thr
        35                  40                  45

Arg Gly Asp Val Phe Thr Met Pro Glu Asp Glu Tyr Thr Val Tyr Asp
    50                  55                  60

```
Asp Gly Glu Glu Lys Asn Asn Ala Thr Val His Glu Gln Val Gly Gly
 65                  70                  75                  80

Pro Ser Leu Thr Ser Asp Leu Gln Ala Gln Ser Lys Gly Asn Pro Glu
                 85                  90                  95

Gln Thr Pro Val Leu Lys Pro Glu Glu Ala Pro Ala Pro Glu Val
            100                 105                 110

Gly Ala Ser Lys Pro Glu Gly Ile Asp Ser Arg Pro Glu Thr Leu His
            115                 120                 125

Pro Gly Arg Pro Gln Pro Ala Glu Glu Leu Cys Ser Gly Lys
        130                 135                 140

Pro Phe Asp Ala Phe Thr Asp Leu Lys Asn Gly Ser Leu Phe Ala Phe
145                 150                 155                 160

Arg Gly Gln Tyr Cys Tyr Glu Leu Asp Glu Lys Ala Val Arg Pro Gly
                165                 170                 175

Tyr Pro Lys Leu Ile Arg Asp Val Trp Gly Ile Glu Gly Pro Ile Asp
            180                 185                 190

Ala Ala Phe Thr Arg Ile Asn Cys Gln Gly Lys Thr Tyr Leu Phe Lys
        195                 200                 205

Gly Ser Gln Tyr Trp Arg Phe Glu Asp Gly Val Leu Asp Pro Asp Tyr
    210                 215                 220

Pro Arg Asn Ile Ser Asp Gly Phe Asp Gly Ile Pro Asp Asn Val Asp
225                 230                 235                 240

Ala Ala Leu Ala Leu Pro Ala His Ser Tyr Ser Gly Arg Glu Arg Val
                245                 250                 255

Tyr Phe Phe Lys Gly Lys Gln Tyr Trp Glu Tyr Gln Phe Gln His Gln
            260                 265                 270

<210> SEQ ID NO 26
<211> LENGTH: 134
<212> TYPE: PRT
<213> ORGANISM: Artificial Sequence
<220> FEATURE:
<223> OTHER INFORMATION: Synthetic peptide RCP-13

<400> SEQUENCE: 26

Gly Pro Leu Gly Asp Gln Glu Ser Cys Lys Arg Cys Thr Glu Gly
 1               5                  10                  15

Phe Asn Val Asp Lys Lys Cys Gln Cys Asp Glu Leu Cys Ser Tyr Tyr
                 20                  25                  30

Gln Ser Cys Cys Thr Asp Tyr Thr Ala Glu Cys Lys Pro Gln Val Thr
            35                  40                  45

Arg Gly Asp Val Phe Thr Met Pro Glu Asp Glu Tyr Thr Val Tyr Asp
    50                  55                  60

Asp Gly Glu Glu Lys Asn Asn Ala Thr Val His Glu Gln Val Gly Gly
 65                  70                  75                  80

Pro Ser Leu Thr Ser Asp Leu Gln Ala Gln Ser Lys Gly Asn Pro Glu
                 85                  90                  95

Gln Thr Pro Val Leu Lys Pro Glu Glu Ala Pro Ala Pro Glu Val
            100                 105                 110

Gly Ala Ser Lys Pro Glu Gly Ile Asp Ser Arg Pro Glu Thr Leu His
            115                 120                 125

Pro Gly Arg Pro Gln Pro
        130

<210> SEQ ID NO 27
<211> LENGTH: 59
```

<212> TYPE: PRT
<213> ORGANISM: Artificial Sequence
<220> FEATURE:
<223> OTHER INFORMATION: Synthetic peptide RCP-14

<400> SEQUENCE: 27

Gly Pro Leu Gly Asp Gln Glu Ser Cys Lys Gly Arg Cys Thr Glu Gly
1               5                   10                  15

Phe Asn Val Asp Lys Lys Cys Gln Cys Asp Glu Leu Cys Ser Tyr Tyr
            20                  25                  30

Gln Ser Cys Cys Thr Asp Tyr Thr Ala Glu Cys Lys Pro Gln Val Thr
        35                  40                  45

Arg Gly Asp Val Phe Thr Met Pro Glu Asp Glu
    50                  55

<210> SEQ ID NO 28
<211> LENGTH: 408
<212> TYPE: PRT
<213> ORGANISM: Artificial Sequence
<220> FEATURE:
<223> OTHER INFORMATION: Synthetic peptide RCP-15

<400> SEQUENCE: 28

Gly Pro Leu Gly Tyr Thr Val Tyr Asp Asp Gly Glu Glu Lys Asn Asn
1               5                   10                  15

Ala Thr Val His Glu Gln Val Gly Gly Pro Ser Leu Thr Ser Asp Leu
            20                  25                  30

Gln Ala Gln Ser Lys Gly Asn Pro Glu Gln Thr Pro Val Leu Lys Pro
        35                  40                  45

Glu Glu Glu Ala Pro Ala Pro Glu Val Gly Ala Ser Lys Pro Glu Gly
    50                  55                  60

Ile Asp Ser Arg Pro Glu Thr Leu His Pro Gly Arg Pro Gln Pro Pro
65                  70                  75                  80

Ala Glu Glu Glu Leu Cys Ser Gly Lys Pro Phe Asp Ala Phe Thr Asp
            85                  90                  95

Leu Lys Asn Gly Ser Leu Phe Ala Phe Arg Gly Gln Tyr Cys Tyr Glu
            100                 105                 110

Leu Asp Glu Lys Ala Val Arg Pro Gly Tyr Pro Lys Leu Ile Arg Asp
        115                 120                 125

Val Trp Gly Ile Glu Gly Pro Ile Asp Ala Ala Phe Thr Arg Ile Asn
    130                 135                 140

Cys Gln Gly Lys Thr Tyr Leu Phe Lys Gly Ser Gln Tyr Trp Arg Phe
145                 150                 155                 160

Glu Asp Gly Val Leu Asp Pro Asp Tyr Pro Arg Asn Ile Ser Asp Gly
            165                 170                 175

Phe Asp Gly Ile Pro Asp Asn Val Asp Ala Ala Leu Ala Leu Pro Ala
            180                 185                 190

His Ser Tyr Ser Gly Arg Glu Arg Val Tyr Phe Phe Lys Gly Lys Gln
        195                 200                 205

Tyr Trp Glu Tyr Gln Phe Gln His Gln Pro Ser Gln Glu Glu Cys Glu
    210                 215                 220

Gly Ser Ser Leu Ser Ala Val Phe Glu His Phe Ala Met Met Gln Arg
225                 230                 235                 240

Asp Ser Trp Glu Asp Ile Phe Glu Leu Leu Phe Trp Gly Arg Thr Ser
            245                 250                 255

Ala Gly Thr Arg Gln Pro Gln Phe Ile Ser Arg Asp Trp His Gly Val
            260                 265                 270

```
Pro Gly Gln Val Asp Ala Ala Met Ala Gly Arg Ile Tyr Ile Ser Gly
            275                 280                 285

Met Ala Pro Arg Pro Ser Leu Ala Lys Lys Gln Arg Phe Arg His Arg
        290                 295                 300

Asn Arg Lys Gly Tyr Arg Ser Gln Arg Gly His Ser Arg Gly Arg Asn
305                 310                 315                 320

Gln Asn Ser Arg Arg Pro Ser Arg Ala Thr Trp Leu Ser Leu Phe Ser
                325                 330                 335

Ser Glu Glu Ser Asn Leu Gly Ala Asn Asn Tyr Asp Asp Tyr Arg Met
                340                 345                 350

Asp Trp Leu Val Pro Ala Thr Cys Glu Pro Ile Gln Ser Val Phe Phe
            355                 360                 365

Phe Ser Gly Asp Lys Tyr Tyr Arg Val Asn Leu Arg Thr Arg Arg Val
        370                 375                 380

Asp Thr Val Asp Pro Tyr Pro Arg Ser Ile Ala Gln Tyr Trp Leu
385                 390                 395                 400

Gly Cys Pro Ala Pro Gly His Leu
                405

<210> SEQ ID NO 29
<211> LENGTH: 195
<212> TYPE: PRT
<213> ORGANISM: Artificial Sequence
<220> FEATURE:
<223> OTHER INFORMATION: Synthetic peptide RCP-16

<400> SEQUENCE: 29

Gly Pro Leu Gly Pro Ser Gln Glu Glu Cys Glu Gly Ser Ser Leu Ser
1               5                   10                  15

Ala Val Phe Glu His Phe Ala Met Met Gln Arg Asp Ser Trp Glu Asp
                20                  25                  30

Ile Phe Glu Leu Leu Phe Trp Gly Arg Thr Ser Ala Gly Thr Arg Gln
            35                  40                  45

Pro Gln Phe Ile Ser Arg Asp Trp His Gly Val Pro Gly Gln Val Asp
    50                  55                  60

Ala Ala Met Ala Gly Arg Ile Tyr Ile Ser Gly Met Ala Pro Arg Pro
65                  70                  75                  80

Ser Leu Ala Lys Lys Gln Arg Phe Arg His Arg Asn Arg Lys Gly Tyr
                85                  90                  95

Arg Ser Gln Arg Gly His Ser Arg Gly Arg Asn Gln Asn Ser Arg Arg
                100                 105                 110

Pro Ser Arg Ala Thr Trp Leu Ser Leu Phe Ser Ser Glu Glu Ser Asn
            115                 120                 125

Leu Gly Ala Asn Asn Tyr Asp Asp Tyr Arg Met Asp Trp Leu Val Pro
    130                 135                 140

Ala Thr Cys Glu Pro Ile Gln Ser Val Phe Phe Ser Gly Asp Lys
145                 150                 155                 160

Tyr Tyr Arg Val Asn Leu Arg Thr Arg Arg Val Asp Thr Val Asp Pro
                165                 170                 175

Pro Tyr Pro Arg Ser Ile Ala Gln Tyr Trp Leu Gly Cys Pro Ala Pro
                180                 185                 190

Gly His Leu
        195

<210> SEQ ID NO 30
```

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 30

Asp Gln Glu Ser Cys Lys Gly Arg Cys Thr Glu Gly Phe Asn Val Asp
1               5                   10                  15

Lys Lys Cys Gln
            20

<210> SEQ ID NO 31
<211> LENGTH: 20
<212> TYPE: PRT
<213> ORGANISM: Artificial Sequence
<220> FEATURE:
<223> OTHER INFORMATION: Synthetic peptide

<400> SEQUENCE: 31

Lys Gly Arg Cys Thr Glu Gly Phe Asn Val Asp Lys Lys Cys Gln Cys
1               5                   10                  15

Asp Glu Leu Cys
            20

<210> SEQ ID NO 32
<211> LENGTH: 20
<212> TYPE: PRT
<213> ORGANISM: Artificial Sequence
<220> FEATURE:
<223> OTHER INFORMATION: Synthetic peptide

<400> SEQUENCE: 32

Glu Gly Phe Asn Val Asp Lys Lys Cys Gln Cys Asp Glu Leu Cys Ser
1               5                   10                  15

Tyr Tyr Gln Ser
            20

<210> SEQ ID NO 33
<211> LENGTH: 20
<212> TYPE: PRT
<213> ORGANISM: Artificial Sequence
<220> FEATURE:
<223> OTHER INFORMATION: Synthetic peptide

<400> SEQUENCE: 33

Asp Lys Lys Cys Gln Cys Asp Glu Leu Cys Ser Tyr Tyr Gln Ser Cys
1               5                   10                  15

Cys Thr Asp Tyr
            20

<210> SEQ ID NO 34
<211> LENGTH: 20
<212> TYPE: PRT
<213> ORGANISM: Artificial Sequence
<220> FEATURE:
<223> OTHER INFORMATION: Synthetic peptide

<400> SEQUENCE: 34

Cys Cys Thr Asp Tyr Thr Ala Glu Cys Lys Pro Gln Val Thr Arg Gly
1               5                   10                  15

Asp Val Phe Thr
            20
```

```
<210> SEQ ID NO 35
<211> LENGTH: 20
<212> TYPE: PRT
<213> ORGANISM: Artificial Sequence
<220> FEATURE:
<223> OTHER INFORMATION: Synthetic peptide

<400> SEQUENCE: 35

Thr Ala Glu Cys Lys Pro Gln Val Thr Arg Gly Asp Val Phe Thr Met
1               5                   10                  15

Pro Glu Asp Glu
            20

<210> SEQ ID NO 36
<211> LENGTH: 20
<212> TYPE: PRT
<213> ORGANISM: Artificial Sequence
<220> FEATURE:
<223> OTHER INFORMATION: Synthetic peptide

<400> SEQUENCE: 36

Cys Cys Thr Asp Tyr Thr Ala Glu Cys Lys Pro Gln Val Thr Arg Gly
1               5                   10                  15

Glu Val Phe Thr
            20

<210> SEQ ID NO 37
<211> LENGTH: 20
<212> TYPE: PRT
<213> ORGANISM: Artificial Sequence
<220> FEATURE:
<223> OTHER INFORMATION: Synthetic peptide

<400> SEQUENCE: 37

Thr Ala Glu Cys Lys Pro Gln Val Thr Arg Gly Glu Val Phe Thr Met
1               5                   10                  15

Pro Glu Asp Glu
            20

<210> SEQ ID NO 38
<211> LENGTH: 142
<212> TYPE: PRT
<213> ORGANISM: Artificial Sequence
<220> FEATURE:
<223> OTHER INFORMATION: Synthetic peptide RCP-17aa

<400> SEQUENCE: 38

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Ser Gln Glu Ser Glu Gly Ser Glu
    50                  55                  60

Asp Ile Phe Glu Leu Leu Phe Trp Gly Arg Thr Ser Ala Gly Thr Arg
65                  70                  75                  80

Gln Pro Gln Phe Ile Ser Arg Asp Trp His Gly Val Pro Gly Gln Val
                85                  90                  95

Asp Ala Ala Met Ala Gly Arg Ile Tyr Ile Ser Gly Met Ala Pro Arg
            100                 105                 110

Pro Ser Leu Ala Lys Lys Gln Arg Phe Arg His Arg Asn Arg Lys Gly
```

```
            115                 120                 125
Tyr Arg Ser Gln Arg Gly His Ser Arg Gly Arg Asn Gln Asn
        130                 135                 140

<210> SEQ ID NO 39
<211> LENGTH: 143
<212> TYPE: PRT
<213> ORGANISM: Artificial Sequence
<220> FEATURE:
<223> OTHER INFORMATION: Synthetic peptide RCP-17

<400> SEQUENCE: 39

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Ser Gln Glu Glu Ser Glu Gly Ser
    50                  55                  60

Glu Asp Ile Phe Glu Leu Leu Phe Trp Gly Arg Thr Ser Ala Gly Thr
65                  70                  75                  80

Arg Gln Pro Gln Phe Ile Ser Arg Asp Trp His Gly Val Pro Gly Gln
                85                  90                  95

Val Asp Ala Ala Met Ala Gly Arg Ile Tyr Ile Ser Gly Met Ala Pro
            100                 105                 110

Arg Pro Ser Leu Ala Lys Lys Gln Arg Phe Arg His Arg Asn Arg Lys
        115                 120                 125

Gly Tyr Arg Ser Gln Arg Gly His Ser Arg Gly Arg Asn Gln Asn
    130                 135                 140

<210> SEQ ID NO 40
<211> LENGTH: 4
<212> TYPE: PRT
<213> ORGANISM: Artificial Sequence
<220> FEATURE:
<223> OTHER INFORMATION: Synthetic peptide

<400> SEQUENCE: 40

Gly Gly Gly Ser
1

<210> SEQ ID NO 41
<211> LENGTH: 5
<212> TYPE: PRT
<213> ORGANISM: Artificial Sequence
<220> FEATURE:
<223> OTHER INFORMATION: Synthetic peptide

<400> SEQUENCE: 41

Gly Gly Gly Gly Ser
1               5

<210> SEQ ID NO 42
<211> LENGTH: 6
<212> TYPE: PRT
<213> ORGANISM: Artificial Sequence
<220> FEATURE:
```

```
<223> OTHER INFORMATION: Synthetic peptide

<400> SEQUENCE: 42

Gly Gly Gly Gly Gly Ser
1               5
```

POLYPEPTIDE COMPOSITION AND CULTURE METHOD FOR PLURIPOTENT STEM CELL USING SAME

CROSS-REFERENCE TO RELATED APPLICATIONS

This application is a continuation application of International Application No. PCT/JP2014/078813, filed Oct. 29, 2014, the disclosure of which is incorporated herein by reference in its entirety. Further, this application claims priority from Japanese Patent Application No. 2013-227583, filed Oct. 31, 2013, the disclosure of which is incorporated herein by reference in its entirety.

BACKGROUND OF THE INVENTION

1. Field of the Invention

The present invention relates to a polypeptide composition and a culture method for pluripotent stem cells using the polypeptide composition.

2. Description of the Related Art

For the purpose of the recovery of functions of damaged tissues, various regenerative medical techniques are being developed. Among these, a large number of techniques relating to totipotent or pluripotent stem cells of primates, particularly, human beings that is ultimately aimed at the regeneration of tissues has been reported. Especially, induced pluripotent stem cells (iPS cells) have an advantage in that these cells lessen ethical issues because they are induced from somatic cells unlike embryonic stem cells.

In a case where the totipotent or pluripotent stem cells (both will be collectively simply referred to as "pluripotent stem cells" in the present invention) of primates are cultured, the pluripotent stem cells need to be kept undifferentiated over a long period of time. For culturing the undifferentiated pluripotent stem cells over a long period of time, generally, feeder cells such as mouse fibroblasts are used.

However, it has been pointed out that the use of heterogeneous animal-derived feeder cells such as mouse fibroblasts leads to a likelihood that foreign substances such as heterogeneous animal-derived antigenic substances may be mixed into the culture solution. Therefore, in a case where the totipotent or pluripotent stem cells are used for medical purposes or for the purposes equivalent to medical purposes, the cells need to be cultured in the absence of feeder cells.

In consideration of the circumstances described above, cell-adhesive materials functioning as the feeder cells are being developed. For example, Nature Biotechnology, 2001, Vol. 19, pp. 971-974 discloses that human embryonic stem cells kept undifferentiated are successfully cultured by using matrix gel which is a component extracted from mouse sarcoma as a substituent for feeder cells.

JP2001-17183A discloses a feeder cell-free cellular composition containing growing primordial cells of primates, and discloses, as a preferred embodiment, a cellular composition further containing an extracelluar matrix. JP2010-29186A discloses a cell culture substrate in which a plasma-polymerized cell culture surface is coated with a coating solution containing an extracellular matrix protein at a predetermined concentration and an aqueous solvent. JP2010-29186A describes that the cell culture substrate has excellent adhesiveness helpful to avoid the differentiation of embryonic stem cells.

Biomaterials, 2010, November; Vol. 31(32), pp. 8281-8288 and Nature biotechnology, 2010, Vol. 28, No. 6, pp. 606-610 disclose a recombinant peptide or a synthetic peptide including a partial sequence of vitronectin that makes a contribution to long-term culture of embryonic stem cells. Specifically, the above documents disclose a polypeptide as an amino acid sequence consisting of the $1^{st}$ to $52^{nd}$ amino acids in the amino acid sequence of natural vitronectin (see Biomaterials, 2010, November; Vol. 31(32), pp. 8281-8288) and a polypeptide as an amion acid sequence consisting of the $40^{st}$ to $52^{nd}$ amino acids of natural vitronectin including an RGD sequence (see Nature biotechnology, 2010, Vol. 28, No. 6, pp. 606-610) respectively. It is known that these polypeptides make it possible to avoid a likelihood of intermixing of antigenic substances because they are non-biological samples and can be excellently produced in an industrial manner.

SUMMARY OF THE INVENTION

However, considering a case where the pluripotent stem cells are used for medical purposes such as regenerative medicine or for the purposes equivalent to medical purposes, the use of heterogeneous feeder cells such as fibroblasts derived from a mouse and the like or heterogeneous animal-derived components including mouse-derived Matrigel should be avoided as much as possible. Furthermore, even in a case of cells or components derived from a homogeneous animal, a likelihood of intermixing of an antigenic substance cannot be completely ruled out. In addition, whether they are homogeneous or heterogeneous, the materials derived from a biological body are not preferable from industrial viewpoints because the amount thereof extracted is extremely small or the property thereof varies with the donor. In recent years, with the aim of using pluripotent stem cells for medical purposes, the culture of the stem cells under chemically identified conditions that do not allow the intermixing of a heterogeneous animal-derived component or an antigenic substance has been actively investigated. However, materials that exhibit cell culturing property sufficient for practical use and can replace feeder cells have not yet been discovered.

For example, as means for avoiding the use of the material derived from a biological body, Biomaterials, 2010, November; Vol. 31(32), pp. 8281-8288 and Nature Biotechnology, 2010, Vol. 28, No. 6, pp. 606-610, disclose an example in which long-term culture of embryonic stem cells is performed using a recombinant peptide composed of a partial sequence of human vitronectin or using a synthetic peptide.

However, it cannot be said that such a recombinant peptide has a sufficient pluripotent stem cell culturing property.

The present invention can provide a polypeptide composition which can induce a pluripotent stem cell culturing property, particularly, an excellent cell growth ability, and a culture method for pluripotent stem cells using the polypeptide composition.

The present invention is as follows.

[1] A polypeptide composition comprising at least one selected from the group consisting of the following polypeptides (a) to (c):
(a) a polypeptide comprising an amino acid sequence represented by SEQ ID NO: 1,
(b) a polypeptide comprising an amino acid sequence which has identity of equal to or higher than 80% with the amino acid sequence represented by SEQ ID NO: 1, and having a pluripotent stem cell culturing property, and
(c) a polypeptide comprising an amino acid sequence, which is formed by deletion, substitution, or addition of one amino acid or plural amino acids in SEQ ID NO: 1, and having a pluripotent stem cell culturing property, each of the polypeptides (a) to (c) being a polypeptide including a first region represented by any one of the following amino acid sequences (1-i) to (1-iii):

(1-i) an amino acid sequence consisting of the 1st to 44th amino acid residues of the amino acid sequence represented by SEQ ID NO: 1, (1-ii) an amino acid sequence consisting of an amino acid sequence which has identity of equal to or higher than 80% with an amino acid sequence including the amino acid sequence (1-i), and having a cell adhesion ability with respect to pluripotent stem cells, and (1-iii) an amino acid sequence consisting of an amino acid sequence that is formed by deletion, substitution, or addition of one amino acid or plural amino acids in the amino acid sequence (1-i), and having a cell adhesion ability with respect to pluripotent stem cells, and an amount of a multimeric polypeptide, which is at least one selected from the group consisting of the polypeptides (a) to (c) and is composed of two or more monomers held together by intermolecular cross-linking via cysteine residues included in the first region, is equal to or less than 20% by mass of a total mass of polypeptides contained in the composition.

[2] A polypeptide composition comprising a polypeptide (d) consisting of 40 to 450 amino acid residues, the polypeptide (d) comprising a first region and a second region, the first region being represented by any one of the following amino acid sequences (1-i) to (1-iii):

(1-i) an amino acid sequence consisting of the 1st to 44th amino acid residues of an amino acid sequence represented by SEQ ID NO: 1, (1-ii) an amino acid sequence consisting of an amino acid sequence that has identity of equal to or higher than 80% with an amino acid sequence including the amino acid sequence (1-i), and having a cell adhesion ability with respect to pluripotent stem cells, and (1-iii) an amino acid sequence consisting of an amino acid sequence that is formed by deletion, substitution, or addition of one amino acid or plural amino acids in the amino acid sequence (1-i), and having a cell adhesion ability with respect to pluripotent stem cells, the second region being represented by any one of the following amino acid sequences (2-i) to (2-iii):

(2-i) an amino acid sequence represented by PRPSLAKKQRFRHRNRKGYRSQRGHSRGRNQN (SEQ ID NO: 3), (2-ii) an amino acid sequence which has identity of equal to or higher than 80% with the amino acid sequence represented by SEQ ID NO: 3, and has adsorbability with respect to a cell culture surface of a support, and (2-iii) an amino acid sequence that is formed by deletion, substitution, or addition of one amino acid or plural amino acids in the amino acid sequence represented by SEQ ID NO: 3, and has adsorbability with respect to a cell culture surface of a support, and an amount of a multimeric polypeptide, which is the polypeptide (d) and composed of two or more monomers held together by intermolecular cross-linking via cysteine residues included in the first region, being equal to or less than 20% by mass of a total mass of polypeptides contained in the composition.

[3] The polypeptide composition described in [1] or [2], wherein an amount of a multimeric polypeptide composed of two or more monomers held together by intermolecular cross-linking via cysteine residues in any positions in the polypeptide is equal to or less than 20% by mass of the total mass of polypeptides contained in the composition.

[4] The polypeptide composition described in any one of [1] to [3], wherein the polypeptides (a) to (c) include, or the polypeptide (d) includes at least one polypeptide in which intramolecular cross-linking is established between a cysteine residue corresponding to the 25th amino acid residue of the amino acid sequence represented by SEQ ID NO: 1 and included in the first region and a cysteine residue corresponding to the 31st amino acid residue of the same amino acid sequence.

[5] The polypeptide composition described in any one of [1] to [3], wherein the polypeptides (a) to (c) include, or the polypeptide (d) includes a polypeptide in which intramolecular cross-linking is established:

between a cysteine residue corresponding to the 5th amino acid residue of the amino acid sequence represented by SEQ ID NO: 1 and included in the first region and a cysteine residue corresponding to the 9th amino acid residue of the same amino acid sequence;

between a cysteine residue corresponding to the 19th amino acid residue and of the amino acid sequence represented by SEQ ID NO: 1 and included in the first region a cysteine residue corresponding to the 21st amino acid residue of the same amino acid sequence;

between a cysteine residue corresponding to the 25th amino acid residue of the amino acid sequence represented by SEQ ID NO: 1 and included in the first region and a cysteine residue corresponding to the 31st amino acid residue of the same amino acid sequence; and between a cysteine residue corresponding to the 32nd amino acid residue of the amino acid sequence represented by SEQ ID NO: 1 and included in the first region and a cysteine residue corresponding to the 39th amino acid residue of the same amino acid sequence.

[6] The polypeptide composition described in any one of [1] to [3], wherein a binding constant between the polypeptide contained in the composition and a plasminogen activator inhibitor-1 is greater than 0.06.

[7] The polypeptide composition described in any one of [1] to [6], further comprising, as the polypeptides (a) to (c) or the polypeptide (d), at least one polypeptide that further includes a third region containing any one of the following amino acid sequences (3a-i) to (3a-iii):

(3a-i) an amino acid sequence that consists of the 56th to 341st amino acid residues of the amino acid sequence represented by SEQ ID NO: 1, or a partial amino acid sequence of the amino acid sequence represented by SEQ ID NO: 1, (3a-ii) an amino acid sequence having identity of equal to or higher than 80% with the amino acid sequence (3a-i) or the partial amino acid sequence of the amino acid sequence (3a-i), and (3a-iii) an amino acid sequence formed by deletion, substitution, or addition of one amino acid or plural amino acids in the amino acid sequence (3a-i) or the partial amino acid sequence of the amino acid sequence (3a-i).

[8] The polypeptide composition described in any one of [1] to [7], further comprising, as the polypeptides (a) to (c) or the polypeptide (d), at least one polypeptide that includes a fourth region containing any one of the following amino acid sequences (4a-i) to (4a-iii):

(4a-i) an amino acid sequence that consists of the 374th to 459th amino acid residues of the amino acid sequence represented by SEQ ID NO: 1, or a partial amino acid sequence of the amino acid sequence represented by SEQ ID NO: 1, (4a-ii) an amino acid sequence having identity of equal to or higher than 80% with the amino acid sequence (4a-i) or the partial amino acid sequence of the amino acid sequence (4a-i), and (4a-iii) an amino acid sequence formed by deletion, substitution, or addition of one amino acid or plural amino acids in the amino acid sequence (4a-i) or the partial amino acid sequence of the amino acid sequence (4a-i).

[9] A polypeptide composition comprising at least one polypeptide selected from the group consisting of the following polypeptides (a) to (c):

(a) a polypeptide having an amino acid sequence represented by SEQ ID NO: 1, (b) a polypeptide having an amino acid sequence which has identity of equal to or higher than 80% with the amino acid sequence represented by SEQ ID NO: 1, and having a pluripotent stem cell culturing property, and (c) a polypeptide having an amino acid sequence which is formed by deletion, substitution, or addition of one amino acid or plural amino acids in SEQ ID NO: 1, and having a pluripotent stem cell culturing property, an amount of a multimeric polypeptide that is composed of two or more monomers held together by intermolecular cross-linking via cysteine residues included in the polypeptide being equal to or less than 20% by mass of a total mass of polypeptides contained in the composition.

[10] A culture method for pluripotent stem cells, comprising culturing pluripotent stem cells in the presence of the polypeptide composition according to any one of [1] to [9].

[11] A culture vessel comprising:
a support having a cell culture surface; and
the polypeptide contained in the polypeptide composition according to any one of [1] to [9], which is disposed on the cell culture surface of the support.

According to the present invention, it is possible to provide a polypeptide composition, which can induce a pluripotent stem cell culturing property, particularly, an excellent cell growth ability, and to provide a culture method for pluripotent stem cells using the polypeptide composition.

BRIEF DESCRIPTION OF THE DRAWINGS

FIG. 5 is an image of gel of SDS-PAGE of polypeptide compositions I-1 (on the right side), according to examples of the present invention.

DESCRIPTION OF THE PREFERRED EMBODIMENTS

Figure 1:
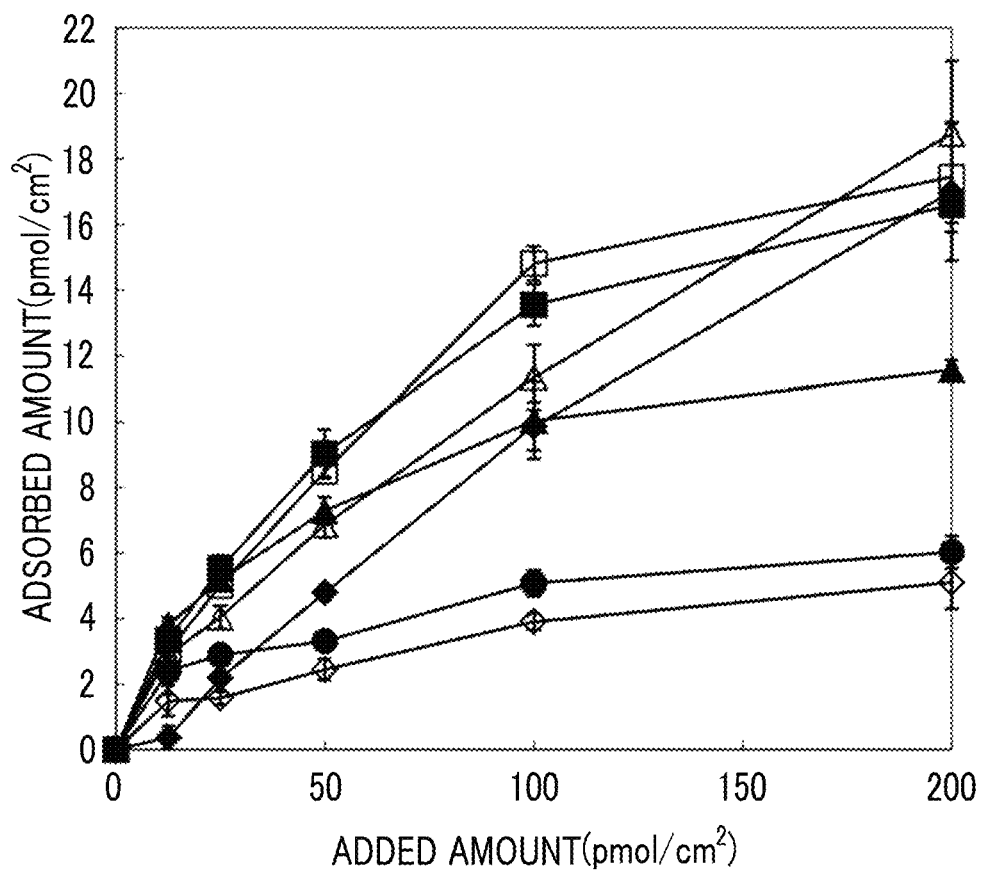
FIG. 1 is a graph showing the results of a test performed to check how well each polypeptide in reference examples of the present invention is adsorbed onto the surface of a culture plate.

A polypeptide composition of the present invention contains at least one selected from the group consisting of the following polypeptides (a) to (c): (a) a polypeptide having an amino acid sequence represented by SEQ ID NO: 1, (b) a polypeptide having an amino acid sequence which has identity of equal to or higher than 80% with the amino acid sequence represented by SEQ ID NO: 1, and having a pluripotent stem cell culturing property, and (c) a polypeptide having an amino acid sequence, which is formed by deletion, substitution, or addition of one amino acid or plural amino acids in SEQ ID NO: 1, and having a pluripotent stem cell culturing property, in which each of the polypeptides (a) to (c) is a polypeptide having a first region represented by any one of the following amino acid sequences (1-i) to (1-iii): (1-i) an amino acid sequence consisting of the $1^{st}$ to $44^{th}$ amino acid residues in the amino acid sequence represented by SEQ ID NO: 1, (1-ii) an amino acid sequence consisting of an amino acid sequence which has identity of equal to or higher than 80% with an amino acid sequence including the amino acid sequence (1-i), and having a cell adhesion ability with respect to pluripotent stem cells, and (1-iii) an amino acid sequence consisting of an amino acid sequence which is formed by deletion, substitution, or addition of one amino acid or plural amino acids in the amino acid sequence (1-i), and having a cell adhesion ability with respect to pluripotent stem cells, and an amount of a multimeric polypeptide, which is at least one selected from the group consisting of the polypeptides (a) to (c) and is composed of two or more monomers held together by intermolecular cross-linking via cysteine residues included in the first region, is equal to or less than 20% by mass of a total mass of polypeptides contained in the composition.

Furthermore, another polypeptide composition of the present invention contains a polypeptide (d) consisting of 40 to 450 amino acid residues, in which the polypeptide (d) is a polypeptide including a first region and a second region, the first region is represented by any one of the following amino acid sequences (1-i) to (1-iii): (1-i) an amino acid sequence consisting of the $1^{st}$ to $44^{th}$ amino acid residues in an amino acid sequence represented by SEQ ID NO: 1, (1-ii) an amino acid sequence including an amino acid sequence which has identity of equal to or higher than 80% with an amino acid sequence including the amino acid sequence (1-i), and having a cell adhesion ability with respect to pluripotent stem cells, and (1-iii) an amino acid sequence including an amino acid sequence which is formed by deletion, substitution, or addition of one amino acid or plural amino acids in the amino acid sequence (1-i), and having a cell adhesion ability with respect to pluripotent stem cells, and a second region is represented by any one of the following amino acid sequences (2-i) to (2-iii): (2-i) an amino acid sequence represented by PRPSLAKKQR-FRHRNRKGYRSQRGHSRGRNQN (SEQ ID NO: 3), (2-ii) an amino acid sequence which has identity of equal to or higher than 80% with the amino acid sequence represented by SEQ ID NO: 3 and has adsorbability with respect to a cell culture surface of a support, and (2-iii) an amino acid sequence which is formed by deletion, substitution, or addition of one amino acid or plural amino acids in the amino acid sequence represented by SEQ ID NO: 3 and has adsorbability with respect to a cell culture surface of a support, and an amount of a multimeric polypeptide, which is the polypeptide (d) and composed of two or more monomers held together by intermolecular cross-linking via cysteine residues included in the first region, is equal to or less than 20% by mass of a total mass of polypeptides contained in the composition.

In order to develop a recombinant protein that enables the growth of pluripotent stem cells, the inventors of the present invention repeated intensive research. As a result, they obtained knowledge that by culturing pluripotent stem cells in the presence of a polypeptide composition containing a large amount of polypeptide, which has an amino acid sequence including a partial sequence of the N-terminal side of a predetermined human vitronectin and having a cell adhesion ability with respect to pluripotent stem cells, not in the form of a multimer composed of two or more monomers held together by intermolecular cross-linking via cysteine residues on the N-terminal side of the human vitronectin but in the form of a monomer in which intermolecular cross-linking is not established, the growth ability of the pluripotent stem cells is improved. The present invention is based on the knowledge.

Hereinafter, embodiments of the present invention will be specifically described.

The polypeptide composition of the present invention is a composition containing at least one kind of polypeptide selected from the group consisting of the polypeptides (a) to (c) described above, in which the amount of a multimeric polypeptide, which is at least one kind of polypeptide selected from the group consisting of the polypeptides (a) to (c) and composed of two or more monomers held together by intermolecular cross-linking via cysteine residues included in the first region, is equal to or less than 20% by mass of the total mass of polypeptides contained in the composition. This polypeptide composition can improve the growth ability of pluripotent stem cells.

Furthermore, another polypeptide composition of the present invention is a composition containing the polypeptide (d) described above, in which the amount of a multimeric polypeptide, which is the polypeptide (d) and composed of two or more monomers held together by intermolecular cross-linking via cysteine residues included in the first region, is equal to or less than 20% by mass of the total mass of polypeptides contained in the composition. The polypeptide composition of the present invention can improve the growth ability of pluripotent stem cells while maintaining the undifferentiated state.

In the present specification, the term "step" includes not only an independent step, but also a step that cannot be clearly distinguished from other steps as long as the intended object thereof is achieved.

In the present specification, a range of numerical values represented by using "to" means a range which includes numerical values listed before and after "to" as a minimum value and a maximum value respectively.

In the present specification, in a case where there is a plurality of substances corresponding to each component in a composition, unless otherwise specified, the amount of each component in the composition means the total amount of the plurality of substances present in the composition.

In the present specification, "homogeneous" means a human being, and "heterogeneous" means an animal other than a human being.

In the present specification, an amino acid residue in an amino acid sequence is designated by one letter (for example, "G" for a glycine residue) or by three letters (for example, "Gly" for a glycine residue) in some cases as widely known in the field of the related art.

In the present invention, unless otherwise specified, "%" relating to an amino acid sequence of a polypeptide is based on the number of amino acid (or imino acid) residues.

In the present specification, the expression such as "the corresponding amino acid residue" used for a specific amino acid residue in an amino acid sequence means an amino acid residue in an amino acid sequence that is in the same position as a specific amino acid residue in another amino acid sequence as a standard when sequence alignment are performed on two or more contrasting amino acid sequences by a method known in the field of the related art in consideration of insertion, deletion, and substitution so as to maximize the number of amino acid residues identical to each other.

In the present specification, "identity" relating to an amino acid sequence can refer to a value calculated by using a BLAST package (see Ausubel et al., 1999 Short Protocols in Molecular Biology, 4th Ed-Chapter 18). For example, to have identity of equal to or higher than 80% with SEQ ID NO: 1 means that a value of Max. Identities in BLAST is equal to or greater than 80.

In the present specification, regarding an amino acid sequence, the expression of the "amino acid sequence formed by deletion, substitution, or addition of amino acids" does not exclude a combination of two or more mutations among deletion, substitution, and addition of amino acids included in the amino acid sequence.

<Polypeptide>

The polypeptides (a) to (c) according to the present invention are as follows.

(a) A polypeptide having an amino acid sequence represented by SEQ ID NO: 1

(b) A polypeptide having an amino acid sequence, which has identity of equal to or higher than 80% with the amino acid sequence represented by SEQ ID NO: 1, and having a pluripotent stem cell culturing property (c) A polypeptide having an amino acid sequence, which is formed by deletion, substitution, or addition of one amino acid or plural amino acids in SEQ ID NO: 1, and having a pluripotent stem cell culturing property

```
SEQ ID NO: 1:
DQESCKGRCTEGFNVDKKCQCDELCSYYQSCCTDYTAECKPQVTRGDVFT

MPEDEYTVYDDGEEKNNATVHEQVGGPSLTSDLQAQSKGNPEQTPVLKPE

EEAPAPEVGASKPEGIDSRPETLHPGRPQPPAEEELCSGKPFDAFTDLKN

GSLFAFRGQYCYELDEKAVRPGYPKLIRDVWGIEGPIDAAFTRINCQGKT

YLFKGSQYWRFEDGVLDPDYPRNISDGFDGIPDNVDAALALPAHSYSGRE

RVYFFKGKQYWEYQFQHQPSQEECEGSSLSAVFEHFAMMQRDSWEDIFEL

LFWGRTSAGTRQPQFISRDWHGVPGQVDAAMAGRIYISGMAPRPSLAKKQ

RFRHRNRKGYRSQRGHSRGRNQNSRRPSRATWLSLFSSEESNLGANNYDD

YRMDWLVPATCEPIQSVFFFSGDKYYRVNLRTRRVDTVDPPYPRSIAQYW

LGCPAPGHL
```

Herein, regarding a polypeptide, "having a pluripotent stem cell culturing property" means the polypeptide has a growth activity for pluripotent stem cells. Whether or not the polypeptide has the growth activity can be evaluated in the following method, for example. Onto a cell culture surface onto which the polypeptide is adsorbed, pluripotent stem cells are seeded at a cell density of 250 cells/well, the pluripotent stem cells are cultured for 8 days, and then nonadhesive cells are washed off with PBS. At this time, whether or not the number of adhesive cells present is equal to or greater than 2,500 cells/well (10 times the number of seeded cells) is checked to evaluate the growth activity.

Herein, the number of the adhesive cells can be quantified by a method in which the activity of alkaline phosphatase expressed by the pluripotent stem cells is quantified, an MTT test, or the like.

The full-length polypeptide represented by SEQ ID NO: 1 constituted with 459 amino acid residues is vitronectin. In the present invention, the vitronectin means human vitronectin. It has been confirmed that natural vitronectin is a sugar protein having a sugar chain in a portion of the sequence thereof.

The polypeptide (b) is preferably a polypeptide having an amino acid sequence, which has identity of equal to or higher than 90% with the amino acid sequence represented by SEQ ID NO: 1, and having a pluripotent stem cell culturing property, and more preferably a polypeptide having an amino acid sequence, which has identity of equal to or higher than 95% with the amino acid sequence represented by SEQ ID NO: 1, and having a pluripotent stem cell culturing property.

The polypeptide (c) is preferably a polypeptide having an amino acid sequence, which is formed by deletion, substitution, or addition of 1 to 5 amino acids in SEQ ID NO: 1, and a having a pluripotent stem cell culturing property.

The polypeptide according to the present invention is preferably (a1) a polypeptide including an amino acid sequence represented by SEQ ID NO: 1, (b1) a polypeptide including an amino acid sequence, which has identity of equal to or higher than 80% with the amino acid sequence represented by SEQ ID NO: 1, and having a pluripotent stem cell culturing property, or (c1) a polypeptide including an amino acid sequence, which is formed by deletion, substitution, or addition of one amino acid or plural amino acids in SEQ ID NO: 1, and having pluripotent stem cell culturing property.

Herein, the polypeptide (b1) is preferably a polypeptide including an amino acid sequence, which has identity of equal to or higher than 90% with the amino acid sequence represented by SEQ ID NO: 1, and having a pluripotent stem cell culturing property, and more preferably a polypeptide including an amino acid sequence, which has identity of equal to or higher than 95% with the amino acid sequence represented by SEQ ID NO: 1, and having a pluripotent stem cell culturing property.

In addition, the polypeptide (c1) is preferably a polypeptide including an amino acid sequence, which is formed by deletion, substitution, or addition of one amino acid or plural amino acids and preferably 1 to 5 amino acids in SEQ ID NO: 1, and having a pluripotent stem cell culturing property.

The polypeptides (a) to (c) include a first region represented by any one of the following amino acid sequences (1-i) to (1-iii).

(1-i) An amino acid sequence consisting of the $1^{st}$ to $44^{th}$ amino acid residues in the amino acid sequence represented by SEQ ID NO: 1

(1-ii) An amino acid sequence including an amino acid sequence, which has identity of equal to or higher than 80% with an amino acid sequence including the amino acid sequence (1-i), and having a cell adhesion ability with respect to pluripotent stem cells (1-iii) An amino acid sequence including an amino acid sequence, which is formed by deletion, substitution, or addition of one amino acid or plural amino acids in the amino acid sequence (1-i), and having a cell adhesion ability with respect to pluripotent stem cells The polypeptide portion consisting of the $1^{st}$ to $44^{th}$ amino acid residues in the amino acid sequence represented by SEQ ID NO: 1 is a region known as a somatomedin B (SMB) region of human vitronectin. The SMB region is known to interact with a plasminogen activator inhibitor-1 (PAI-1). Furthermore, the SMB region includes both an amino acid sequence, which is represented by CSYYQSC (SEQ ID NO: 2) corresponding to 7 amino acid residues consisting of the $25^{th}$ to $31^{st}$ amino acid residues in the amino acid sequence of the vitronectin, and an RGD sequence which is a cell-adhesive motif corresponding to 3 amino acid residues consisting of the $45^{th}$ to $47^{th}$ amino acid residues in the amino acid sequence of the vitronectin. The first region in the polypeptides (a) to (c) should include any one sequence selected from the group consisting of the amino acid sequence represented by SEQ ID NO: 2 and the RGD sequence. From the viewpoint of the cell adhesiveness and the cell growth properties, the first region in the polypeptides (a) to (c) preferably includes both of the sequences.

That is, the first region represented by (1-i) to (1-iii) is a sequence positioned relatively on the N-terminal side of the natural vitronectin, and exhibits adhesiveness with respect to undifferentiated pluripotent stem cells. Presumably, as a result, the first region may enable the growth of the pluripotent stem cells. Therefore, compared to a polypeptide not including the first region, a polypeptide including the first region exhibits better cell adhesiveness and better cell growth ability.

In the present invention, the first region including a predetermined amino acid sequence in the polypeptides (a) to (c) has excellent cell adhesiveness. Accordingly, the polypeptide in the present invention can excellently grow cells, particularly, pluripotent stem cells. The polypeptides (a) to (c) according to the present invention having such an amino acid sequence can grow pluripotent stem cells over a long period of time.

A polypeptide having "a cell adhesion ability with respect to pluripotent stem cells" means a polypeptide which enables pluripotent stem cells to exhibit adhesiveness with respect to the polypeptide. Whether or not pluripotent stem cells exhibit adhesiveness with respect to the polypeptide can be evaluated by a known evaluation method. For example, 24 hours after pluripotent stem cells are seeded onto a culture surface coated with a polypeptide, the culture surface is gently washed with phosphate buffered saline (PBS). Then, based on the amount of the pluripotent stem cells remaining on the culture surface after washing, whether or not the pluripotent stem cells exhibit adhesiveness can be evaluated.

The amino acid sequence represented by (1-ii) is preferably an amino acid sequence including an amino acid sequence, which has identity of equal to or higher than 90% with an amino acid sequence including the amino acid sequence (1-i), and having a cell adhesion ability with respect to pluripotent stem cells, and more preferably an amino acid sequence including an amino acid sequence, which has identity of equal to or higher than 95% with an amino acid sequence including the amino acid sequence (1-i), and having a cell adhesion ability with respect to pluripotent stem cells.

The amino acid sequence represented by (1-iii) is preferably an amino acid sequence including an amino acid sequence, which is formed by deletion, substitution, or addition of 1 to 5 amino acids in the amino acid sequence (1-i), and having a cell adhesion ability with respect to pluripotent stem cells.

The $1^{st}$ to $44^{th}$ amino acid residues in the amino acid sequence represented by SEQ ID NO: 1 include cysteine residues as the $5^{th}$, $9^{th}$, $19^{th}$, 21st, $25^{th}$, 31st, $32^{nd}$, and $39^{th}$ amino acid residues. The polypeptides (a) to (c) may not include the cysteine residues corresponding to the 8 cysteine residues or may contain at least one of the 8 cysteine residues. A cysteine residue tends to be easily cross-linked with other cysteine residues under physiological conditions. Consequently, in a case where the polypeptides (a) to (c) include cysteine residues, intramolecular cross-linking may occur between cysteine residues in different positions in the polypeptides.

From the viewpoint of accelerating and improving the growth of pluripotent stem cells, the polypeptides (a) to (c) preferably include 2 or more cysteine residues among the aforementioned 8 cysteine residues in the amino acid sequence represented by SEQ ID NO: 1. It is particularly preferable that intramolecular cross-linking occurs between 2 or more cysteine residues included in the first region.

From the viewpoint of accelerating and improving the growth of pluripotent stem cells, the combination of cysteine residues that can establish intramolecular cross-linking preferably includes a combination of a cysteine residue corresponding to the $5^{th}$ amino acid residue and a cysteine residue corresponding to the $9^{th}$ amino acid residue; a combination of a cysteine residue corresponding to the $19^{th}$ amino acid residue and a cysteine residue corresponding to the $21^{st}$ amino acid residue; a combination of a cysteine residue corresponding to the $25^{th}$ amino acid residue and a cysteine residue corresponding to the 30 amino acid residue; and a combination of a cysteine residue corresponding to the $32^{nd}$ amino acid residue and a cysteine residue corresponding to the $39^{th}$ amino acid residue. The polypeptides (a) to (d) preferably include any one of the 4 preferred combinations of the cysteine residues that can establish intramolecular cross-linking, and more preferably include all of the 4 combinations. In the present specification, a specific cysteine residue is represented in combination with a number showing the position in the amino acid sequence represented by SEQ ID NO: 1 in some cases. For example, a cysteine residue corresponding to the $25^{th}$ amino acid residue in the amino acid sequence represented by SEQ ID NO: 1 is represented by "Cys 25" in some cases.

From the viewpoint of the cell adhesiveness and growth properties of the pluripotent stem cells, the number of amino acid residues of the first region can be set to be 3 to 60 and is preferably 10 to 55.

The number of amino acid residues (amino acid length) included in the polypeptides (a) to (c) is not particularly limited as long as it is within a range of 400 to 550. In view of sharing high homology with the human vitronectin, the number of amino acid residues is preferably 450 to 520, and more preferably 450 to 459.

The polypeptide (d) according to the present invention is as follows.

A polypeptide which includes a first region represented by any one of the amino acid sequences (1-i) to (1-iii) described above and a second region represented by any one of the following amino acid sequences (2-i) to (2-iii) and consists of 40 to 450 amino acid residues:

(2-i) An amino acid sequence represented by PRPSLAK-KQRFRHRNRKGYRSQRGHSRGRNQN (SEQ ID NO: 3), (2-ii) An amino acid sequence which has identity of equal to or higher than 80% with the amino acid sequence represented by SEQ ID NO: 3 and has adsorbability with respect to a cell culture surface of a support, and (2-iii) An amino acid sequence which is formed by the addition, substitution, or deletion of one amino acid residue or plural amino acid residues in the amino acid sequence represented by SEQ ID NO: 3 and has adsorbability with respect to the cell culture surface of the support.

The polypeptide (d) has a pluripotent stem cell culturing property. Therefore, the polypeptide (d) is preferable because it has the "cell adhesiveness with respect to pluripotent stem cells" and the "adsorbability with respect to a cell culture surface of a support". Herein, the support is a portion of a culture vessel having a surface onto which the polypeptide according to the present invention is applied at the time of culturing cells by using a culture method of the present invention.

That is, because the first region represented by any one of the amino acid sequences (1-i) to (1-iii) has excellent cell adhesiveness, it enables cells, particularly, pluripotent stem cells to grow excellently. The polypeptide (d) including such an amino acid sequence can grow pluripotent stem cells over a long period of time while maintaining the undifferentiated state.

Furthermore, the second region represented by any one of the amino acid sequences (2-i) to (2-iii) contributes to the adsorption properties onto the cell culture surface of the support. The polypeptide (d) including such an amino acid sequence exhibits excellent adhesiveness with respect to the cell culture surface of the support. The polypeptide (d) includes both of the first and second regions. Accordingly, the polypeptide (d) is not exfoliated from the cell culture surface of the support for the duration of culture and enables pluripotent stem cells to grow over a long period of time while maintaining the undifferentiated state. In addition, the polypeptide (d) enables the undifferentiated pluripotent stem cells being cultured to grow while inhibiting the exfoliation of the cells from the cell culture surface of the support, and can improve the handleability during the culture operation.

As a result, the polypeptide (d) can accelerate the growth of the pluripotent stem cells in the undifferentiated state, does not need to be so treated that it is immobilized onto the cell culture surface of the support by chemical bonding, and can be obtained as an industrially producible polypeptide.

The polypeptide (d) can eliminate the risk of the intermixing of an antigenic substance and an infection source unlike the natural human vitronectin, and can retain the property equivalent to the property of the natural vitronectin, that is, the adhesiveness with respect to the pluripotent stem cells, the cell growth properties, and the undifferentiated state maintainability.

Herein, regarding a polypeptide, "enabling the pluripotent stem cells to grow in the undifferentiated state" means that the pluripotent stem cells retains differentiation potency for the duration of culture. Whether or not the pluripotent stem cells are in an undifferentiated state can be evaluated by a known method. For example, it can be evaluated by the methods known to those in the related art, such as expression of molecular markers (measuring the expression of SSEA-4 and/or Oct-4 by means of flow cytometry, immunostaining by using Oct-4 and/or NANOG, and the like), checking the pluripotent differentiation by in-vitro experiment, and checking the formation of teratoma resulting from the transplantation of the cells into an immunodeficient mouse. Whether or not the pluripotent stem cells are growing should be evaluated through a common method by means of visual observation using various microscopes, a method using a test for reactivity such as ALP activity, a method using flow cytometery, or other methods. In the present invention, the duration for which the pluripotent stem cells are cultured in a state of retaining the differentiation potency can be set to be, for example, one month, although the duration varies with the culture conditions and the state of the pluripotent stem cells.

The first region in the polypeptide (d) is the same as the first region in the polypeptides (a) to (c). Regarding the matters relating to the first region in the polypeptide (d), the matters described for the polypeptides (a) to (c) will be applied as they are.

The second region includes an amino acid sequence consisting of 32 amino acid residues represented by SEQ ID NO: 3. From the viewpoint of ease of purifying the polypeptide (d), the second region in the polypeptide (d) is preferably a polypeptide including the amino acid sequence represented by SEQ ID NO: 3. The amino acid sequence represented by SEQ ID NO: 3 is included in a portion of a hemopexin-like region II positioned on the C-terminal side of the natural vitronectin and corresponds to a heparin binding region constituted with the $342^{nd}$ to $373^{rd}$ amino acid residues of the amino acid sequence represented by SEQ ID NO: 1. Hereinafter, the amino acid sequence represented by SEQ ID NO: 3 will be referred to as a heparin binding region in some cases.

Presumably, the polypeptide (d) may have adsorbability with respect to the cell culture surface of the support because of having the heparin binding region. Therefore, the use of the polypeptide (d) enables the undifferentiated pluripotent stem cells to grow over a long period of time while maintaining the undifferentiated state.

Furthermore, because the polypeptide (d) includes the heparin binding region, the hydrophilicity of the polypeptide (d) is ensured, and the hydrophobic aggregation of the polypeptide tends to be inhibited. As a result, it is easy to purify the polypeptide (d), and the production efficiency is high.

Herein, "having adsorbability with respect to the cell culture surface of the support" means that the amino acid sequence is physically adsorbed onto the cell culture surface of a target culture vessel (hereinafter, simply referred to as a "culture surface" in some cases) without chemically reacting with the culture surface. Whether or not the polypeptide has adsorbability with respect to the cell culture surface of the support can be evaluated by the following method, for example. In the method, a solution containing the polypeptide is added in an amount of 200 pmol/cm² to a plasma-treated culture vessel made of polystyrene, and the culture vessel is left to stand for 2 hours at 37° C. and then washed twice with a phosphate buffered saline. Thereafter, whether or not the amount of the polypeptide remaining on the surface of the culture dish is equal to or greater than 10 pmol/cm² is checked to evaluate the adsorbability of the polypeptide.

The amount of the polypeptide remaining on the surface of the culture dish can be measured by an Enzyme-Linked Immunosorbent Assay (ELISA) method in which the amount of the polypeptide binding to antibodies recognizing the polypeptide is determined or by a method in which the adsorbed polypeptide is hydrolyzed and the amount of the generated amino acid is determined by HPLC or the like.

The heparin binding region may have identity of equal to or higher than 80% with the amino acid sequence represented by SEQ ID NO: 3. The identity may be preferably equal to or higher than 90%, and more preferably equal to or higher than 95%. Furthermore, the heparin binding region may be an amino acid sequence which enables the pluripotent stem cells to grow in an undifferentiated state and has adsorbability with respect to the cell culture surface of the support.

The heparin binding region may be an amino acid sequence including an amino acid sequence, which is formed by deletion, substitution, or addition of one amino acid residue or plural amino acid residues and preferably 1 to 5 amino acid residues in the amino acid sequence represented by SEQ ID NO: 3, and having adsorbability with respect to the cell culture surface of the support.

The polypeptide (d) should have the first and second regions, and the relative position thereof is not particularly limited. In the polypeptide (d), the first region is preferably positioned on the N-terminal side of the second region.

The polypeptide (d) having the first and second regions consists of 40 to 450 amino acid residues. If the number of the amino acid residues is equal to or greater than 40, the cell adhesiveness, the cell growth properties, or the adsorbability with respect to the cell culture surface of the support becomes excellent. In contrast, if the number of the amino acid residues is equal to or less than 450, the cell adhesiveness, the cell growth properties, and the adsorbability with respect to the cell culture surface of the support are further exhibited, and the protein molecules can be inhibited from being agglomerated, cross-linked, or aggregated. From the viewpoint of making it difficult for the protein molecules to be aggregated, the number of amino acid residues constituting the polypeptide (d) is preferably equal to or greater than 80, more preferably equal to or greater than 90, and even more preferably equal to or greater than 100. Furthermore, the number of amino acid residues constituting the polypeptide (d) is preferably equal to or less than 400, more preferably equal to or less than 250, even more preferably equal to or less than 170, and still more preferably equal to or less than 150. Any of the aforementioned upper limits may be combined with any of the aforementioned lower limits. For example, the polypeptide (d) preferably consists of 40 to 400 amino acid residues, more preferably consists of 80 to 250 amino acid residues, even more preferably consists of 80 to 150 amino acid residues, and still more preferably consists of 100 to 150 amino acid residues.

From the viewpoint of preventing the hydrophobic aggregation, it is preferable that the polypeptides (a) to (d) have a GRAVY value of −2.0 to −0.95. The GRAVY value (Kyte J., Doolittle R. F. (1982), J. Mol. Biol, 157: 105-132) represents the total average of a degree of hydrophobicity of the polypeptide. The greater the GRAVY value, the higher the degree of hydrophobicity. If the GRAVY value is equal to or less than −0.95, the occurrence of the hydrophobic aggregation tends to be easily inhibited. In contrast, if the GRAVY value is equal to or greater than −2.0, the polypeptide tends to be easily adsorbed onto the cell culture surface of the support, the undifferentiated cells tend to grow easily, and the adsorption properties and the cell growth properties tend to be improved as the GRAVY value increases. In view of accomplishing both the inhibition of the aggregation and the adsorption properties or the cell growth properties, the GRAVY value of the polypeptide is more preferably −1.70 to −0.975, and even more preferably −1.60 to −1.10. The smaller the number of the amino acid residues, the more the aggregation tends to occur. Therefore, in a case of a polypeptide consisting of 80 to 170 amino acid residues, in view of accomplishing both the inhibition of the aggregation and the adsorption properties or the cell growth properties, the GRAVY value is preferably −1.70 to −0.975 and more preferably −1.60 to −1.10.

The GRAVY value can be adjusted by increasing or decreasing the proportion of, for example, a hydrophobic amino acid (for example, Trp, Tyr, Phe, Leu, Ile, Val, or Met) in the sequence or by increasing or decreasing the number of amino acid residues in the sequence.

It is preferable that the polypeptides (a) to (d) further have an amino acid sequence other than the amino acid sequence described above. From the viewpoint of sufficiently exhibiting the cell adhesiveness and the adsorbability with respect to the cell culture surface of the support, the polypeptides (a) to (d) preferably further include the amino acid sequence represented by SEQ ID NO: 1, that is, a partial sequence of the amino acid sequence of human vitronectin. In this way, the polypeptides (a) to (d) can obtain properties close to the properties of the human vitronectin, for example, excellent adhesiveness and growth properties for the pluripotent stem cells.

From the viewpoint of the cell adhesiveness and the cell growth properties of the polypeptides (a) to (d), the adsorbability with respect to the cell culture surface of the support, or the inhibition of aggregation, the partial amino acid sequence of the human vitronectin that can be include in the polypeptides (a) to (d) preferably includes at least one region selected from the group consisting of the following third and fourth regions.

(3) A third region including an amino acid sequence selected from an amino acid sequence, which consists of the $56^{th}$ to $341^{st}$ amino acid residues in the amino acid sequence represented by SEQ ID NO: 1, and a partial amino acid sequence thereof; and (4) a fourth region including an amino acid sequence selected from an amino acid sequence, which consists of the $374^{th}$ to $459^{th}$ amino acid residues in the amino acid sequence represented by SEQ ID NO: 1, and a partial amino acid sequence thereof.

As the third region, it is possible to select (3a) an amino acid sequence, which consists of the $56^{th}$ to $341^{st}$ amino acid residues in the amino acid sequence represented by SEQ ID NO: 1, or a partial amino acid sequence thereof, (3b) an amino acid sequence, which consists of the $269^{th}$ to $341^{st}$ amino acid residues in the amino acid sequence represented by SEQ ID NO: 1, or a partial amino acid sequence thereof, (3c) an amino acid sequence, which consists of the $274^{th}$ to $341^{st}$ amino acid residues in the amino acid sequence represented by SEQ ID NO: 1, or a partial amino acid sequence thereof, or (3d) an amino acid sequence, which consists of the $294^{th}$ to $341^{st}$ amino acid residues in the amino acid sequence represented by SEQ ID NO: 1, or a partial amino acid sequence thereof, because the above amino acid sequences tend to inhibit the hydrophobic aggregation at the time of preparing the polypeptide. With the amino acid sequences (3a) to (3d), the hydrophobic aggregation tends to be able to be mitigated by reducing the number of amino acid residues. It is particularly preferable to select the amino acid sequence (3d) because the hydrophobic aggregation tends to be able to be more reliably inhibited.

It is preferable that the polypeptides (a) to (d) further include the third region including any one of the following amino acid sequences (3a-i) to (3a-iii).

(3a-i) An amino acid sequence, which consists of the $56^{th}$ to $341^{st}$ amino acid residues in the amino acid sequence represented by SEQ ID NO: 1, or a partial amino acid sequence thereof;

(3a-ii) an amino acid sequence which has identity of equal to or higher than 80%, preferably equal to or higher than 90%, and more preferably equal to or higher than 95% with the amino acid sequence (3a-i) or the partial amino acid sequence thereof; and (3a-iii) an amino acid sequence which is formed by deletion, substitution, or addition of one amino acid or plural amino acids and preferably 1 to 5 amino acids in the amino acid sequence (3a-i) or the partial amino acid sequence thereof.

It is also preferable that the polypeptides (a) to (d) further include a third region including any one of the following amino acid sequences (3b-i) to (3b-iii).

(3b-i) An amino acid sequence, which consists of the $269^{th}$ to $341^{st}$ amino acid residues in the amino acid sequence represented by SEQ ID NO: 1, or a partial amino acid sequence thereof;

(3b-ii) an amino acid sequence which has identity of equal to or higher than 80%, preferably equal to or higher than 90%, and more preferably equal to or higher than 95% with the amino acid sequence (3b-i) or the partial amino acid sequence thereof; and (3b-iii) an amino acid sequence which is formed by deletion, substitution, or addition of one amino acid or plural amino acids and preferably, 1 to 5 amino acids in the amino acid sequence (3b-i) or the partial amino acid sequence thereof.

From the viewpoint of the adsorption properties with respect to the culture dish, for the fourth region, it is possible to select an amino acid sequence, which consists of the $374^{th}$ to $459^{th}$ amino acid residues in the amino acid sequence represented by SEQ ID NO: 1, or a partial amino acid sequence thereof, to select an amino acid sequence which consists of the $374^{th}$ to $409^{th}$ amino acid residues in the amino acid sequence represented by SEQ ID NO: 1, or a partial amino acid sequence thereof, or to select an amino acid sequence, which consists of the $374^{th}$ to $379^{th}$ amino acid residues in the amino acid sequence represented by SEQ ID NO: 1, or a partial amino acid sequence thereof.

Among these, an amino acid sequence, which consists of the $374^{th}$ to $379^{th}$ amino acid residues in the amino acid sequence represented by SEQ ID NO: 1 is preferable, because such an amino acid sequence makes it possible to obtain the adsorption properties with respect to the culture dish and makes it easy to inhibit the hydrophobic aggregation at the time of preparing the polypeptide. By reducing the number of amino acids selected, the hydrophobic aggregation tends to be mitigated.

It is preferable that the polypeptides (a) to (d) further include a fourth region including any one of the following amino acid sequences (4a-i) to (4a-iii).

(4a-i) An amino acid sequence, which consists of the $374^{th}$ to $459^{th}$ amino acid residues in the amino acid sequence represented by SEQ ID NO: 1, or a partial amino acid sequence thereof;

(4a-ii) an amino acid sequence which has identity of equal to or higher than 80%, preferably equal to or higher than 90%, and more preferably equal to or higher than 95% with the amino acid sequence (4a-i) or the partial amino acid sequence thereof; and (4a-iii) an amino acid sequence which is formed by deletion, substitution, or addition of one amino acid or plural amino acids, preferably, 1 to 5 amino acids in the amino acid sequence (4a-i) or the partial amino acid sequence thereof.

It is also preferable that the polypeptides (a) to (d) further include a fourth region including any one of the following amino acid sequences (4b-i) to (4b-iii).

(4b-i) An amino acid sequence, which consists of the $374^{th}$ to $409^{th}$ amino acid residues in the amino acid sequence represented by SEQ ID NO: 1, or a partial amino acid sequence thereof;

(4b-ii) an amino acid sequence which has identity of equal to or higher than 80%, preferably equal to or higher than 90%, and more preferably equal to or higher than 95% with the amino acid sequence (4b-i) or the partial amino acid sequence thereof; and (4b-iii) an amino acid sequence which is formed by deletion, substitution, or addition of one amino acid or plural amino acids, preferably, 1 to 5 amino acids in the amino acid sequence (4b-i) or the partial amino acid sequence thereof.

It is also preferable that the polypeptides (a) to (d) further include a fourth region including any one of the following amino acid sequences (4c-i) to (4c-iii).

(4c-i) An amino acid sequence, which consists of the $374^{th}$ to $379^{th}$ amino acid residues in the amino acid sequence represented by SEQ ID NO: 1, or a partial amino acid sequence thereof;

(4c-ii) an amino acid sequence which has identity of equal to or higher than 80%, preferably equal to or higher than 90%, and more preferably equal to or higher than 95% with the amino acid sequence (4c-i) or the partial amino acid sequence thereof; and (4c-iii) an amino acid sequence which is formed by deletion, substitution, or addition of one amino acid or plural amino acids, preferably, 1 to 5 amino acids in the amino acid sequence (4c-i) or the partial amino acid sequence thereof.

The partial amino acid sequence of the amino acid sequence constituting the third and fourth regions means an amino acid sequence constituted with three or more consecutive amino acid residues within a predetermined range of amino acid residues. The number of amino acid residues of the partial amino acid sequence should be selected within a range that does not exceed the aforementioned total number of amino acid residues of the polypeptide (d).

By including the third region, the polypeptides (a) to (d) tend to obtain an advantage of improving the adsorption properties with respect to the culture dish. Furthermore, by including the fourth region, the polypeptides (a) to (d) tend to obtain an advantage of further improving the adsorption properties with respect to the culture dish. The polypeptides (a) to (d) may have either or both of the third and fourth regions.

The GRAVY value of the polypeptides (a) to (d) is preferably adjusted by increasing or decreasing the number of amino acid residues in the amino acid sequences constituting the third and fourth regions or by deletion, substitution, addition, or the like of the amino acid residues, because then the GRAVY value can be easily adjusted. Particularly, the GRAVY value of the polypeptides (a) to (d) is more preferably adjusted by adjusting the length of the amino acid sequence constituting the third region.

Among the amino acid residues constituting the amino acid sequence represented by SEQ ID NO: 1, the $56^{th}$ to $131^{st}$ amino acid residues, the $56^{th}$ to $268^{th}$ amino acid residues, the $269^{th}$ to $273^{rd}$ amino acid residue, or the $50^{th}$ to $293^{rd}$ amino acid residues may not be included in the polypeptides (a) to (d). Presumably, an amino acid sequence consisting of the above amino acid residues may not make a contribution to the property of the polypeptides (a) to (d) with respect to the pluripotent stem cells. Therefore, a sequence suitable for the adsorption of the polypeptide onto the culture dish is selected.

In a case where the third region includes an amino acid residue corresponding to a cysteine residue of the sequence represented by SEQ ID NO: 1, the third region may have an amino acid residue other than the cysteine residue in the position of the cysteine residue. It is preferable that the third region has an amino acid residue other than the cysteine residue because then intramolecular cross-linking or intermolecular cross-linking caused by the cysteine residue can be prevented. Other amino acid residues substituting the cysteine residue are not particularly limited, and preferred examples thereof include a serine residue, an alanine residue, a glycine residue, and the like. Among these, a serine residue or an alanine residue are preferable because these have a structure similar to that of cysteine.

The polypeptides (a) to (d) may have any additional amino acid residues other than the aforementioned amino acid residues within a range that does not impair the cell adhesiveness and the adsorption properties with respect to the cell culture surface of the support. Examples of the sequence consisting of any other amino acid residues described above include an additional sequence added for easily preparing the polypeptides (a) to (d) by a recombination technique. Examples of the additional sequence include a methionine residue on the N-terminal side, a GPLG sequence on the N-terminal side, a tag sequence (for example, glutathione S-transferase (GST), a FLAG tag, or a His tag), a linker sequence (for example, GGGS (SEQ ID NO: 40), GGGGS (SEQ ID NO: 41), or GGGGGS (SEQ ID NO: 42)) which can be added so as to be positioned between the respective regions, and the like.

The polypeptides (a) to (d) can be manufactured by an amino acid synthesis technique or a gene recombination technique known to those in the related art.

Specifically, in a case where the polypeptides (a) to (d) are obtained by the gene recombination technique, first, a gene encoding a target amino acid sequence is obtained, and the obtained gene is incorporated into an expression vector, thereby preparing a recombinant expression vector. Thereafter, by introducing the obtained recombinant expression vector into an appropriate host, a transformant is prepared. By culturing the obtained transformant in an appropriate medium, an intended polypeptide is produced. Therefore, by collecting the intended polypeptide from the culture by a common method, the polypeptides (a) to (d) can be obtained.

From the viewpoint of the cell growth properties and the ability to grow the undifferentiated pluripotent stem cells in the undifferentiated state, and the like, each of the polypeptides (a) to (c) and (d) is preferably a polypeptide (A) which consists of 80 to 450 amino acid residues and includes (1) a first region including an amino acid sequence consisting of the $1^{st}$ to $47^{th}$ amino acid residues of the amino acid sequence represented by SEQ ID NO: 1, (2) a second region, which includes an amino acid sequence (SEQ ID NO: 3, heparin binding region) consisting of the $342^{nd}$ to $373^{rd}$ amino acid residues of the amino acid sequence represented by SEQ ID NO: 1, and at least one region selected from the group consisting of the following third and fourth regions: (3) a third region including an amino acid sequence, which consists of the $269^{th}$ to $341^{st}$ amino acid residues of the amino acid sequence represented by SEQ ID NO: 1, or a partial amino acid sequence thereof; and (4) a fourth region including an amino acid sequence, which consists of the 374$^{th}$ to 459$^{th}$ amino acid residues of the amino acid sequence represented by SEQ ID NO: 1, or a partial amino acid sequence thereof.

Furthermore, from the viewpoint of the cell growth properties, the ability to grow the undifferentiated pluripotent stem cells in the undifferentiated state, and the like, each of the polypeptides (a) to (c) and (d) is preferably a polypeptide (B) which consists of 100 to 450 amino acid residues and includes (1) a first region including an amino acid sequence (including the amino acid sequence represented by SEQ ID NO: 2 and the RGD sequence) consisting of the 1$^{st}$ to 44$^{th}$ amino acid residues of the amino acid sequence represented by SEQ ID NO: 1, (2) a second region (heparin binding region) including an amino acid sequence, which consists of the 342$^{nd}$ to 373$^{rd}$ amino acid residues of the amino acid sequence represented by SEQ ID NO. 1, and at least one region selected from the group consisting of the following third and fourth regions: (3) a third region including an amino acid sequence, which consists of the 269$^{th}$ to 341$^{st}$ amino acid residues of the amino acid sequence represented by SEQ ID NO: 1, or a partial amino acid sequence thereof; and (4) a fourth region including an amino acid sequence, which consists of the 374$^{th}$ to 459$^{th}$ amino acid residues of the amino acid sequence represented by SEQ ID NO: 1, and a partial amino acid sequence thereof.

From the viewpoint of the cell growth properties, the ability to grow the undifferentiated pluripotent stem cells in the undifferentiated state, and the like, each of the polypeptides (a) to (c) is preferably a polypeptide (A) consisting of 400 to 550 amino acid residues and including (1) a first region including an amino acid sequence consisting of the 1$^{st}$ to 47$^{th}$ amino acid residues of the amino acid sequence represented by SEQ ID NO: 1, (2) a second region (SEQ ID NO: 3, heparin binding region) including an amino acid sequence consisting of the 342$^{nd}$ to 373$^{rd}$ amino acid residues of the amino acid sequence represented by SEQ ID NO: 1, and at least one region selected from the group consisting of the following third and fourth regions: (3) a third region including an amino acid sequence, which consists of the 269$^{th}$ to 341$^{st}$ amino acid residues of the amino acid sequence represented by SEQ ID NO: 1, or a partial amino acid sequence thereof; and (4) a fourth region including an amino acid sequence, which consists of the 374$^{th}$ to 459$^{th}$ amino acid residues of the amino acid sequence represented by SEQ ID NO: 1, or a partial amino acid sequence thereof.

In addition, from the viewpoint of the cell growth properties, the ability to grow the undifferentiated pluripotent stem cells in the undifferentiated state, and the like, each of the polypeptides (a) to (c) is preferably a polypeptide (B) consisting of 400 to 550 amino acid residues and including (1) a first region including an amino acid sequence consisting of the 1$^{st}$ to 55$^{th}$ amino acid residues of the amino acid sequence represented by SEQ ID NO: 1, (2) a second region (SEQ ID NO: 3, heparin binding region) including an amino acid sequence consisting of the 342$^{nd}$ to 373$^{rd}$ amino acid residues of the amino acid sequence represented by SEQ ID NO: 1, and at least one region selected from the group consisting of the following third and fourth regions: (3) a third region including an amino acid sequence, which consists of the 269$^{th}$ to 341$^{st}$ amino acid residues of the amino acid sequence represented by SEQ ID NO: 1, or a partial amino acid sequence thereof; and (4) a fourth region including an amino acid sequence, which consists of the 374$^{th}$ to 459$^{th}$ amino acid residues of the amino acid sequence represented by SEQ ID NO: 1, or a partial amino acid sequence thereof.

The polypeptide (A) or (B) is preferably a polypeptide having a GRAVY value of −2.0 to −0.95.

The polypeptide (A) as the polypeptide (d) preferably consists of 80 to 250 amino acid residues.

The polypeptide (A) or (B) as the polypeptide (d) is more preferably a polypeptide which has a GRAVY value of −2.0 to −0.95 and consists of 80 to 250 amino acid residues.

The polypeptide (A) as the polypeptide (d) is even more preferably a polypeptide which has a GRAVY value of −1.70 to −0.975 and consists of 80 to 250 amino acid residues.

The polypeptide (A) or (B) as the polypeptide (d) preferably consists of 100 to 250 amino acid residues.

The polypeptide (A) or (B) as the polypeptide (d) is more preferably a polypeptide which has a GRAVY value of −2.0 to −0.95 and consists of 100 to 250 amino acid residues.

The polypeptide (A) or (B) as the polypeptide (d) is even more preferably a polypeptide which has a GRAVY value of −1.70 to −0.975 and consists of 100 to 250 amino acid residues.

The polypeptide (A) or (B) as the polypeptide (d) is still more preferably a polypeptide which has a GRAVY value of −1.70 to −0.975 and consists of 100 to 170 amino acid residues.

Examples of the polypeptides (a) to (c) or the polypeptide (d) are shown below, but the present invention is not limited thereto.

TABLE 1

| Amino acid sequence | SEQ ID No. |
|---|---|
| DQESCKGRCTEGFNVDKKCQCDELCSYYQSCCTDYTAECKPQVTRGDVFTMPEDEPSQEE CEGSSLSAVFEHFAMMQRDSWEDIFELLFWGRTSAGTRQPQFISRDWHGVPGQVDAAMAG RIYISGMAPRPSLAKKQRFRHRNRKGYRSQRGHSRGRNQNSRRPSRATWLSLFSSEESNLG ANNYDDYRMDWLVPATCEPIQSVFFFSGDKYYRVNLRTRRVDTVDPPYPRSIAQYWLGCPA PGHL | 4 |
| DQESCKGRCTEGFNVDKKCQCDELCSYYQSCCTDYTAECKPQVTRGDVFTMPEDEPRPSL AKKQRFRHRNRKGYRSQRGHSRGRNQN | 5 |
| DQESCKGRCTEGFNVDKKCQCDELCSYYQSCCTDYTAECKPQVTRGDVFTMPEDEGVPG QVDAAMAGR1YISGMAPRPSLAKKQRFRHRNRKGYRSQRGHSRGRNQN | 6 |
| DQESCKGRCTEGFNVDKKCQCDELCSYYQSCCTDYTAECKPQVTRGDVFTMPEDEQPQFI SRDWHGVPGQVDAAMAGRIYISGMAPRPSLAKKQRFRHRNRKGYRSQRGHSRGRNQN | 7 |

TABLE 1-continued

| Amino acid sequence | SEQ ID No. |
|---|---|
| DQESCKGRCTEGFNVDKKCQCDELCSYYQSCCTDYTAECKPQVTRGDVFTMPEDEFWGR<br>TSAGTRQPQFISRDWHGVPGQVDAAMAGRIYISGMAPRPSLAKKQRFRHRNRKGYRSQRG<br>HSRGRNQN | 8 |
| DQESCKGRCTEGFNVDKKCQCDELCSYYQSCCTDYTAECKPQVTRGDVFTMPEDESQEES<br>EGSSLSAVFEHFAMMQRDSWEDIFELLFWGRTSAGTRQPQFISRDWHGVPGQVDAAMAGR<br>IYISGMAPRPSLAKKQRFRHRNRKGYRSQRGHSRGRNQNSRRPSRATWLSLFSSEESNLGA<br>NNYDDYRMDWLVPATSEPIQSVFFFSGDKYYRVNLRTRRVDTVDPPYPRSIAQYWLGCPAP<br>GHL | 9 |
| DQESCKGRCTEGFNVDKKCQCDELCSYYQSCCTDYTAECKPQVTRGDVFTMPEDESQEES<br>EGSSLSAVFEHFAMMQRDSWEDIFELLFWGRTSAGTRQPQFISRDWHGVPGQVDAAMAGR<br>IYISGMAPRPSLAKKQRFRHRNRKGYRSQRGHSRGRNQN | 10 |
| DQESCKGRCTEGFNVDKKCQCDELCSYYQSCCTDYTAECKPQVTRGDVFTMPEDESQEES<br>EGSSLSAVFEHFAMMGQRDSWEDIFELLFWGRTSAGTRQPQFISRDWHGVPGQVDAAMAGR<br>IYISGMAPRPSLAKKQRFRHRNRKGYRSQRGHSRGRNQNSRRPSR | 11 |
| DQESCKGRCTEGFNVDKKCQCDELCSYYQSCCTDYTAECKPQVTRGDVFTMPEDESQEES<br>EGSSLSAVFEHFAMMQRDSWEDIFELLFWGRTSAGTRQPQFISRDWHGVPGQVDAAMAGR<br>IYISGMAPRPSLAKKQRFRHRNRKGYRSQRGHSRGRNQNSRRPSRATWLSLFSSE | 12 |
| DQESCKGRCTEGFNVDKKCQCDELCSYYQSCCTDYTAECKPQVTRGDVFTMPEDESQEES<br>EGSSLSAVFEHFAMMQRDSWEDIFELLFWGRTSAGTRQPQFISRDWHGVPGQVDAAMAGR<br>IYISGMAPRPSLAKKQRFRHRNRKGYRSQRGHSRGRNQNSRRPSRATWLSLFSSEESNLGA<br>NNYD | 13 |
| DQESCKGRCTEGFNVDKKCQCDELCSYYQSCCTDYTAECKPQVTRGDVFTMPEDESQEES<br>EGSEDIFELLFWGRTSAGTRQPQFISRDWHGVPGQVDAAMAGRIYISGMAPRPSLAKKQRF<br>RHRNRKGYRSQRGHSRGRNQN | 38 |

Examples of the polypeptides (a) to (c) or the polypeptide (d) according to the present invention preferably include (d1) a polypeptide having an amino acid sequence which is represented by one of SEQ ID NO: 4 to SEQ ID NO: 23, SEQ ID NO: 38, and SEQ ID NO: 39, (d2) a polypeptide having an amino acid sequence, which has identity of equal to or higher than 80%, more preferably equal to or higher than 90%, and even more preferably equal to or higher than 95% with the amino acid sequence represented by one of SEQ ID NO: 4 to SEQ ID NO 23, SEQ ID NO 38, and SEQ ID NO 39, and having a pluripotent stem cell culturing property, and (d3) a polypeptide having an amino acid sequence, which is formed by deletion, substitution, or addition of one amino acid or plural amino acids, preferably, 1 to 5 amino acids in the amino acid sequence represented by one of SEQ ID NO: 4 to SEQ ID NO: 23, SEQ ID NO: 38, and SEQ ID NO: 39, and having a pluripotent stem cell culturing property, and more preferably include (d4) a polypeptide including an amino acid sequence represented by one of SEQ ID NO: 4 to SEQ ID NO: 23, SEQ ID NO: 38, and SEQ ID NO: 39, (d5) a polypeptide including an amino acid sequence, which has identity of equal to or higher than 80%, more preferably equal to or higher than 90%, and even more preferably equal to or higher than 95% with the amino acid sequence represented by one of SEQ ID NO: 4 to SEQ ID NO: 23, SEQ ID NO: 38, and SEQ ID NO: 39, and having a pluripotent stem cell culturing property, and (d6) a polypeptide including an amino acid sequence, which is formed by deletion, substitution, or addition of one amino acid or plural amino acids, preferably, 1 to 5 amino acids in the amino acid sequence represented by one of SEQ ID NO: 4 to SEQ ID NO: 23, SEQ ID NO: 38, and SEQ ID NO: 39, and having a pluripotent stem cell culturing property.

In the present specification, the polypeptide (a), the polypeptide (b), the polypeptide (c), and the polypeptide (d) are collectively referred to as a "specific polypeptide" in some cases. That is, the "specific polypeptide" refers to any one polypeptide or two or more polypeptides among the polypeptides (a) to (d).

<Polypeptide Composition>

The polypeptide composition contains at least one kind of polypeptide selected from the group consisting of the polypeptides (a) to (c) described above, in which the amount of a multimeric polypeptide, which is at least one kind of polypeptide selected from the group consisting of the polypeptides (a) to (c) and composed of two or more monomers held together by intermolecular cross-linking via cysteine residues included in the first region, is equal to or less than 20% by mass of the total mass of polypeptides contained in the polypeptide composition. Furthermore, in a case where the polypeptide composition is a composition containing the polypeptide (d) described above, the amount of a multimeric polypeptide, which is the polypeptide (d) and composed of two or more monomers held together by intermolecular cross-linking via cysteine residues included in the first region, is equal to or less than 20% by mass of the total mass of polypeptides contained in the polypeptide composition. Each polypeptide composition may contain both of at least one kind of polypeptide selected from the group consisting of the polypeptides (a) to (c) and the polypeptide (d). In this case, the amount of a multimeric polypeptide, which is at least one kind of polypeptide selected from the group consisting of the polypeptides (a) to (d) and composed of two or more monomers held together by intermolecular cross-linking via cysteine residues included in the first region, is equal to or less than 20% by mass of the total mass of polypeptides contained in the polypeptide composition.

That is, in a case where one or more cysteine residues are present in the first region included in the polypeptides (a) to (d), intermolecular cross-linking occurs between a cysteine residue of the first region and a cysteine residue of the first region present in other polypeptides, and in this way, a multimeric polypeptide composed of two or more monomers can be formed. If the polypeptide composition contains the multimer of the polypeptides (a) to (d) held together by intermolecular cross-linking via cysteine residues included in the first region at a ratio of higher than 20% of the total mass of polypeptides contained in the composition, the growth ability of the pluripotent stem cells is impaired. In the present specification, in a case where plural kinds of polypeptides are present in the composition, the ratio of the multimer contained in the composition to the total mass of polypeptides is the content (ratio) of the multimer with respect to the total mass of all of the polypeptides.

From the viewpoint of improving the growth ability of the pluripotent stem cells, the ratio of the multimer of the polypeptides (a) to (d) contained in the polypeptide composition is preferably equal to or less than 15% by mass, more preferably equal to or less than 10% by mass, and particularly preferably equal to or less than 5% by mass of the total mass of polypeptides contained in the composition.

In the polypeptide composition, from the viewpoint of the pluripotent stem cell culturing property, the amount of the multimeric polypeptide, which is different from the multimer resulting from intermolecular cross-linking via cysteine residues of the first region and composed of two or more monomers held together by intermolecular cross-linking via cysteine residues in any positions in the polypeptide, is preferably equal to or less than 20% by mass, more preferably equal to or less than 15% by mass, even more preferably equal to or less than 10% by mass, and still more preferably equal to or less than 5% by mass of the total mass of polypeptides contained in the composition.

The ratio of the multimer of the polypeptides (a) to (d) contained in the polypeptide composition can be calculated by, for example, analyzing the results of sodium dodecyl sulfate/polyacrylamide gel electrophoresis (SDS-PAGE) performed by a common method by using image analysis software such as "IMAGE J" (supplied by National Institutes of Health (NIH)).

From the viewpoint of accelerating and improving the growth of the pluripotent stem cells, the polypeptides (a) to (d) in the polypeptide composition more preferably include a polypeptide which is included in the first region and in which intramolecular cross-linking occurs between a cysteine residue corresponding to the $25^{th}$ amino acid residue included in the first region and represented by SEQ ID NO: 1 and a cysteine residue corresponding to the $31^{st}$ amino acid residue in the same amino acid sequence, and even more preferably include at least one kind of polypeptide among the polypeptides (a) to (d) in the first region and in each of which intramolecular cross-linking occurs between a cysteine residue corresponding to the $5^{th}$ amino acid residue included in the first region and represented by SEQ ID NO: 1 and a cysteine residue corresponding to the $9^{th}$ amino acid residue in the same amino acid sequence; between a cysteine residue corresponding to the $19^{th}$ amino acid residue and a cysteine residue corresponding to the $21^{st}$ amino acid residue in the same amino acid sequence; between a cysteine residue corresponding to the $25^{th}$ amino acid residue and a cysteine residue corresponding to the $31^{st}$ amino acid residue in the same amino acid sequence; and between a cysteine residue corresponding to the $32^{nd}$ amino acid residue and a cysteine residue corresponding to the $39^{th}$ amino acid residue in the same amino acid sequence.

The polypeptide composition of the present invention may contain a polypeptide other than the polypeptides (a) to (d). In a case where the polypeptide composition is a polypeptide composition containing at least one kind of polypeptide selected from the polypeptides (a) to (c), from the viewpoint of more efficiently obtaining the effects of the present invention, the total ratio of the polypeptides (a) to (d) contained in the composition is preferably equal to or greater than 85% by mass, more preferably equal to or greater than 90% by mass, even more preferably equal to or greater than 95% by mass, and particularly preferably equal to or greater than 99% by mass of the composition. Furthermore, in a case where the polypeptide composition is a polypeptide composition containing the polypeptide (d), from the viewpoint of more efficiently obtaining the effects of the present invention, the total ratio of the polypeptides (a) to (d) contained in the composition is preferably equal to or greater than 85% by mass, more preferably equal to or greater than 90% by mass, even more preferably equal to or greater than 95% by mass, and particularly preferably equal to or greater than 99% by mass of the composition.

From the viewpoint of the pluripotent stem cell culturing property, the binding constant between the polypeptide contained in the polypeptide composition and a plasminogen activator inhibitor-1 (PAI-1) is preferably greater than 0.06. It is known that a polypeptide in which intramolecular cross-linking occurs between the $25^{th}$ cysteine residue and the $30^{st}$ cysteine residue exhibits binding properties with respect to the plasminogen activator inhibitor-1 (PAI-1). Therefore, the lower the binding constant with respect to the PAI-1, the smaller the number of polypeptides in which intramolecular cross-linking occurs between the $25^{th}$ cysteine residue and the $31^{st}$ cysteine residue. From the viewpoint of accelerating the growth of the pluripotent stem cells, the biding constant between the polypeptide in the composition and the PAI-1 is preferably equal to or greater than 0.1, and more preferably equal to or greater than 0.22. The upper limit of the binding constant between the polypeptide in the composition and the PAI-1 is not particularly limited. However, the upper limit of the binding constant is preferably equal to or less than 1.0 because it means that a single PAI-1 molecule binds to every polypeptide.

The cysteine residue in a polypeptide tends to be cross-linked with other cysteine residues in the same polypeptide or with cysteine residues in other polypeptides. It is known that the occurrence of intermolecular cross-linking between the cysteine residue in a polypeptide and cysteine residues in other polypeptides can be controlled by adjusting the oxidation/reduction conditions, and examples of the method include those disclosed in Sinha N. K. et al., J Biol Chem. 250 pp. 8624-8629, 1975.

Specifically, the polypeptide composition can be obtained by a manufacturing method including a step of preparing a reaction solution by combining the intended polypeptides (a) to (d) with a denaturant such as urea or guanidine hydrochloride such that the concentration of the denaturant becomes 4 M to 8 M; a step of adding a reductant such as reduced glutathione or cysteine and an oxidant such as oxidized glutathione or cystine to the obtained reaction solution such that the reductant and the oxidant coexist at a predetermined ratio, for example, 10:1 to 2:1 (reductant: oxidant (molar ratio)); and a step of reducing the concentration of the denaturant in the reaction solution containing the reductant and the oxidant to 0 M to 0.5 M.

The polypeptide composition of the present invention may be a polypeptide composition containing at least one kind of polypeptide selected from the group consisting of the polypeptides (a) to (c), in which the amount of a multimeric polypeptide, which is composed of two or more monomers held together by intermolecular cross-linking via cysteine residues included in the polypeptide, is equal to or less than 20% by mass of the total mass of polypeptides contained in the composition. In the polypeptide composition of the present embodiment, the ratio of the multimer, in which intermolecular cross-linking is established through cysteine residues in any positions in the polypeptides (a) to (c), contained in the composition is equal to or less than 20% by mass of the total mass of polypeptides contained in the composition. Therefore, just as the polypeptide composition described above, the polypeptide composition of the present embodiment can improve the pluripotent stem cell growth property.

All of the matters described above regarding polypeptide compositions of other embodiments can be adopted as they are for the polypeptide (a) which can be contained in the polypeptide composition of the present embodiment, as long as the matters can be applied to the polypeptide (a) in the polypeptide composition of the present embodiment, and the preferred range thereof is also adopted as it is.

The polypeptide (b) which can be contained in the polypeptide composition of the present embodiment may have any sequence as long as it is a polypeptide having an amino acid sequence, which has identity of equal to or higher than 80% with the amino acid sequence represented by SEQ ID NO: 1, and having a pluripotent stem cell culturing property. Furthermore, the polypeptide (b) may not have the amino acid sequences (1-i) to (1-iii) described above. All of the matters regarding the identity with the amino acid sequence represented by SEQ ID NO: 1 and the matters described above regarding the polypeptide compositions of other embodiments, such as the amino acid sequence the polypeptide (b) may include and the GRAVY value, can be adopted as they are as long as the matters can be applied to the polypeptide (b) in the polypeptide composition of the present embodiment, and the preferred range thereof is also adopted as it is.

The polypeptide (c) which can be included in the polypeptide of the present embodiment may have any sequence as long as it is a polypeptide having an amino acid sequence, which is formed by deletion, substitution, or addition of one amino acid or plural amino acids in SEQ ID NO: 1, and having a pluripotent stem cell culturing property. Furthermore, the polypeptide (c) may not have the amino acid sequences (1-i) to (1-iii) described above. All of the matters described above regarding the polypeptide compositions of other embodiments, such as the number and type of the amino acids that undergo deletion, substitution, or addition in the amino acid sequence represented by SEQ ID NO: 1, the amino acid sequence the polypeptide (b) may include, and the GRAVY value, can be adopted as they are as long as the matters can be applied to the polypeptide (c) in the polypeptide composition of the present embodiment, and the preferred range thereof is also be adopted as it is.

<Culture Method for Pluripotent Stem Cells>

A culture method for pluripotent stem cells of the present invention includes culturing pluripotent stem cells in the presence of the polypeptide composition described above. According to the present culture method, pluripotent stem cells can grow efficiently.

From the viewpoint of accelerating and improving the growth of pluripotent stem cells and handleability, the culture method for pluripotent stem cells includes obtaining a polypeptide-coated culture surface by applying the polypeptide composition according to the present invention to a cell culture surface of a support (hereinafter, referred to as a culture surface preparation step) and culturing pluripotent stem cells by seeding the pluripotent stem cells onto the polypeptide-coated culture surface (hereinafter, referred to as a culture step).

The pluripotent stem cells according to the present invention are pluripotent stem cells of an animal that belongs to primates. Specifically, the pluripotent stem cells include embryonic stem cells (ES cells), induced pluripotent stem cells (iPS cells), somatic stem cells, cells from inner cell mass of fertilized eggs, early embryonic cells, and the like. One kind of these cells may be used singly, or if necessary, two or more kinds thereof may be used by being mixed together. The iPS cells include the cells described in Nature, 2007, July 19; Vol. 448, pp. 313-317; Cell, 2006, August 25; Vol. 126(4), pp. 663-676 and cells similar to the above cells.

Examples of the pluripotent stem cells preferably used in the present invention include iPS cells.

Examples of the animal that belongs to primates include a human being, a monkey, a gorilla, and the like. The animal that belongs to primates is preferably a human being congeneric with the polypeptides (a) to (d) to be used. As long as a component or a substance used in the present invention is a component or a substance derived from an animal that belongs to primates, it can be preferably used in the present invention as a component or a substance derived from a homogeneous animal.

The culture solution used for culture can be appropriately selected according to the type of the cells to be cultured. Any of known culture solution can be used, and examples thereof include Essential 8, DMEM, MEM, F 12, DME, RPMI 1640, MCDB 104 and 199, MCDB 153, L 15, SkBM, a Basal medium, and the like. Among these, Essential 8 is preferable.

To the above culture solutoin, various components that can be generally added, for example, glucose, fetal bovine serum (FBS), human serum, or antibiotics (penicillin, streptomycin, and the like) may be added. In a case where serum is added, the concentration thereof can be appropriately changed according to the state of culture at that time. However, generally, the concentration of serum can be 10% (v/v).

Among the above media, a medium is preferable which contains, as other components, water, a salt (an inorganic salt such as chloride, hydroxide, carbide, or the like of sodium, potassium, magnesium, or calcium and an organic salt such as sodium pyruvate), an amino acid (an essential amino acid and a nonessential amino acid), vitamin (riboflavin, biotin, cyanocobalamin, ascorbic acid, an ascorbic acid derivative, or the like), a trace elements (selenium, iron, zinc, copper, or the like), a carbon source (D-glucose or the like), FGF (basic fibroblast growth factor FGF-2 or the like), TGF-$\beta$, insulin, and transferrin.

In the culture method of the present invention, it is preferable that the pluripotent stem cells are cultured in the absence of a heterogeneous animal-derived component. In this way, a likelihood of the intermixing of a heterogeneous animal-derived foreign substance can be eliminated with high accuracy. Examples of the culture of pluripotent stem cells in the absence of a heterogeneous cell-derived component include the culture using a culture solution not containing a heterogeneous animal-derived component, the culture not using a heterogeneous animal-derived feeder cells, and the like.

Furthermore, in the culture method of the present invention, it is preferable that the pluripotent stem cells are cultured in the absence of a heterogeneous animal-derived component and a serum component. In this way, the intermixing of a heterogeneous animal-derived component can be more reliably prevented.

As the medium not containing the heterogeneous animal-derived component, a medium mixture composed of a hypoosmotic medium containing at least one kind of medium component such as a nonessential amino acid, glutamic acid, β-mercaptoethanol, FGF-2, TGF-β, insulin, or transferring can be used. Specifically, it is possible to use a medium such as TeSR2 (Stemcell Technologies Inc) and ESSENTIAL 8 (Life Technologies), but the present invention is not limited thereto.

The cells are cultured in an incubator under general culture conditions, for example, a temperature of 37° C. and a $CO_2$ concentration of 5% (v/v).

In the culture method and subculture method for pluripotent stem cells, it is possible to use a general medium which is used for retaining pluripotent stem cells. Specifically, examples of the method include mTeSR, TeSR2 (Stemcell Technologies Inc), and the like. The pluripotent stem cells are seeded into the medium by a common method. Herein, it is not necessary to use the same medium for a series of passages, and as long as the pluripotent stem cells can be kept undifferentiated, different media may be used.

In the culture surface preparation step, a polypeptide-coated culture surface is prepared by applying a coating solution, which contains the specific polypeptide, to a culture surface of a support. In this way, the culture surface can be coated with the specific polypeptide.

The total content of the specific polypeptide in the coating solution varies with the type and the size of the culture surface to be coated. However, from the viewpoint of the adsorbability with respect to the culture surface, the total content of the specific polypeptide is preferably 1 pmol/cm$^2$ to 1,000 mol/cm$^2$, and more preferably 100 mol/cm$^2$ to 300 pmol/cm$^2$. An aqueous medium used for preparing the coating solution is not particularly limited, and examples thereof include a phosphate buffered saline, a tris-buffer solution, ultrapure water, and the like.

In the coating operation, after being applied, the coating solution is held as it is for a certain period of time, for example, for about 30 minutes to 24 hours. In this way, the culture surface can be coated with the specific polypeptide without the need to perform a special treatment.

The culture step includes culturing pluripotent stem cells by seeding the pluripotent stem cells onto the polypeptide-coated culture surface.

The seeding density and the culture of the pluripotent stem cells are not particularly limited, and generally used conditions can be used as they are. For example, the cells may be seeded at a seeding density of about $1 \times 10^3$ cells/cm$^2$ to $1 \times 10^5$ cells/cm$^2$ and cultured under the aforementioned culture and subculture conditions. Furthermore, a cell mass with a diameter of 10 μm to 100 μm may be seeded at a seeding density of about 1 cell/cm$^2$ to 5 cells/cm$^2$ and cultured under the aforementioned culture and subculture conditions.

In this way, it is possible to excellently grow the pluripotent stem cells with excellent handleability on the culture surface coated with the specific polypeptide. Furthermore, in a case where the polypeptide (d) is used, it is possible to excellently grow the pluripotent stem cells while maintaining the undifferentiated state.

The pluripotent stem cells cultured in the presence of the specific polypeptide (preferably, in the absence of a heterogeneous animal-derived component and the like) can completely or greatly eliminate the likelihood of the intermixing of a foreign substance such as an antigenic substance derived from the sample or the like. Therefore, the pluripotent stem cells cultured by the culture method can secure sufficient safety when being used for medical purposes or for the purposes equivalent to medical purposes.

In addition, according to the culture method using the specific polypeptide, pluripotent stem cells can be cultured at lower costs and by a simpler operation. Therefore, the culture method can make a great contribution not only to the medical purposes but also to the demand in the research field.

<Culture Vessel>

In the present invention, a culture vessel means a vessel having a support which has a surface used for cell culture. As the support, those known as a support for cell culture in the related art can be used as they are. Examples of materials of the support may include plastic (for example, polystyrene, an acrylonitrile-butadiene-styrene resin, a polycarbonate resin, and a polyester resin), glass, a filter material with fine pores (for example, cellulose, nylon, glass fiber, polyester, and polycarbonate), a material for a bioreactor (may include hollow fiber tubes or microcarrier beads) used in batch cell culture, continuous cell culture, or genetic engineering (for example, a bioreactor), polyethylene terephthalate, TEFLON (registered trademark), ceramic and polymer materials relating thereto, and the like.

In addition, the aforementioned support may be a support of which the culture surface is coated with a plasma-polymerized thin film.

The shape of the culture vessel is not particularly limited, and the culture vessel may have any shape as long as it is applicable to the culture of pluripotent stem cells. Examples of vessels with such a shape include a multi-well plate (for example, a 6-well plate, a 12-well plate, a 24-well plate, and a 96-well plate), a culture dish (for example, a petri dish), a tube, a culture flask, a roller bottle, a flask for shake culture, and the like.

The culture vessel according to the present invention has a support having a cell culture surface and a polypeptide contained in a polypeptide composition disposed on the cell culture surface of the support.

The present culture vessel has a culture surface comprising the polypeptide in the polypeptide composition according to the present invention described above, that is, at least one kind of polypeptide selected from the group consisting of the polypeptides (a) to (d). Therefore, the specific polypeptide is excellently adsorbed onto the culture surface. Furthermore, in a case where pluripotent stem cells are seeded onto the specific polypeptide, pluripotent stem cells can grow with excellent handleability, and in a case where the polypeptide (d) is used, pluripotent stem cells can grow in a state of being kept undifferentiated.

Herein, the culture surface in the culture vessel means a surface to which cells can adhere at the time of seeding and growing the cells.

The culture vessel according to the present invention can be manufactured by a manufacturing method including preparing a vessel comprising a support having a cell culture surface (hereinafter, referred to as a "preparation step") and performing an adsorption treatment on the cell culture surface by applying at least one kind of polypeptide selected from the group consisting of the polypeptides (a) to (d) to the cell culture surface (hereinafter, referred to as a "adsorption treatment step"). In this way, the culture vessel according to the present invention can be obtained in a simple manner.

In the preparation step, the culture vessel comprising the support having the culture surface is prepared. In a case where the support has a plasma-polymerized thin film on the culture surface, the preparation step may include a step of forming the plasma-polymerized thin film on the support. As the method for forming the plasma-polymerized thin film, a common method may be used as it is.

The adsorption treatment step includes applying the specific polypeptide to the culture surface and holding the culture surface as it is. In the adsorption treatment step, the specific polypeptide should be adsorbed onto the culture surface by preparing an adsorbent solution containing the specific polypeptide in a predetermined amount, applying the adsorbent solution to the culture surface, and holding the culture surface as it is for a predetermined time.

In the adsorption treatment step, the matters described in the step of preparing the polypeptide-coated culture surface in the culture method can be applied as they are.

EXAMPLES

Hereinafter, the present invention will be specifically described based on examples, but the present invention is not limited thereto. Herein, unless otherwise specified, "%" is based on mass.

Reference Example 1

Preparation of Polypeptide

By a common method using PCR, gene sequences encoding each of the polypeptides RCP-1 to RCP-17 having the amino acid sequences shown in Tables 2 and 3 were amplified. Herein, RCP-11 corresponds to the sequence of natural human vitronectin. In Tables 2 and 3, the column of "NOTE" shows the position in the amino acid sequence (SEQ ID NO: 1) of natural human vitronectin corresponding to the amino acid sequence of each of the polypeptides. Here, in some cases, the amino acid sequence of each of the polypeptides include an amino acid sequence which is formed by the addition, deletion, or substitution occurring in the amino acid sequence of the natural human vitronectin within a range corresponding described in the tables. The amino acid sequences of RCP-1 to RCP-10 and RCP-17 are the same as each other, except that methionine is on the N-terminal in each of the amino acid sequences represented by SEQ ID NO: 4 to SEQ ID NO: 13 and SEQ ID NO: 38.

For RCP-1 to RCP-10 and RCP-17, target genes were inserted into pET-28b(+), which was cleaved in advance by being treated with NCOL (TAKARA BIO INC.), by using an InFusion ADVANTAGE PCR CLONING KIT (registered trademark, Clontech Laboratories, Inc), thereby constructing the respective expression vectors. For RCP-11 to RCP-16, target genes were inserted into PGEX-6P-1 (GE Healthcare Japan Corporation), which was cleaved in advance by being treated with BamHI (TAKARA BIO INC.), in the same manner as described above, thereby constructing the respective expression vectors. The sequences of the expression vectors were checked by sequence analysis.

TABLE 2

| | Amino acid sequence | SEQ ID No. | NOTE |
|---|---|---|---|
| RCP-1 | MDQESCKGRCTEGFNVDKKCQCDELCSYYQSCCTDYTAECKPQVTRGDVFTMPEDEPSQE ECEGSSLSAVFEHFAMMQRDSWEDIFELLFWGRTSAGTRQPQFISRDWHGVPGQVDAAMA GRIYISGMAPRPSLAKKQRFRHRNRKGYRSQRGHSRGRNQNSRRPSRATWLSLFSSEESNL GANNYDDYRMDWLVPATCEPIQSVFFFSGDKYYRVNLRTRRVDTVDPPYPRSIAQYWLGCF APGHL | 14 | 1-55<br>269-459 |
| RCP-2 | MDQESCKGRCTEGFNVDKKCQCDELCSYYQSCCTDYTAECKPQVTRGDVFTMPEDEPRPS LAKKQRFRHRNRKGYRSQRGHSRGRNQN | 15 | 1-55<br>342-373 |
| RCP-3 | MDQESCKGRCTEGFNVDKKCQCDELCSYYQSCCTDYTAECKPQVTRGDVFTMPEDEGVP GQVDAAMAGRIYISGMAPRPSLAKKQRFRHRNRKGYRSQRGHSRGRNQN | 16 | 1-55<br>322-341<br>342-373 |
| RCP-4 | MDQESCKGRCTEGFNVDKKCQCDELCSYYQSCCTDYTAECKPQVTRGDVFTMPEDEQPQ FISRDWHGVPGGVDAAMAGRIYISGMAPRPSLAKKQRFRHRNRKGYRSQRGHSRGRNQN | 17 | 1-55<br>312-341<br>342-373 |
| RCP-5 | MDQESCKGRCTEGFNVDKKCQCDELCSYYQSCCTDYTAECKPQVTRGDVFTMPEDEFWG RTSAGTRQPQFISRDWHGVPGQVDAAMAGRIYISGMAPRPSLAKKQRFRHRNRKGYRSQR GHSRGRNQN | 18 | 1-55<br>302-341<br>342-373 |
| RCP-6 | MDQESCKGRCTEGFNVDKKCQCDELCSYYQSCCTDYTAECKPQVTRGDVFTMPEDESQEE SEGSSLSAVFEHFAMMQRDSWEDIFELLFWGRTSAGTRQPQFISRDWHGVPGQVDAAMAG RIYISGMAPRPSLAKKQRFRHRNRKGYRSQRGHSRGRNQNSRRPSRATWLSLFSSEESNLG ANNYDDYRMDWLVPATSEPIQSVFFFSGDKYYRVNLRTRRVDTVDPPYPRSIAQYWLGSPA PGHL | 19 | 1-55<br>270-459<br>C274S<br>C411S<br>C453S |
| RCP-7 | MDQESCKGRCTEGFNVDKKCQCDELCSYYQSCCTDYTAECKPQVTRGDVFTMPEDESQEE SEGSSLSAVFEHFAMMQRDSWEDIFELLFWGRTSAGTRQPQFISRDWHGVPGQVDAAMAG RIYISGMAPRPSLAKKQRFRHRNRKGYRSQRGHSRGRNQN | 20 | 1-55<br>270-373<br>C274S |
| RCP-8 | MDQESCKGRCTEGFNVDKKCQCDELCSYYQSCCTDYTAECKPQVTRGDVFTMPEDESQEE SEGSSLSAVFEHFAMMQRDSWEDIFELLFWGRTSAGTRQPQFISRDWHGVPGQVDAAMAG RIYISGMAPRPSLAKKQRFRHRNRKGYRSQRGHSRGRNQNSRRPSR | 21 | 1-55<br>270-373<br>374-379<br>C274S |
| RCP-9 | MDQESCKGRCTEGFNVDKKCQCDELCSYYQSCCTDYTAECKPQVTRGDVFTMPEDESQEE SEGSSLSAVFEHFAMMQRDSWEDIFELLFWGRTSAGTRQPQFISRDWHGVPGQVDAAMAG RIYISGMAPRPSLAKKQRFRHRNRKGYRSQRGHSRGRNQNSRRPSRATWLSLFSSEE | 22 | 1-55<br>270-373<br>374-389<br>C274S |

TABLE 2-continued

| Amino acid sequence | SEQ ID No. | NOTE |
|---|---|---|
| RCP-10 MDQESCKGRCTEGFNVDKKCQCDELCSYYQSCCTDYTAECKPQVTRGDVFTMPEDESQEE<br>SEGSSLSAVFEHFAMMQRDSWEDIFELLFWGRTSAGTRQPQFISRDWHGVPGQVDAAMAG<br>RIYISGMAPRPSLAKKQRFRHRNRKGYRSQRGHSRGRNQNSRRPSRATWLSLFSSEESNLG<br>ANNYD | 23 | 1-55<br>270-373<br>374-399<br>C274S |
| RCP-17 MDQESCKGRCTEGFNVDKKCQCDELCSYYQSCCTDYTAECKPQVTRGDVFTMPEDESQEE<br>SEGSEDIFELLFWGRTSAGTRQPQFISRDWHGVPGQVDAAMAGRIYISGMAPRPSLAKKQRF<br>RHRNRKGYRSQRGHSRGRNQN | 39 | 1-55<br>270-277<br>295-341<br>342-373<br>C274S |

TABLE 3

| | Amino acid sequence | SEQ ID No. | NOTE |
|---|---|---|---|
| RCP-11 | GPLGDQESCKGRCTEGFNVDKKCQCDELCSYYQSCCTDYTAECKPQVTRGDVFTMPEDEY<br>TVYDDGEEKNNATVHEQVGGPSLTSDLQAQSKGNPEQTPVLKPEEEAPAPEVGASKPEGID<br>SRPETLHPGRPQPPAEEELCSGKPFDAFTDLKNGSLFAFRGQYCYELDEKAVRPGYPKLIRD<br>VWGIEGPIDAAFTRINCQGKTYLFKGSQYWRFEDGVLDPDYPRNISDGFDGIPDNVDAALAL<br>PAHSYSGRERVYFFKGKQYWEYQFQHQPSQEECEGSSLSAVFEHFAMMQRDSWEDIFELLF<br>WGRTSAGTRQPQFISRDWHGVPGQVDAAMAGRIYISGMAPRPSLAKKQRFRHRNRKGYRS<br>QRGHSRGRNQNSRRPSRATWLSLFSSEESNLGANNYDDYRMDWLVPATCEPIQSVFFFSG<br>DKYYRVNLRTRRVDTVDPPYPRSIAQYWLGCPAPGHL | 24 | 1-459 |
| RCP-12 | GPLGDQESCKGRCTEGFNVDKKCQCDELCSYYQSCCTDYTAECKPQVTRGDVFTMPEDEY<br>TVYDDGEEKNNATVHEQVGGPSLTSDLQAQSKGNPEQTPVLKPEEEAPAPEVGASKPEGID<br>SRPETLHPGRPQPPAEEELCSGKPFDAFTDLKNGSLFAFRGQYCYELDEKAVRPGYPKLIRD<br>VWGIEGPIDAAFTRINCQGKTYLFKGSQYWRFEDGVLDPDYPRNISDGFDGIPDNVDAALAL<br>PAHSYSGRERVYFFKGKQYWEYQFQHQ | 25 | 1-55<br>56-268 |
| RCP-13 | GPLGDQESCKGRCTEGFNVDKKCQCDELCSYYQSCCTDYTAECKPQVTRGDVFTMPEDEY<br>TVYDDGEEKNNATVHEQVGGPSLTSDLQAQSKGNPEQTPVLKPEEEAPAPEVGASKPEGID<br>SRPETLHPGRPQP | 26 | 1-55<br>56-130 |
| RCP-14 | GPLGDQESCKGRCTEGFNVDKKCQCDELCSYYQSCCTDYTAECKPQVTRGDVFTMPEDE | 27 | 1-55 |
| RCP-15 | GPLGYTVYDDGEEKNNATVHEQVGGPSLTSDLQAQSKGNPEQTPVLKPEEEAPAPEVGASK<br>PEGIDSRPETLHPGRPQPPAEEELCSGKPFDAFTDLKNGSLFAFRGQYCYELDEKAVRPGYP<br>KLIRDVWGIEGPIDAAFTRINCQGKTYLFKGSQYWRFEDGVLDPDYPRNISDGFDGIPDNVDA<br>ALALPAHSYSGRERVYFFKGKQYWEYQFQHQPSQEECEGSSLSAVFEHFAMMQRDSWEDI<br>FELLFWGRTSAGTRQPQFISRDWHGVPGQVDAAMAGRIYISGMAPRPSLAKKQRFRHRNRK<br>GYRSQRGHSRGRNQNSRRPSRATWLSLFSSEESNLGANNYDDYRMDWLVPATCEPIQSVF<br>FFSGDKYYRVNLRTRRVDTVDPPYPRSIAQYWLGCPAPGHL | 28 | 56-459 |
| RCP-16 | GPLGPSQEECEGSSLSAVFEHFAMMQRDSWEDIFELLFWGRTSAGTRQPQFISRDWHGVPG<br>QVDAAMAGRIYISGMAPRPSLAKKQRFRHRNRKGYRSQRGHSRGRNQNSRRPSRATWLSL<br>FSSEESNLGANNYDDYRMDWLVPATCEPIQSVFFFSGDKYYRVNLRTRRVDTVDPPYPRSI<br>AQYWLGCPAPGHL | 29 | 269-459 |

The prepared expression vectors of RCP-1 to RCP-10 and RCP-17 were transformed into BL21(DE3)pLysS (Novagen) by a common method, applied to a kanamycin-containing LB plate, and incubated for 16 hours at 37° C. By a colony direct PCR method, the state where the vectors were introduced into the cells was checked. Thereafter, 1 mM IPTG (isopropyl-β-D-thiogalactopyranoside, Wako Pure Chemical Industries, Ltd.) was added thereto, and the cells were cultured by being shaken for 5 hours at 37° C., thereby inducing the expression of the polypeptides.

The bacterial cells were collected through a centrifugal treatment and resuspended in a washing buffer (20 mM Tris, 150 mM NaCl, pH 7.6). Through sonication, the bacterial cells were fragmented and then subjected to centrifugation for 30 minutes at 4° C. and 15,000 rpm, and an insoluble fraction was collected. The bacterial cells were washed with a washing buffer containing 0.5% by mass of Triton ×100, then resuspended in a low-concentration urea buffer (Low Urea Buffer: 20 mM Tris, 150 mM NaCl, 2 M urea, pH 7.6), and subjected to a sonication treatment. Through a centrifugation treatment, an insoluble fraction was collected, a high-concentration urea buffer (High Urea Buffer: 20 mM Tris, 150 mM NaCl, 8 M urea, pH 7.6) was then added thereto, and the insoluble fraction was solubilized through a sonication treatment.

The solution obtained by the method described above that contained a target peptide was purified by using AKTA Explorer 100 (trade name, GE Healthcare Japan Corporation) and HiTrap Heparin HP 5 ml (GE Healthcare Japan Corporation). By performing stepwise elution using a high-concentration urea buffer as a binding buffer and a high-salt concentration adjusting buffer (20 mM Tris, 1 M NaCl, 8 M urea, pH 7.6) as an elution buffer, the target polypeptide was purified.

The expression vectors of RCP-11 to RCP-16 prepared as above were transformed into BL21 (Novagen) by a common method, applied to an ampicillin-containing LB plate, and incubated for 16 hours at 37° C. By a colony direct PCR method, the state where the vectors were introduced into the cells was checked. Thereafter, in the ampicillin-containing LB to which 100 μM IPTG was added, and the cells were cultured by being shaken for 24 hours at 20° C., thereby inducing the expression of the polypeptides.

The bacterial cells were collected, resuspended in a B-PER (registered trademark) Bacterial Protein Extraction Reagent in Phosphate Buffer (trade name, Thermo Fisher Scientific Inc.), and then fragmented through sonication. By performing centrifugation for 30 minutes at 4° C. and 15,000 rpm, an insoluble fraction was removed, and the supernatant was purified by using AKTA Explorer 100 and GSTrap HP 5 ml×2 (trade name, GE Healthcare Japan Corporation). The eluted fraction was desalted by using Hiprep 26/10 Desalting (trade name, GE Healthcare Japan Corporation). Furthermore, a protease (PreScission Protease) for cleaving a GST fusion protein was added thereto in a solution amount of 1/2,000, and the resultant was incubated for 24 hours at 4° C., thereby cleaving the GST tag. The resultant was purified again by using GSTrap HP 5 ml×2, and the cleaved GST tag was removed by being adsorbed onto a column. The fraction passing through the column was dialyzed using Slide-A-Lizer (trade name, 3.5 K MWCO.: Thermo Fisher Scientific Inc., the same device will be used hereinafter) and substituted with PBS.

The polypeptide of RCP-1 obtained as above was subjected to electrophoresis by using READY GEL (12.5%, Bio-Rad Laboratories, Inc.) and stained with a GELCODE™ BLUE STAIN REAGENT (trade name, Thermo Scientific Inc.). As a result, a single band could be confirmed at a site corresponding to a molecular weight of 28.3 kDa expected from the amino acid sequence. The same results were obtained from other polypeptides.

For RCP-1 to RCP-10 and RCP-17, each of the purified polypeptide solutions was dialyzed using SLIDE-A-LIZER (trade name, 3.5 K MWCO.). Basically, by using a dialysis buffer (PBS, 1.5 M NaCl, 0.5 M L-arginine, 1 mM EDTA, pH 7.4) as an outer dialysate, urea was removed by stepwise dialysis. The concentration of the end-product of dialysis was calculated from the absorbence at 280 nm by using NANODROP (trade name, Thermo Fisher Scientific Inc.). Table 4 shows whether or not aggregation occurred after dialysis.

Furthermore, the indices of hydrophobicity determined for each of the amino acids were summed up, the obtained value was divided by the number of the amino acids, and the outcome was determined as the GRAVY value (see Kyte J., Doolittle R. F. (1982), J. Mol. Biol, 157: 105-132). The GRAVY value is an index of the hydrophilicity and hydrophobicity of a polypeptide calculated from the degree of hydrophobicity of the amino acids contained in each polypeptide. The greater the GRAVY value, the more the polypeptide is hydrophobic, and the smaller the GRAVY value, the more the polypeptide is hydrophilic. The results are shown in Table 4.

Whether or not aggregation was occurred was evaluated based on the scale of G, A, and B as shown below. The results are summarized in Table 4.

G: The formation of an aggregate was not observed.
A: The formation of particles having a particle size of about 100 nm was observed.
B: The formation of an aggregation of particles having a particle size of equal to or greater than 1 mm was visually observed.

TABLE 4

|  | GRAVY | Number of amino acids | Aggregation |
| --- | --- | --- | --- |
| RCP-1 | −0.835 | 247 | A |
| RCP-2 | −1.516 | 88 | G |
| RCP-3 | −1.124 | 108 | G |
| RCP-4 | −1.150 | 118 | G |
| RCP-5 | −1.124 | 128 | G |
| RCP-6 | −0.875 | 246 | A |
| RCP-7 | −0.979 | 160 | A |
| RCP-8 | −1.045 | 166 | A |
| RCP-9 | −0.958 | 176 | B |
| RCP-10 | −0.971 | 186 | B |
| RCP-17 | −1.072 | 143 | A |

From Table 4, it is understood that although each of RCP-2 to RCP-5, RCP-7, RCP-8, and RCP-17 is a polypeptide consisting of about 80 to 170 amino acid residues, and aggregation easily occurs in the polypeptide, the occurrence of aggregation is inhibited because the GRAVY value thereof is within a range of −1.70 to −0.975.

Reference Example 2

<Evaluation of Adsorbability with Respect to Culture Dish>

Each of the polypeptides obtained as above was diluted with a predetermined buffer such that they could be added to wells at a predetermined final concentration of 0 pmol/cm$^2$ to 200 pmol/cm$^2$. Thereafter, each of the polypeptides was added in an amount of 64 μL to a plasma-treated 96-well plate made of polystyrene (Tissue Culture-Treated, Falcon). Each of the polypeptides was allowed to adsorbed onto the plate by being incubated for 2 hours at 37° C., and then the wells were washed twice with PBS, thereby obtaining surfaces coated with each of the polypeptides of RCP-1 to RCP-16.

Among the surfaces coated with each of the polypeptides obtained as above, the surfaces coated with RCP-1 and RCP-11 to RCP-16 were applied with 64 μL of a borate buffer and 64 μL of 1 N NaOH, followed by incubation for 24 hours at 80° C. and 100% humidity. After the resultant was air-cooled, 75 μL of a borate buffer was added to each well, and 50 μL of a reaction solution obtained by mixing OPA (o-phthalaldehyde: Wako Pure Chemical Industries, Ltd./methanol solution (160 mg/ml)) with NAC (N-acetyl-L-cysteine: Wako Pure Chemical Industries, Ltd.)/borate buffer solution (2 mg/ml) at a ratio of 1:100 (mass ratio) was further added thereto. After incubation for 30 minutes at 40° C., the fluorescence intensity thereof was measured by using an ENVISION MULTILABEL COUNTER (trade name, PerkinElmer Inc.) (excitation 355 nm/fluorescence 486 nm). A calibration curve was separately prepared from each of the polypeptide solutions so as to calculate the amount of the polypeptide adsorbed. The results are shown in FIG. 1. In FIG. 1, a black rhombus indicates RCP-1, a black square indicates RCP-11, a black triangle indicates RCP-12, a black circle indicates RCP-13, a white rhombus indicates RCP-14, a white square indicates RCP-15, and a white triangle indicates RCP-16.

From FIG. 1, it is understood that among the polypeptides used in the test, the polypeptides of RCP-1, RCP-15, and RCP-16 including PRPSLAKKQRFRHRNRKGYR-SQRGHSRGRNQN (SEQ ID NO: 3 [amino acid sequence consisting of the 342$^{nd}$ to 373$^{rd}$ amino acid residues in SEQ ID NO: 1]) exhibit excellent adsorbability with respect to the plate that is equivalent to the adsorbability of RCP-11 having the sequence of human vitronectin. It is also understood that, in contrast, the amount of RCP-13 and RCP-14 not including PRPSLAKKQRFRHRNRKGYRSQRGHSR-GRNQN (SEQ ID NO: 3) adsorbed onto the plate is small and about ¼ of the amount of the polypeptide including the aforementioned sequence adsorbed onto the plate.

Reference Example 3

<Cell Adhesiveness Evaluation 1>

The cell adhesiveness of human iPS cells ("Tic": Cell No. JCRB 1331: from National Institute of Biomedical Innovation. [567-0085, 7-6-8 Asagi Saito Ibaraki-City Osaka]) with respect to the aforementioned polypeptides was evaluated in the following manner.

As feeder cells for retaining the human iPS cells, EMBRYOMAX (registered trademark) (early mouse embryonic fibroblasts: resistant to hygromycin, treated with mitomycin C, derived from C57/BL6, third passage) (Millipore Corporation) was used. By using DMEM (Invitrogen) and a 10% (v/v) fetal bovine serum medium, the feeder cells were cultured for 24 hours and attached to a T25 flask (trade name, Corning Incorporated). As a medium for the human iPS cells, the one obtained by adding FGF-2 (Sigma-Aldrich Co, LLC.) to a medium composed as shown in Table 5 at a final concentration of 10 ng/ml was used.

TABLE 5

| Composition | Maker | Amount |
|---|---|---|
| KO—DMEM/F12 | Invitrogen | 400 ml |
| Non-Essential Amino Acid Solution | | 4 ml |
| L-Glutamine | | 5 ml |
| Knock Out Serum Replacement | | 100 ml |
| 2-mercaptoethanol 55 mM | Wako Pure Chemical Industries, Ltd. | 0.925 ml |
| Total | | About 500 ml |

By using the aforementioned medium, the human iPS cells were retained and cultured in a 5% (v/v, the same unit will be used hereinafter) $CO_2$ incubator at 37° C. Except for the day after the seeding of the iPS cells, the medium was replaced every day. The subculture operation was performed by exfoliating the cells by using DISPASE (registered trademark) II (neutral protease Grade II, Roche) and separating the cells in an appropriate size by a pipetting operation.

The iPS cells cultured as described above were treated with TRYPLE SELECT (trade name, Invitrogen) for 5 minutes at 37° C. and separated into a single cell. After being subjected to centrifugation for 2 minutes at 300 rpm, the cells were collected and suspended in TESR2 (trade name, a medium not containing a heterogeneous animal-derived component and a serum component, STEMCELL Technologies.) containing Y-27362 ((R)-(+)-trans-N-(4-pyridyl)-4-(1-aminoethyl)-cyclohexanecarboxamide.2HCl.$H_2O$, an Rho binding kinase inhibitor, Wako Pure Chemical Industries, Ltd.) at a final concentration of 10 μM.

Samples 1 to 17 were prepared to which each of RCP-1 to RCP-10, RCP-17, RCP-11, RCP-15, RCP-16, and control including human vitronectin (extracted from human blood plasma, BD Biosciences) and recombinant laminin (rLaminin-5: Oriental Yeast Co., ltd. and HUMAN RECOMBINANT LAMININ-511: BIOLAMINA AB) was added at the concentration shown in Table 6. The samples were added to the respective wells of a 96-well plate and adsorbed onto the plate by being held for 2 hours at 37° C. Into the respective wells of the 96-well plate treated with the peptides, iPS cells were seeded at a cell density of 30,000 cells/well. After the cells were cultured for 24 hours, the nonadhesive cells were washed off with PBS, and only the adhesive cells were immobilized by using 4% paraformaldehyde (Wako Pure Chemical Industries, Ltd.). By using an ATTOPHOS (registered trademark) AP FLUORESCENT SUBSTRATE SYSTEM (Promega Corporation), the ALP activity was calculated, and from the calibration curve, the number of undifferentiated iPS cells having the ALP activity was calculated. The results are shown in Table 6. In Table 6, the cell adhesion rate is expressed as a relative value calculated by regarding the cell adhesion rate obtained from the sample 15 using natural vitronectin as being 100. n=3.

TABLE 6

| | Peptide type | Added amount | Cell adhesion rate (%) |
|---|---|---|---|
| Sample 1 | RCP-1 | 200 pmol/cm$^2$ | 109.3 ± 5.3 |
| Sample 2 | RCP-2 | 20 μg/cm$^2$ | 98.7 ± 6.2 |
| Sample 3 | RCP-3 | 20 μg/cm$^2$ | 106.1 ± 4.5 |
| Sample 4 | RCP-4 | 20 μg/cm$^2$ | 100.1 ± 4.5 |
| Sample 5 | RCP-5 | 10 μg/cm$^2$ | 94.1 ± 6.5 |
| Sample 6 | RCP-6 | 20 μg/cm$^2$ | 92.8 ± 4.4 |
| Sample 7 | RCP-7 | 5 μg/cm$^2$ | 88.6 ± 8.1 |
| Sample 8 | RCP-8 | 5 μg/cm$^2$ | 89.2 ± 1.4 |
| Sample 9 | RCP-9 | 20 μg/cm$^2$ | 95.5 ± 10.2 |
| Sample 10 | RCP-10 | 20 μg/cm$^2$ | 93.0 ± 7.8 |
| Sample 11 | RCP-17 | 5 μg/cm$^2$ | 95.9 ± 4.6 |
| Sample 12 | RCP-11 | 200 pmol/cm$^2$ | 93.5 ± 7.9 |
| Sample 13 | RCP-15 | 200 pmol/cm$^2$ | 13.2 ± 3.4 |
| Sample 14 | RCP-16 | 200 pmol/cm$^2$ | 9.4 ± 2.9 |
| Sample 15 | Natural vitronectin | 130 pmol/cm$^2$ | 100 ± 5.5 |
| Sample 16 | rLaminin-5 | 3.2 μg/cm$^2$ | 155.7 |
| Sample 17 | Laminin-511 | 5.0 μg/cm$^2$ | 142.0 |

As shown in Table 6, RCP-1 to RCP-10, RCP-17, and RCP-11, which had the $1^{st}$ to $44^{th}$ amino acids of the sequence represented by SEQ ID NO: 1, and natural human vitronectin were excellent in the cell adhesion rate of the iPS cells. Particularly, the cell adhesion rate was higher in RCP-1 to RCP-10 and RCP-17, which did not include a portion of the $56^{th}$ to $268^{th}$ amino acids of the sequence represented by SEQ ID NO: 1 or included none of the above amino acids, than in RCP-11 having the same amino acid sequence as the natural human vitronectin. Therefore, it is understood that a sequence important for the cell adhesion is present in the $1^{st}$ to $44^{th}$ amino acids of the sequence represented by SEQ ID NO: 1.

Reference Example 4

<Cell Adhesiveness Evaluation 2>

The polypeptides shown in Table 7 were synthesized by an Fmoc solid-phase synthesis method. A surface onto which natural vitronectin was adsorbed at a concentration of 130 pmol/cm$^2$ was prepared, and then a cell suspension to which 100 μM of the aforementioned synthetic polypeptides were added was seeded into wells at a ratio of 30,000 cells/well. The number of adhesive cells 24 hours after seeding was calculated in the same manner as in <Cell adhesiveness evaluation 1>, and the results are shown in Table 7. In Table 7, the cell adhesion rate is expressed as a relative value calculated by regarding the cell adhesion rate obtained by using a culture solution not containing the synthetic polypeptides as being 100%. n=3.

TABLE 7

| Sequence of synthetic peptide | | Cell adhesion rate (%) | SEQ ID No. |
|---|---|---|---|
| Peptide-1 | DQESCKGRCTEGFNVDKKCQ | 91.8 ± 1.2 | 30 |
| Peptide-2 | KGRCTEGFNVDKKCQCDELC | 92.7 ± 19.6 | 31 |
| Peptide-3 | EGFNVDKKCQCDELCSYYQS | 102.5 ± 4.2 | 32 |
| Peptide-4 | DKKCQCDELCSYYQSCCTDY | 63.8 ± 11.6 | 33 |
| Peptide-5 | CCTDYTAECKPQVTRGDVFT | 70.5 ± 7.1 | 34 |
| Peptide-6 | TAECKPQVTRGDVFTMPEDE | 52.7 ± 10.3 | 35 |
| Peptide-7 | CCTDYTAECKPQVTRGEVFT | 86.7 ± 7.1 | 36 |
| Peptide-8 | TAECKPQVTRGEVFTMPEDE | 83.8 ± 14.8 | 37 |

From Table 7, it is understood that while the adhesion of cells to the natural vitronectin is significantly hindered by the addition of Peptides-4, 5, and 6 including CSYYQSC (SEQ ID NO: 2) or RGD, the adhesion of cells is not hindered by the addition of Peptides-1, 2, and 3 not including CSYYQSC (SEQ ID NO: 2) and RGD and Peptides-7 and 8 obtained by substituting the RGD sequence of Peptides-5 and 6 with RGE. Accordingly, it is understood that the polypeptide exhibits cell adhesion ability when the polypeptide includes at least one of CSYYQSC (SEQ ID NO: 2) and RGD.

<Reference Example 5>

<Growth Evaluation>

Figure 2:
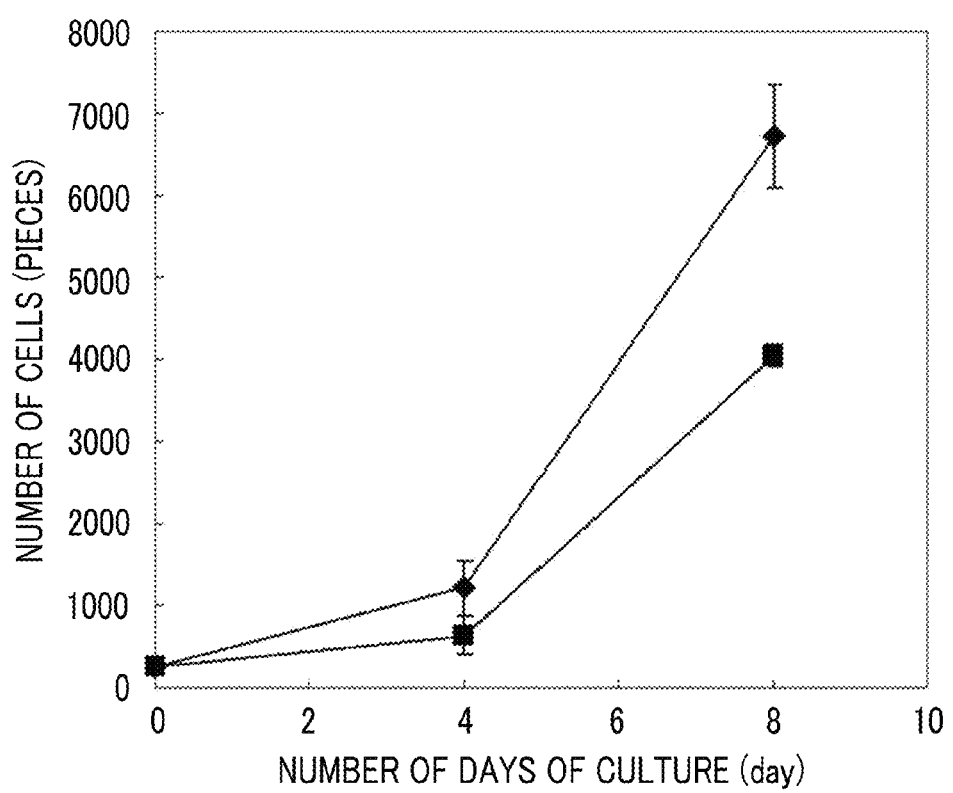
FIG. 2 is a graph showing growth curves of iPS cells using each polypeptide in reference examples of the present invention.

The iPS cells collected in the same manner as in <Cell adhesiveness evaluation 1> were seeded into a 96-well plate, onto which RCP-1, RCP-11, and natural human vitronectin were adsorbed, at a ratio of 250 cells/well and cultured for 8 days in a 5% $CO_2$ incubator at 37° C. The number of adhesive cells after different days of culture was measured in the same manner as in <Cell adhesiveness evaluation 1>, thereby obtaining growth curves. FIG. 2 shows the growth curves. In FIG. 2, a black rhombus indicates a case using RCP-1, and a black square indicates a case using RCP-11.

By adding RCP-1 to RCP-10, RCP-17, and Human Recombinant Laminin-511 as control at the concentration shown in Table 8, samples 1 to 12 were prepared. The samples were seeded into a 96-well plate, onto which each of the polypeptides was adsorbed in the same manner as in <Cell adhesiveness evaluation 1>, at a ratio of 5,000 cells/well and cultured for 3 days in a $CO_2$ incubator at 37° C. The number of cells after 3 days was calculated in the same manner as in <Cell adhesiveness evaluation 1>. The results are shown in Table 8.

TABLE 8

| | Peptide type | Added amount | Number of cells after 3 days (%) |
|---|---|---|---|
| Sample 1 | RCP-1 | 80 μg/cm² | 100.0 |
| Sample 2 | RCP-2 | 20 μg/cm² | 81.7 |
| Sample 3 | RCP-3 | 20 μg/cm² | 109.7 |
| Sample 4 | RCP-4 | 20 μg/cm² | 120.7 |
| Sample 5 | RCP-5 | 10 μg/cm² | 121.2 |
| Sample 6 | RCP-6 | 20 μg/cm² | 70.5 |
| Sample 7 | RCP-7 | 5 μg/cm² | 89.9 |
| Sample 8 | RCP-8 | 5 μg/cm² | 171.0 |
| Sample 9 | RCP-9 | 20 μg/cm² | 105.8 |

TABLE 8-continued

| | Peptide type | Added amount | Number of cells after 3 days (%) |
|---|---|---|---|
| Sample 10 | RCP-10 | 20 μg/cm² | 101.9 |
| Sample 11 | RCP-17 | 5 μg/cm² | 153.5 |
| Sample 12 | Laminin-511 | 1.28 μg/cm² | 56.8 |

As shown in FIG. 2, RCP-1 showed higher cell growth properties compared to RCP-11 having the amino acid sequence of the natural vitronectin, and on Day 8 of culture, the number of cells in the case using RCP-11 was about ⅓ of the number of cells in the case where RCP-1 was used. From the increase and decrease in the obtained number of cells, the doubling time was calculated. As a result, it was confirmed that it takes 46.4±2.1 hours for the number of cells to be doubled in a case where RCP-1 is used, and 67.7±2.1 hours in a case where RCP-11 is used.

From Table 8, it is understood that all of RCP-1 to RCP-10 and RCP-17 show a higher cell growth rate compared to laminin which is the extracellular matrix just like vitronectin. Furthermore, it is understood that even if the $274^{th}$ cysteine residue in SEQ ID NO: 1 was substituted with a serine residue, the same high cell growth rate as described above is obtained.

From the results shown in FIG. 2 and Table 8, it is understood that, surprisingly, RCP-1 to RCP-10 and RCP-17, which include a sequence effective for the cell growth and the adsorption onto the culture dish but do not include a sequence corresponding to a portion or the entirety of the $56^{th}$ to $268^{th}$ amino acids of natural human vitronectin, have a growth ability higher than that of RCP-11 having the same sequence as the human vitronectin and Laminin-511 as a comparative example.

Furthermore, from Table 8, it is understood that all of RCP-1 to RCP-10 and RCP-17 including both the sequences of CSYYQSC (SEQ ID NO: 2) and RDG and the sequence of PRPSLAKKQRFRHRNRKGYRSQRGHSRGRNQN (SEQ ID NO: 3) show high cell growth properties.

<Reference Example 6>

<Cell Adhesiveness Evaluation 3>

The cell adhesiveness was evaluated in the same manner as in <Cell adhesiveness evaluation 1>, except that RCP-1 was used after the concentration thereof was adjusted to 125 pmol/cm² to 1,000 pmol/cm² by using PBS. The results are shown in Table 9. In Table 9, the cell adhesion rate is expressed as relative value calculated by regarding a cell adhesion rate with respect to the culture vessel, onto which natural vitronectin is adsorbed at a concentration of 130 pmol/cm², as being 100. N=3.

TABLE 9

| Peptide type | Added amount | Cell adhesion rate (%) |
|---|---|---|
| RCP-1 | 1000 pmol/cm² | 98.5 ± 17.2 |
| RCP-1 | 500 pmol/cm² | 108.8 ± 23.0 |
| RCP-1 | 250 pmol/cm² | 89.2 ± 10.6 |
| RCP-1 | 125 pmol/cm² | 90.3 ± 25.3 |
| Natural vitronectin | 130 pmol/cm² | 100 ± 5.5 |

As shown in Table 9, in a case where the amount of RCP-1 added was equal to or greater than 125 pmol/cm², the adhesiveness of iPS cells with respect to RCP-1 was equivalent to the cell adhesion rate of the natural vitronection.

Reference Example 7

<Evaluation of Maintenance of Undifferentiated State> iPS cells collected in the same manner as in <Cell adhesiveness evaluation 1> were suspended in TeSR2. The iPS cells were seeded into 6-well plate (Tissue culture-treated, Falcon), onto which each of the samples 1, 2, 5, 6, and 7 used in <Cell adhesiveness evaluation 1> was adsorbed in the same manner as in <Cell adhesiveness evaluation 1>, and cultured in a $CO_2$ incubator at 37° C. Except for the day after the seeding, the medium was replaced every day. In the same method as described above, the cells were subcultured every six days. FIGS. 3A to 3E show forms of the iPS cells cultured on each of the samples.

After being cultured for 1 month under the conditions described above, the cells were immobilized using 4% paraformaldehyde and treated with 1% Triton-X/PBS so as to enhance the membrane permeability. After the cells were subjected to a blocking treatment using an IMAGE IT SIGNAL ENHANCER (trade name, Invitrogen), an anti-human NANOG antibody (AF 1997, R&D Systems, Inc.), an ALEXA FLUOR 555 binding rabbit anti-goat IgG antibody (Invitrogen), and DAPI (Dojindo Molecular Technologies, Inc.) were added thereto for labeling, and the cells were imaged using a fluorescence microscope. FIGS. 4A to 4E show the fluorescence microscopic images.

Figure 3A:
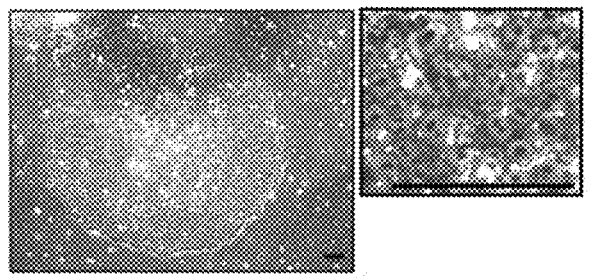
FIGS. 3A to 3E show morphic images (left side) and magnified images (right side) of an iPS cell colony cultured on each polypeptide in reference examples of the present invention.
Figure 3B:
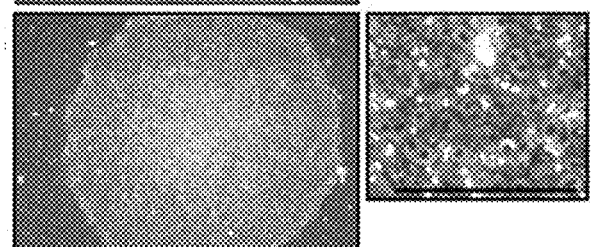
Figure 3C:
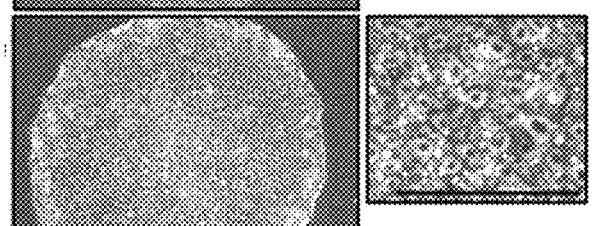
Figure 3D:
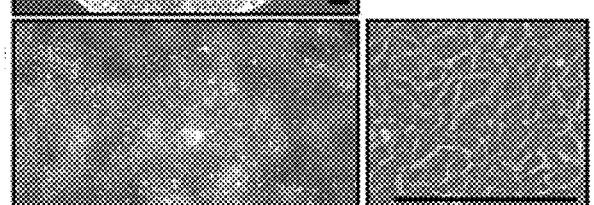
Figure 3E:
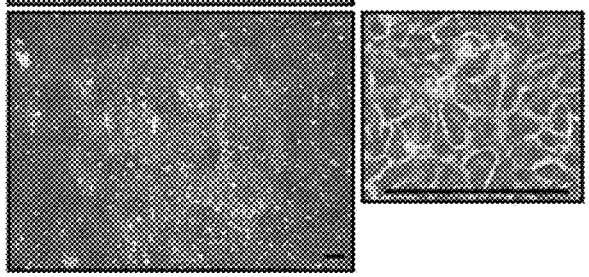
Figure 4A:
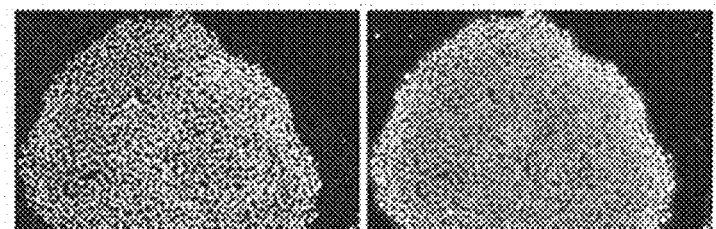
FIGS. 4A to 4E show images of iPS cells stained with DAPI (left side) and images of iPS cells stained with NANOG (right side) that are cultured on each polypeptide in reference examples of the present invention.
Figure 4B:
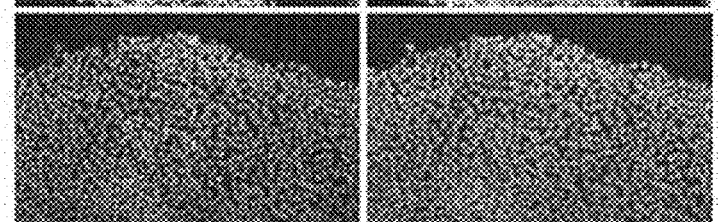
Figure 4C:
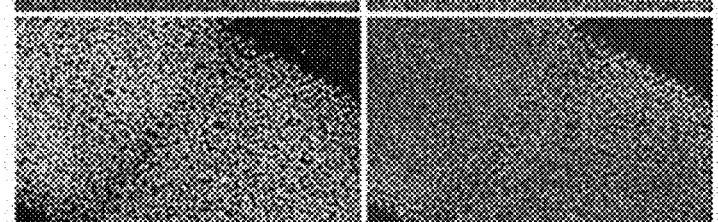
Figure 4D:
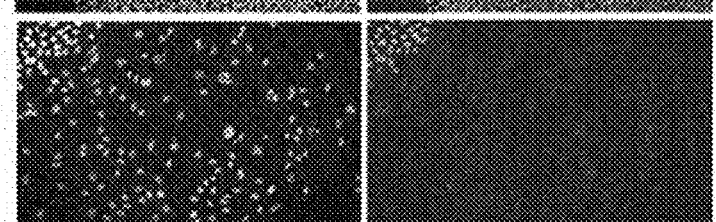
Figure 4E:
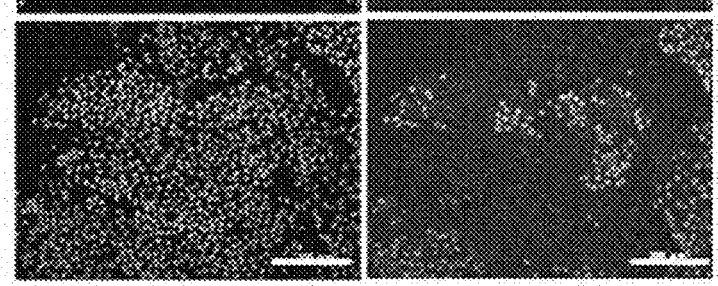

FIGS. 3A and 4A show the iPS cells cultured on RCP-1; FIGS. 3B and 4B show the iPS cells cultured on RCP-11; FIGS. 3C and 4C show the iPS cells cultured on natural human vitronectin; FIGS. 3D and 4D show the iPS cells cultured on rLaminin-5; and FIGS. 3E and 4E show the iPS cells cultured on rLaminin-511. The scale bar in the images indicates 100 µm. In FIGS. 3A to 3E, the images on the left side are full images of the colony, and the images on the right side are magnified images. In FIGS. 4A to 4E, the images on the left side are images of the cells stained with DAPI, and the images on the right side are images of the cells stained with an anti-NANOG antibody. The scale bar in FIGS. 3A to 4E indicates 200 µm.

As shown in FIGS. 3A to 3E, the iPS cells, which were cultured on RCP-1, RCP-11, and the natural human vitronectin including a sequence effective for the cell growth and the adsorption onto the culture dish, had a form specific to undifferentiated cells which have a homogeneous colony and posses nuclei at a high ratio. Furthermore, as shown in FIGS. 4A to 4E, the iPS cells, which were cultured on RCP-1, RCP-11, and the natural human vitronectin having a cell growth region and an adsorption region, strongly expressed NANOG in the entirety of the colony, and accordingly, it was understood that the undifferentiated state is excellently maintained.

From the evaluation results of Reference examples 1 to 7, it was understood that the polypeptide, which includes either the sequence CSYYQSC (SEQ ID NO: 2) or the sequence RGD and the sequence of PRPSLAKKQRFRHRNRKGYR-SQRGHSRGRNQN (SEQ ID NO: 3) and consists of 40 to 450 amino acid residues, is excellent in the adsorbability with respect to the cell culture surface of the support. Furthermore, it was understood that under the condition of co-culture with iPS cells, such a polypeptide is equivalent to RCP-11 having a sequence equivalent to that of the natural vitronectin and human vitronection, in terms of the cell adhesiveness of the iPS cell and the maintenance of the undifferentiated state, and is better than RCP-11 in terms of the growth properties of the iPS cells. It was also understood that all of RCP-1 to RCP-10 and RCP-17 are excellent in terms of the cell adhesiveness of the iPS cells and the maintenance of the undifferentiated state. Such excellent results in terms of the aforementioned abilities were not obtained from other polypeptides or the recombinant laminin as a comparative example.

Therefore, according to the polypeptide (d) of the present invention, it is possible to provide a polypeptide, which enables pluripotent stem cells to grow in an undifferentiated state and is excellent in the adsorbability with respect to the cell culture surface, and a culture method and a culture vessel for pluripotent stem cells using the polypeptide.

Example 1

Preparation of Polypeptide Composition

Among RCP-1 to RCP-10 and RCP-17 obtained as above, RCP-17 was used in the following example.

The solution of the purified polypeptide RCP-17 obtained in Reference example 1 was dialyzed using SLIDE-A-LIZER (trade name, 3.5 K MWCO.). Basically, by using a dialysis buffer (PBS, 1.5 M NaCl, 0.5 M L-arginine, 1 mM EDTA, pH 7.4) as an outer dialysate, urea was removed by stepwise dialysis until the urea concentration became 2 M.

After dialysis, the polypeptide solution was diluted 1/10 (v/v) with a dilution buffer (2 M urea, PBS, 1.5 M NaCl, 0.5 M L-arginine, 1 Mm EDTA, pH 7.4). Then, in order cause oxidation of the polypeptide, the polypeptide solution was dialyzed for 5 days by using an oxidation buffer (2 M urea, 2 mM oxidized glutathione [Wako Pure Chemical Industries, Ltd.], 20 mM reduced glutathione [Wako Pure Chemical Industries, Ltd.], PBS, 1.5 M NaCl, 0.5 M L-arginine, 1 mM EDTA, pH 7.4) as an outer dialysate. Subsequently, the polypeptide solution was dialyzed using a dialysis buffer (PBS, 1.5 M NaCl, 0.5 M L-arginine, 1 mM EDTA, pH 7.4) to remove urea. The end-product of dialysis was concentrated using AMICON ULTRA 3K (trade name, Millipore Corporation) until the polypeptide concentration became 0.5 mg/ml.

The end-product of dialysis was left to stand for 24 hours at 4° C. such that the end-product was sufficiently oxidized, thereby obtaining a polypeptide composition I-1 as an end-product. The concentration of the end-product was calculated from the absorbence at 280 nm by using NANO-DROP (trade name, Thermo Fisher Scientific Inc).

Meanwhile, by using SLIDE-A-LIZER (trade name, 3.5 K MWCO.) and a dialysis buffer (PBS, 1.5 M NaCl, 0.5 M L-arginine, 1 mM EDTA, pH 7.4) as a basic outer dialysate, the solution of the purified polypeptide RCP-17 obtained in Reference example 1 was stepwise dialyzed until the urea concentration became 0 M. In this way, urea was removed, and a comparative polypeptide composition I-2 as an end-product was obtained.

<Properties of Polypeptide Composition>

Figure 5:
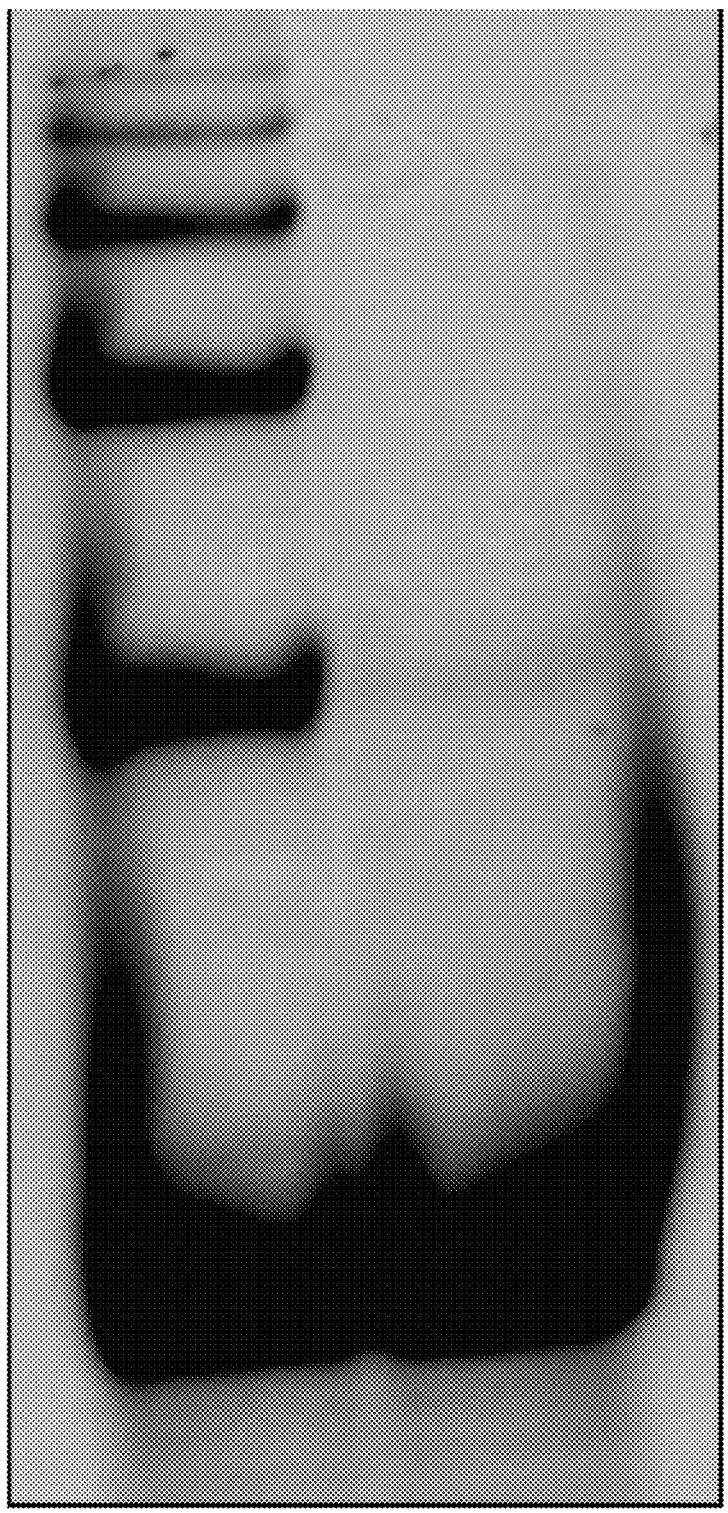
FIG. 5 is an image of gel of SDS-PAGE of polypeptide compositions I-2 (on the left side)

Each of the polypeptide compositions I-1 and I-2 containing the polypeptide RCP-17 obtained as above and a polypeptide composition I-3 as a comparative example containing VTN-N (trade name, recombinant human vitronectin, Life Technologies) was separated using non-reducing SDS PAGE (15% by mass, ATTO Corporation) and stained with a GELCODE™ BLUE STAIN REAGENT (Thermo Scientific Inc.). The results are shown in FIG. 5. By analyzing the obtained stained images by using ImageJ, the Band intensity was quantified, and the abundance ratios of monomers and polymers were calculated. The results are shown in Table 10.

TABLE 10

| Polypeptide composition | Polypeptide type | Mass ratio (% by mass) | | Note |
| --- | --- | --- | --- | --- |
| | | Monomer | Multimer | |
| I-1 | RCP-17 | 95.3 | 4.7 | Example |
| I-2 | RCP-17 | 73.8 | 26.2 | Comparative example |
| I-3 | VTN-N | 20.6 | 79.4 | Comparative example |

In FIG. 5, while the formation of a multimer, in which intermolecular cross-linking occurred, was confirmed in the polypeptide composition I-2 having undergone only the removal of urea by serial dilution and in the polypeptide composition I-3 containing VTN-N, a multimer of RCP-17 was not confirmed in the polypeptide composition I-1 obtained through the oxidation treatment of the polypeptide.

Furthermore, as shown in Table 10, in the polypeptide composition I-1 according to the example, the amount of multimers was equal to or less than 5% by mass.

Example 2

<Cell Growth Property Evaluation 2>

By using the polypeptide compositions I-1 to I-3 obtained in Example 1, cell growth properties were evaluated as below.

Each of the polypeptide compositions I-1 to I-3 was suspended in a predetermined buffer (the polypeptide compositions I-1 and I-2 containing RCP-17 were suspended in the dialysis buffer used for the evaluation of the GRAVY value and aggregation characteristics in reference examples, and the polypeptide composition I-3 containing VTN-N was suspended in PBS) such that the concentration of the polypeptide in the composition became the final concentration as shown in Table 11, thereby preparing polypeptide liquids. Each of the polypeptide liquids was added to the respective wells of a plasma-treated 96-well plate (BD Falcon) made of polystyrene having a plasma-treated cell culture surface, and the plate was held as it is for 2 hours at 37° C. such that the polypeptide was adsorbed thereonto, thereby obtaining a peptide-treated 96-well plate having a polypeptide-coated surface. Into the respective wells of the obtained peptide-treated 96-well plate, iPS cells suspended in a medium obtained by mixing TeSR2 (Stemcell Technologies Inc.) with NUTRISTEM (registered trademark, Bio Industries Inc.) at 1:1 (volume ratio) were seeded at a cell density of 10,000 cells/well. After 72 hours of culture, nonadhesive cells were washed off with PBS, and only adhesive cells were immobilized using 4% by mass paraformaldehyde (Wako Pure Chemical Industries, Ltd.). By using an ATTOPHOS (registered trademark) AP FLUORESCENT SUBSTRATE SYSTEM (Promega Corporation), the ALP activity was calculated, and from the calibration curve, the number of undifferentiated iPS cells having the ALP activity was calculated. The results are shown in Table 11. In Table 11, the cell growth rate is expressed as a ratio calculated by regarding the number of cells after 72 hours of culture using recombinant laminin as being 100%. n=3.

TABLE 11

| Polypeptide composition | Polypeptide type | Concentration of polypeptide added (µg/ml) | Number of cells (%/LN-511) | Note |
| --- | --- | --- | --- | --- |
| I-1 | RCP-17 | 12.5 | 103 ± 4 | Example |
| I-2 | RCP-17 | 12.5 | 75 ± 9 | Comparative example |
| I-3 | VTN-N | 12.5 | 48 ± 2 | Comparative example |

From Table 11, it is understood that the polypeptide composition I-1 according to the example of the present invention is better in the cell growth properties compared to the polypeptide composition I-2. This shows that the formation of a multimeric polypeptide impairs the cell growth activity.

Example 3

Preparation of Polypeptide Composition

Among RCP-1 to RCP-10 and RCP-17 obtained as above, RCP-5 was subjected to a reduction treatment by the following method.

To the polypeptide solution containing RCP-5, Tris(2-carboxyethyl)phosphine Hydrochloride (Wako Pure Chemical Industries, Ltd.) was added such that the final concentration thereof became 100 mM, and the solution was left to stand for 24 hours at 4° C., thereby preparing a sample A.

For comparison, the polypeptide solution containing RCP-5 was frozen at −80° C. without being treated, thereby preparing a sample B.

Each of the samples was dialyzed using SLIDE-A-LIZER (trade name, 3.5 K MWCO.). Basically, a dialysis buffer (PBS, 1.5 M NaCl, 0.5 M L-arginine, 1 mM EDTA, pH 7.4) was used as an outer dialysate, and urea was removed by stepwise dialysis, thereby obtaining polypeptide compositions I-1 (sample A) and II-2 (sample B).

<Structural Analysis of Polypeptide>

By using a Peptide Mass Fingerprint method, disulfide bonds were analyzed. The details thereof are as below.

1) Enzyme Digestion of Protein

900 µL of a 50 mM ammonium bicarbonate buffer solution (pH 7.8) was put into EPPENDORF tubes, and each of the polypeptide compositions II-1 and II-2 was added thereto in an amount of 100 µL. Furthermore, 10 µL of 100 µg/ml trypsin (Wako Pure Chemical Industries, Ltd.) or 500 ng/ml Glu-C (Promega Corporation) was added thereto, and the resulting solution was left to stand overnight at 37° C. By using a centrifugal evaporator (Buchi), the digested fragmented peptides were concentrated until the concentration thereof became 100 µL.

2) Desalting

10 μL of the above digest was desalted using a ZIPTIP C15 chip (trade name, Millipore Corporation), thereby obtaining a measurement samples.

3) MALDI-MS Analysis

By using ULTRAFLEX TOF/TOF (trade name, Bruker Daltonics), each sample was measured at a laser wavelength of 337 nm. The measurement was performed in a reflector mode, and by using PEPTIDE CALIBRATION STANDARD II (trade name, Bruker Daltonics, product number 222570), mass calibration was performed within a range of m/z 700 to 4,000. During the measurement under non-reducing conditions, 1 μL of the peptide digest was mixed with 4 μL of a saturated solution of 0.1% TFA/$H_2O$-MeCN (2:1) of CHCA matrix (α-cyano-4-hydroxycinnamic acid), and the mixture was loaded onto a target plate. During the measurement under reducing conditions, 0.5 μL of the peptide digest was mixed with 0.5 μL of a 40 mM DTT solution (pH 9.0) on a target plate; and the mixture was left to stand for 20 minutes; 0.5 μL of a saturated CHCA matrix solution was loaded onto the plate, followed by drying. On-target washing (desalting) performed after the sample was loaded onto the target plate was conducted according to the protocol from Bruker Daltonics.

4) Evaluation of Measured Value

The obtained values of mass spectrometry were search through MASCOT SERVER (trade name, Matrix Science), and the sequences of the peptides fragmented by each enzyme were identified. Similarly, by investigating the change in mass of the peptides fragmented by the reducing treatment, the cross-linking position of the disulfide bonds involved in cysteine contained in the fragmented peptides was identified.

As a result of the analysis, regarding 4 residues (Cys 5, Cys 9, Cys 19, and Cys 21) on the N-terminal side of RCP-5 contained in the polypeptide composition II-1, the components in which intramolecular cross-linking was established by the pair of Cys 5 and Cys 9 and the pair of Cys19 and Cys 21 were detected. Furthermore, only in RCP-5 contained in the polypeptide composition II-2, a component in which intermolecular cross-linking was established between Cys 39 was observed.

<Evaluation of PAI-1 Binding Properties>

By using a Plasminogen Activator Inhibitor-1 (PAI-1) known to bind with a polypeptide having a structure in which Cys 25 and Cys 31 are cross-linked to each other, detection of the cross-linking structure of Cys 25 and Cys 31 was tried.

The polypeptide compositions II-1 and II-2 (100 μg/ml) were added to a flat-bottomed black 96-well plate (half-Area) made of polystyrene at 64 μL/well. The entirety of the plate was covered with a sealing film (Funakoshi Co., Ltd.) and left to stand at 4° C. such that RCP-5 in each of the polypeptide compositions was immobilized. After 12 hours, the liquid in the wells was discarded, and TBS (NIPPON GENE CO., LTD.) containing 5% Bovine Serum Albumin (Sigma-Aldrich Co, LLC.) was added thereto at 150 μL/well. The plate was left to stand for 1 hour at 37° C., and then the liquid in the wells was discarded. Furthermore, BLOCKER CASEIN (trade name, Thermo Scientific Inc.) was added thereto at 150 μL/well, and the plate was left to stand at 37° C. as above so as to performing blocking. After 1 hour, TBS (TBST) containing 0.05% Tween 20 was added thereto at 150 μL/well, and the liquid was continuously discarded from the wells. By performing the above operation 4 times in total, the inside of the wells was washed.

Then, a solution of recombinant PAI-1 (catalog number 1786-PI, R & D Systems Inc) serially diluted with TBS from 170 nM to 2.6 nM at the same factor was added to the respective well at 50 μL/well, and the plate was left to stand at 37° C. After 1 hour, the PAI-1 solution was discarded from the wells, and the wells were washed with TBST 4 times in total by the same method as described above, thereby removing unbound PAI-1. Thereafter, an undiluted solution of unlabeled anti-goat IgG H+L (catalog number A10537, Life Technologies) was diluted 700-fold with TBS and added to the wells at 150 μL/well, and the plate was left to stand at 37° C. to perform blocking. After 1 hour, the antibody solution was discarded from the wells, and the wells were washed with TBST 4 times in total by the same method as described above. Subsequently, an undiluted solution of anti-PAI-1 antibodies (catalog number AF1786, R & D Systems Inc) was diluted 100-fold with TBS and added to the wells at 100 μL/well, and the plate was left to stand for 1 hour at 37° C. Then, the antibody solution was discarded from the wells, and the wells were washed with TBST 4 times in total by the same method as described above, thereby removing unbound anti-PAI-1 antibodies.

Furthermore, an undiluted solution of HRP-labeled anti-goat IgG antibodies (catalog number 81-1620, Life Technologies) was diluted 7,500-fold with TBS and added to the wells at 100 μL/well. The plate was left to stand for 1 hour at 37° C., the antibody solution was then discarded from the wells, and the wells were washed 4 times in total with TBST by the same method as described above, thereby removing unbound labeled antibodies. Subsequently, by using QUANTABLU FLUOROGENIC PEROXIDASE SUBSTRATE KIT (trade name, Thermo Scientific Inc.), the HRP matrix was adjusted as described in the instruction and added to the wells at 50 μL/well. The plate was left to stand for 20 minutes at 37° C. in a dark place, and a stop solution included in the same kit was added thereto at 50 μL/well so as to stop the reaction. The excitation wavelength and the fluorescence wavelength were set to be 330 nm and 410 nm respectively, and the binding of RCP-5 to PAI-1 was measured as a relative fluorescence unit by using ENVISION (trade name, PerkinElmer Inc).

Figure 6:
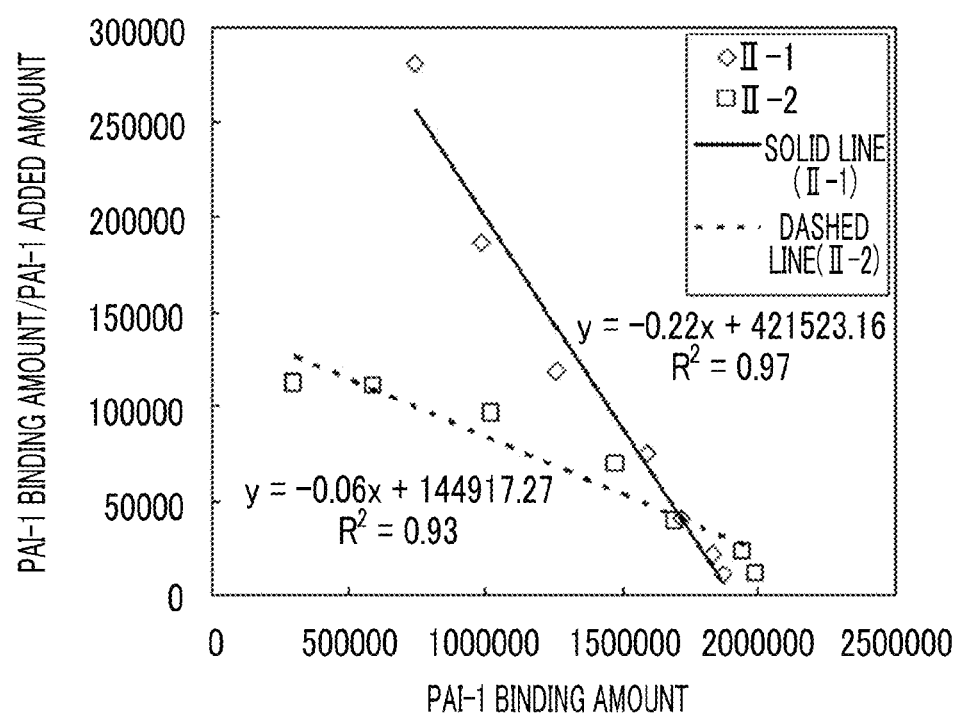
FIG. 6 is a graph showing a binding relationship between polypeptides in the polypeptide compositions according to examples of the present invention and PAI-1.

FIG. 6 shows the results obtained by plotting the obtained measurement values to the ordinate and plotting the values, obtained by dividing the measurement values by the concentration (nM) of the PAI-1 added, to the abscissa. The obtained straight line corresponds to the following equation of scatched plot, and hence the binding constant (KA) can be calculated from the slope.

(Equation)

Amount of *PAI*-1 bound/amount of *PAI*-1 added=−
    *KA*×amount of *PAI*-1 bound The calculated results are shown in Table 12. The binding constant of PAI-1 was greater for RCP-5 in the polypeptide composition II-1 than for RCP-5 in the polypeptide composition II-2. That is, it was understood that the number of Cys 25, Cys 31, and intramolecular cross-linking structures is greater in RCP-5 in the polypeptide composition II-1.

TABLE 12

| Polypeptide composition | Binding constant | Note |
|---|---|---|
| II-1 | 0.22 | Example |
| II-2 | 0.06 | Comparative example |

<Cell Growth Property Evaluation>

By the same method as described in <Cell growth property evaluation 2> of Example 3, the cell growth properties of the polypeptide compositions II-1 and II-2 was evaluated. The results are shown in Table 13. The cell growth properties of the polypeptide composition II-1 were better than that of the polypeptide composition II-2. That is, it was understood that the polypeptide in which Cys 25, Cys 31, and the intramolecular cross-linking structure bind with each other is excellent in the cell growth activity.

TABLE 13

| Polypeptide composition | Number of cells (%/LN-511) | Note |
|---|---|---|
| II-1 | 107 ± 47 | Example |
| II-2 | 79 ± 5 | Comparative example |

As described above, the polypeptide composition of the present invention is a peptide composition containing a large amount of polypeptide, which includes a partial sequence of the N-terminal side of a predetermined human vitronectin and has an amino acid sequence exhibiting a cell adhesion ability with respect to pluripotent stem cells, not in the form of a multimer composed of two or more monomers held together by intermolecular cross-linking via cysteine residues on the N-terminal side of the human vitronectin but in the form of a monomer in which the intermolecular cross-linking does not occur. It was understood that pluripotent stem cells efficiently grow in the presence of such a polypeptide composition.

Therefore, according to the present invention, it is possible to provide a polypeptide composition, which can induce a pluripotent stem cell culturing property, particularly, an excellent cell growth ability, and to provide a culture method for pluripotent stem cells using the polypeptide composition.

The entirety of the disclosure of JP2013-227583 filed on Oct. 31, 2013 is incorporated into the present specification by reference.

All of the documents, patent applications, and technical standards described in the present specification are incorporated into the present specification by reference as if each of the documents, patent applications, and technical standards is specifically and independently described so as to be incorporated into the present specification by reference.

What is claimed is:

1. A polypeptide composition comprising a polypeptide (d) consisting of 40 to 450 amino acid residues,
   the polypeptide (d) comprising a first region and a second region,
   the first region being represented by any one of the following amino acid sequences (1-i) to (1-iii):
   (1-i) an amino acid sequence consisting of the 1st to 44th amino acid residues of an amino acid sequence represented by SEQ ID NO: 1,
   (1-ii) an amino acid sequence consisting of an amino acid sequence that has identity of equal to or higher than 80% with an amino acid sequence including the amino acid sequence (1-i), and having a cell adhesion ability with respect to pluripotent stem cells, and
   (1-iii) an amino acid sequence consisting of an amino acid sequence that is formed by deletion, substitution, or addition of one amino acid or plural amino acids in the amino acid sequence (1-i), and having a cell adhesion ability with respect to pluripotent stem cells,
   the second region being represented by any one of the following amino acid sequences (2-i) to (2-iii):
   (2-i) an amino acid sequence represented by PRPSLAKKQRFRHRNRKGYRSQRGHSRGRNQN (SEQ ID NO: 3),
   (2-ii) an amino acid sequence which has identity of equal to or higher than 80% with the amino acid sequence represented by SEQ ID NO: 3, and has adsorbability with respect to a cell culture surface of a support, and
   (2-iii) an amino acid sequence that is formed by deletion, substitution, or addition of one amino acid or plural amino acids in the amino acid sequence represented by SEQ ID NO: 3, and has adsorbability with respect to a cell culture surface of a support,
   wherein the polypeptide (d) does not include the 56th to 268th amino acid residues in the amino acid sequence represented by SEQ ID NO: 1, and
   an amount of a multimeric polypeptide, which is the polypeptide (d) and composed of two or more monomers held together by intermolecular cross-linking via cysteine residues included in the first region, being equal to or less than 20% by mass of a total mass of polypeptides contained in the composition.

2. The polypeptide composition according to claim 1, wherein an amount of a multimeric polypeptide composed of two or more monomers held together by intermolecular cross-linking via cysteine residues in any positions in the polypeptide is equal to or less than 20% by mass of the total mass of polypeptides contained in the composition.

3. The polypeptide composition according to claim 1, wherein the polypeptide (d) includes at least one polypeptide in which intramolecular cross-linking is established between a cysteine residue corresponding to the 25th amino acid residue of the amino acid sequence represented by SEQ ID NO: 1 and included in the first region and a cysteine residue corresponding to the 31st amino acid residue of the same amino acid sequence.

4. The polypeptide composition according to claim 1, wherein the polypeptide (d) includes a polypeptide in which intramolecular cross-linking is established:
   between a cysteine residue corresponding to the 5th amino acid residue of the amino acid sequence represented by SEQ ID NO: 1 and included in the first region and a cysteine residue corresponding to the 9th amino acid residue of the same amino acid sequence;
   between a cysteine residue corresponding to the 19th amino acid residue and of the amino acid sequence represented by SEQ ID NO: 1 and included in the first region a cysteine residue corresponding to the 21st amino acid residue of the same amino acid sequence;
   between a cysteine residue corresponding to the 25th amino acid residue of the amino acid sequence represented by SEQ ID NO: 1 and included in the first region and a cysteine residue corresponding to the 31st amino acid residue of the same amino acid sequence; and
   between a cysteine residue corresponding to the 32nd amino acid residue of the amino acid sequence represented by SEQ ID NO: 1 and included in the first region and a cysteine residue corresponding to the 39th amino acid residue of the same amino acid sequence.

5. The polypeptide composition according to claim 1, wherein a binding constant between the polypeptide contained in the composition and a plasminogen activator inhibitor-1 is greater than 0.06 $nM^{-1}$.

6. The polypeptide composition according to claim 1, further comprising, as the polypeptide (d), at least one polypeptide that further includes a third region containing any one of the following amino acid sequences (3a-i) to (3a-iii):
   (3a-i) a partial amino acid sequence of an amino acid sequence that consists of the 56th to 341st amino acid residues of the amino acid sequence represented by SEQ ID NO: 1,
   (3a-ii) an amino acid sequence having identity of equal to or higher than 80% with the amino acid sequence (3a-i) or a partial amino acid sequence of the amino acid sequence having identity of equal to or higher than 80% with the amino acid sequence (3a-i), and
   (3a-iii) an amino acid sequence formed by deletion, substitution, or addition of one amino acid or plural amino acids in the amino acid sequence (3a-i) or a partial amino acid sequence of the amino acid sequence formed by deletion, substitution, or addition of one amino acid or plural amino acids in the amino acid sequence (3a-i).

7. The polypeptide composition according to claim 1, further comprising, as the polypeptide (d), at least one polypeptide that includes a fourth region containing any one of the following amino acid sequences (4a-i) to (4a-iii):
   (4a-i) an amino acid sequence that consists of the 374th to 459th amino acid residues of the amino acid sequence represented by SEQ ID NO: 1, or a partial amino acid sequence of the amino acid sequence that consists of the 374th to 459th amino acid residues of the amino acid sequence represented by SEQ ID NO: 1,
- (4a-ii) an amino acid sequence having identity of equal to or higher than 80% with the amino acid sequence (4a-i) or a partial amino acid sequence the amino acid sequence having identity of equal to or higher than 80% with the amino acid sequence (4a-i), and
- (4a-iii) an amino acid sequence formed by deletion, substitution, or addition of one amino acid or plural amino acids in the amino acid sequence (4a-i) or a partial amino acid sequence of the amino acid sequence formed by deletion, substitution, or addition of one amino acid or plural amino acids in the amino acid sequence (4a-i).

8. A culture method for pluripotent stem cells, comprising culturing pluripotent stem cells in the presence of the polypeptide composition according to claim 1.

9. A culture vessel comprising:
a support having a cell culture surface; and
the polypeptide contained in the polypeptide composition according to claim 1, which is disposed on the cell culture surface of the support.

10. A polypeptide composition comprising a polypeptide including a first region and a third region,
the first region being represented by any one of the following amino acid sequences (1-i) to (1-iii):
- (1-i) an amino acid sequence consisting of the 1st to 44th amino acid residues of the amino acid sequence represented by SEQ ID NO: 1,
- (1-ii) an amino acid sequence consisting of an amino acid sequence which has identity of equal to or higher than 80% with an amino acid sequence including the amino acid sequence (1-i), and having a cell adhesion ability with respect to pluripotent stem cells, and
- (1-iii) an amino acid sequence consisting of an amino acid sequence that is formed by deletion, substitution, or addition of one amino acid or plural amino acids in the amino acid sequence (1-i), and having a cell adhesion ability with respect to pluripotent stem cells,
the third region being represented by any one of the following amino acid sequences (3a-i) to (3a-iii):
- (3a-i) a partial amino acid sequence of an amino acid sequence that consists of the 56th to 341st amino acid residues of the amino acid sequence represented by SEQ ID NO: 1,
- (3a-ii) an amino acid sequence having identity of equal to or higher than 80% with the amino acid sequence (3a-i) or a partial amino acid sequence of the amino acid sequence having identity of equal to or higher than 80% with the amino acid sequence (3a-i),
- (3a-iii) an amino acid sequence formed by deletion, substitution, or addition of one amino acid or plural amino acids in the amino acid sequence (3a-i) or a partial amino acid sequence of the amino acid sequence formed by deletion, substitution, or addition of one amino acid or plural amino acids in the amino acid sequence (3a-i),
wherein the polypeptide including the first region and the third region does not include the 56th to 268th amino acid residues in the amino acid sequence represented by SEQ ID NO: 1, and
an amount of a multimeric polypeptide, which is the polypeptide including the first region and the third region and is composed of two or more monomers held together by intermolecular cross-linking via cysteine residues included in the first region, is equal to or less than 20% by mass of a total mass of polypeptides contained in the composition.

11. A culture method for pluripotent stem cells, comprising culturing pluripotent stem cells in the presence of the polypeptide composition according to claim 10.

12. A culture vessel comprising:
a support having a cell culture surface; and
the polypeptide contained in the polypeptide composition according to claim 10, which is disposed on the cell culture surface of the support.

13. A polypeptide composition comprising a polypeptide including a first region and a fourth region,
the first region being represented by any one of the following amino acid sequences (1-i) to (1-iii):
- (1-i) an amino acid sequence consisting of the 1st to 44th amino acid residues of the amino acid sequence represented by SEQ ID NO: 1,
- (1-ii) an amino acid sequence consisting of an amino acid sequence which has identity of equal to or higher than 80% with an amino acid sequence including the amino acid sequence (1-i), and having a cell adhesion ability with respect to pluripotent stem cells, and
- (1-iii) an amino acid sequence consisting of an amino acid sequence that is formed by deletion, substitution, or addition of one amino acid or plural amino acids in the amino acid sequence (1-i), and having a cell adhesion ability with respect to pluripotent stem cells,
the fourth region being represented by any one of the following amino acid sequences (4a-i) to (4a-iii):
- (4a-i) an amino acid sequence that consists of the 374th to 459th amino acid residues of the amino acid sequence represented by SEQ ID NO: 1, or a partial amino acid sequence of the amino acid sequence that consists of the 374th to 459th amino acid residues of the amino acid sequence represented by SEQ ID NO: 1,
- (4a-ii) an amino acid sequence having identity of equal to or higher than 80% with the amino acid sequence (4a-i) or a partial amino acid sequence of the amino acid sequence having identity of equal to or higher than 80% with the amino acid sequence(4a-i), and
- (4a-iii) an amino acid sequence formed by deletion, substitution, or addition of one amino acid or plural amino acids in the amino acid sequence (4a-i) or a partial amino acid sequence of the amino acid sequence formed by deletion, substitution, or addition of one amino acid or plural amino acids in the amino acid sequence (4a-i),
wherein the polypeptide including the first region and the fourth region does not include the 56th to 268th amino acid residues in the amino acid sequence represented by SEQ ID NO: 1, and
an amount of a multimeric polypeptide, which is the polypeptide including the first region and the fourth region and is composed of two or more monomers held together by intermolecular cross-linking via cysteine residues included in the first region, is equal to or less than 20% by mass of a total mass of polypeptides contained in the composition.

14. A culture method for pluripotent stem cells, comprising culturing pluripotent stem cells in the presence of the polypeptide composition according to claim 13.

15. A culture vessel comprising:
a support having a cell culture surface; and
the polypeptide contained in the polypeptide composition according to claim 13, which is disposed on the cell culture surface of the support.

* * * * *